US009029521B2

(12) United States Patent
Mano et al.

(10) Patent No.: US 9,029,521 B2
(45) Date of Patent: May 12, 2015

(54) EML4-ALK FUSION GENE

(75) Inventors: Hiroyuki Mano, Tokyo (JP); Sadao Kuromitsu, Tokyo (JP); Nobuaki Shindo, Tokyo (JP); Takatoshi Soga, Tokyo (JP); Takashi Furutani, Tokyo (JP)

(73) Assignees: Astellas Pharma Inc., Tokyo (JP); Curegene K.K., Tokyo (JP)

( * ) Notice: Subject to any disclaimer, the term of this patent is extended or adjusted under 35 U.S.C. 154(b) by 0 days.

(21) Appl. No.: 13/468,730

(22) Filed: May 10, 2012

(65) Prior Publication Data
US 2013/0158095 A1 Jun. 20, 2013

Related U.S. Application Data

(62) Division of application No. 13/086,245, filed on Apr. 13, 2011, now Pat. No. 8,197,818, which is a division of application No. 12/466,920, filed on May 15, 2009, now Pat. No. 7,964,710, which is a division of application No. 11/845,498, filed on Aug. 27, 2007, now Pat. No. 7,728,120.

(30) Foreign Application Priority Data

Oct. 11, 2006 (JP) ................. 2006/277718
May 1, 2007 (JP) ................. 2007/120670

(51) Int. Cl.
*C07K 14/435* (2006.01)
*C12N 9/12* (2006.01)
*C07K 14/47* (2006.01)
*A61K 31/506* (2006.01)
*C12N 15/113* (2010.01)
*C12Q 1/48* (2006.01)
*C12Q 1/68* (2006.01)

(52) U.S. Cl.
CPC .............. *C12N 9/1205* (2013.01); *C07K 14/47* (2013.01); *A61K 31/506* (2013.01); *C12N 15/1137* (2013.01); *C12Q 1/485* (2013.01); *C12Q 1/6886* (2013.01); *C07K 2319/00* (2013.01)

(58) Field of Classification Search
None
See application file for complete search history.

(56) References Cited

FOREIGN PATENT DOCUMENTS

| WO | 2004/080980 A1 | 9/2004 |
|---|---|---|
| WO | 2005/009389 A2 | 2/2005 |
| WO | 2005/016894 A1 | 2/2005 |
| WO | 2005/097765 A1 | 10/2005 |
| WO | 2008/127248 A1 | 10/2008 |

OTHER PUBLICATIONS

Anna V. Galkin, et al.; "Identification of NVP-TAE684, a Potent, Selective, and Efficacious Inhibitor of NPM-ALK"; PNAS 2007; pp. 270-275; vol. 104, No. 1.

Brandon Lawrence, et al.; "TPM3-ALK and TPM4-ALK Oncogenes in Inflammatory Myofibroblastic Tumors"; American Journal of Pathology; 2000; pp. 377-384; vol. 157, No. 2.
Christian Touriol, et al.; "Further Demonstration of the Diversity of Chromosomal Changes Involving 2p23 in ALK-positive Lymphoma: 2 cases Expressing ALK Kinase Fused to CLTCL (Clathrin Chain Polypeptide-like)" Blood; 2000; pp. 3204-3207; vol. 95, No. 10.
GenBank accession No. AB209477; (submitted on Mar. 31, 2005) Source: http://www.ncbi.nlm.nih.gov/entrez/viewer.fcgi?db=nuccore&id=62088533.
GenBank accession No. NM_019063; (submitted on Jul. 27, 2000) Source: http://www.ncbi.nlm.nih.gov/entrez/viewer.fcgi?19923496:NCBI:12636854.
Gisele W. B. Colleoni, et al.; "ATIC-ALK: A Novel Variant ALK Gene Fusion in Anaplastic Large Cell Lymphoma Resulting From the Recurrent Cryptic Chromosomal Inversion, inv(2)(p23q35)"; Americal Journal of Pathology; 2000; pp. 781-789; vol. 156, No. 3.
Hiroyuki Mano; "A Novel Transforming Fusion Kinase in Lung Cancer"; ML10 Proceedings of the 66th Annual Meeting of the Japanese Cancer Association; Issued Aug. 25, 2007.
Ioannis Panagopoulos, et al.; "Fusion of the SEC31L1 and ALK Genes in an Inflammatory Myofibroblastic Tumor"; International Journal of Cancer; 2006; pp. 1181-1186; vol. 118.
Kojo S.J. Elenitoba-Johnson, et al.; "Proteomic Identification of Oncogenic Chromosomal Translocation Partners Encoding Chimeric Anaplastic Lymphoma Kinase Fusion Proteins"; PNAS; 2006; pp. 7402-7407; vol. 103, No. 19.
Larisa V. Debelenko, et al.; "Identification of CARS-ALK Fusion in Primary and Metastatic Lesions of an Inflammatory Myofibroblastic Tumor"; Laboratory Investigation; 2003; pp. 1255-1265; vol. 83, No. 9.
Luis Hernandez, et al.; "Diversity of Genomic Breakpoints in TFG-ALK Translocations in Anaplastic Large Cell Lymphomas"; American Journal of Pathology; 2002; pp. 1487-1494; vol. 160, No. 4.
Luis Hernandez, et al.; "TRK-Fused Gene (TFG) Is a New Partner of ALK in Anaplastic Large Cell Lymphoma Producing Two Structurally Different TFG-ALK Translocations"; Blood; 1999; pp. 3265-3268; vol. 94, No. 9.
Mami Shiota, et al.; "Anaplastic Large Cell Lymphomas Expressing the Novel Chimeric Protein p80NPM/ALK: a Distinct Clinicopathologic Entity"; Blood; 1995; pp. 1954-1960; vol. 86, No. 5.

(Continued)

*Primary Examiner* — Misook Yu
*Assistant Examiner* — Nelson B Moseley, II
(74) *Attorney, Agent, or Firm* — Oblon, McClelland, Maier & Neustadt, L.L.P.

(57) ABSTRACT

The present inventors found that a fusion gene present in some cancer patients is an oncogene. The present invention relates to a polypeptide as a novel fusion protein, a polynucleotide encoding the polypeptide, a vector comprising the polynucleotide, a transformed cell comprising the vector, a method for detecting the fusion protein or polynucleotide, a method for screening a therapeutic agent for cancer, and a method for treating cancer that is shown to be positive for the fusion gene. Further, the present invention relates kit, primer set, and probe useful in the detection of cancer that is shown to be positive for the fusion gene.

4 Claims, 7 Drawing Sheets
(4 of 7 Drawing Sheet(s) Filed in Color)

(56) References Cited

OTHER PUBLICATIONS

Mami Shiota, et al.; "Hyperphosphorylation of a Novel 80 kDa Protein-tyrosine Kinase Similar to Ltk in a Human Ki-1 Lymphoma Cell Line, AMS3"; Oncogene; 1994; pp. 1567-1574; vol. 9; Macmillan Press, Ltd.

Manabu Soda, et al.; "A Novel Transforming Fusion Kinase Identified in Non-small-cell Lung Cancer"; O-455, Proceedings of the 66th Annual Meeting of the Japanese Cancer Association; Issued Aug. 25, 2007.

Manabu Soda, et al.; "Identification of the Transforming EML4-ALK Fusion Gene in Non-small-cell Lung Cancer"; Nature; (2007); pp. 561-567 and 1-11; vol. 448; Nature Publishing Group.

Marc Pollmann, et al.; "Human EML4, a Novel Member of the EMAP Family, is Essential for Microtubule Formation"; Experimental Cell Research; 2006; pp. 3241-3251.

Martin U. Kuefer, et al.; "Retrovirus-Mediated Gene Transfer of NPM-ALK Causes Lymphoid Malignancy in Mice"; Blood; 1997; pp. 2901-2910; vol. 90, No. 8.

Michal Marzec, et al.; "Inhibition of ALK Enzymatic Activity in T-cell Lymphoma Cells Induces Apoptosis and Suppresses Proliferation and STAT3 Phosphorylation Independently of Jak3"; Laboratory Investigation; 2005; pp. 1544-1554; vol. 85.

Roberto Piva, et al.; "Ablation of Oncogenic ALK is a Viable Therapeutic Approach for Anaplastic Large-cell Lymphomas"; Blood; 2006; pp. 689-697; vol. 107, No. 2.

Rongshi Li, et al.; "Design and Synthesis of 5-Aryl-pyridone-carboxamides as Inhibitors of Anaplastic Lymphoma Kinase"; Journal of Medical Chemistry; 2006; pp. 1006-1015; vol. 49.

Stephan W. Morris, et al.; "Fusion of a Kinase Gene, ALK, to a Nucleolar Protein Gene, NPM, in Non-Hodgkin's Lymphoma"; Science; 1994; pp. 1281-1284; vol. 263.

Tong Zhu, et al. "Polymer-Supported Synthesis of Pyridone-Focused Libraries as Inhibitors of Anaplastic Lymphoma Kinase"; Journal of Combinatorial Chemistry; 2006; pp. 401-409; vol. 8, No. 3.

Toshinori Iwahara, et al. "Molecular Characterization of ALK, a Receptor Tyrosine Kinase Expressed Specifically in the Nervous System"; Oncogene; 1997; pp. 439-449; vol. 14; Stockton Press.

Virginie Lacronique, et al.; "A TEL-JAK2 Fusion Protein with Constitutive Kinase Activity in Human Leukemia"; Science; 1997; pp. 1309-1312; vol. 278.

Weihua Wan, et al.; "Anaplastic Lymphoma Kinase Activity is Essential for the Proliferation and Survival of Anaplastic Large-cell Lymphoma Cells"; Blood; 2006; pp. 1617-1623; vol. 107, No. 4.

Willy G. Dirks, et al.; "Expression and Functional Analysis of the Anaplastic Lymphoma Kinase (ALK) Gene in Tumor Cell Lines"; International Journal of Cancer; 2002; pp. 49-56; vol. 100.

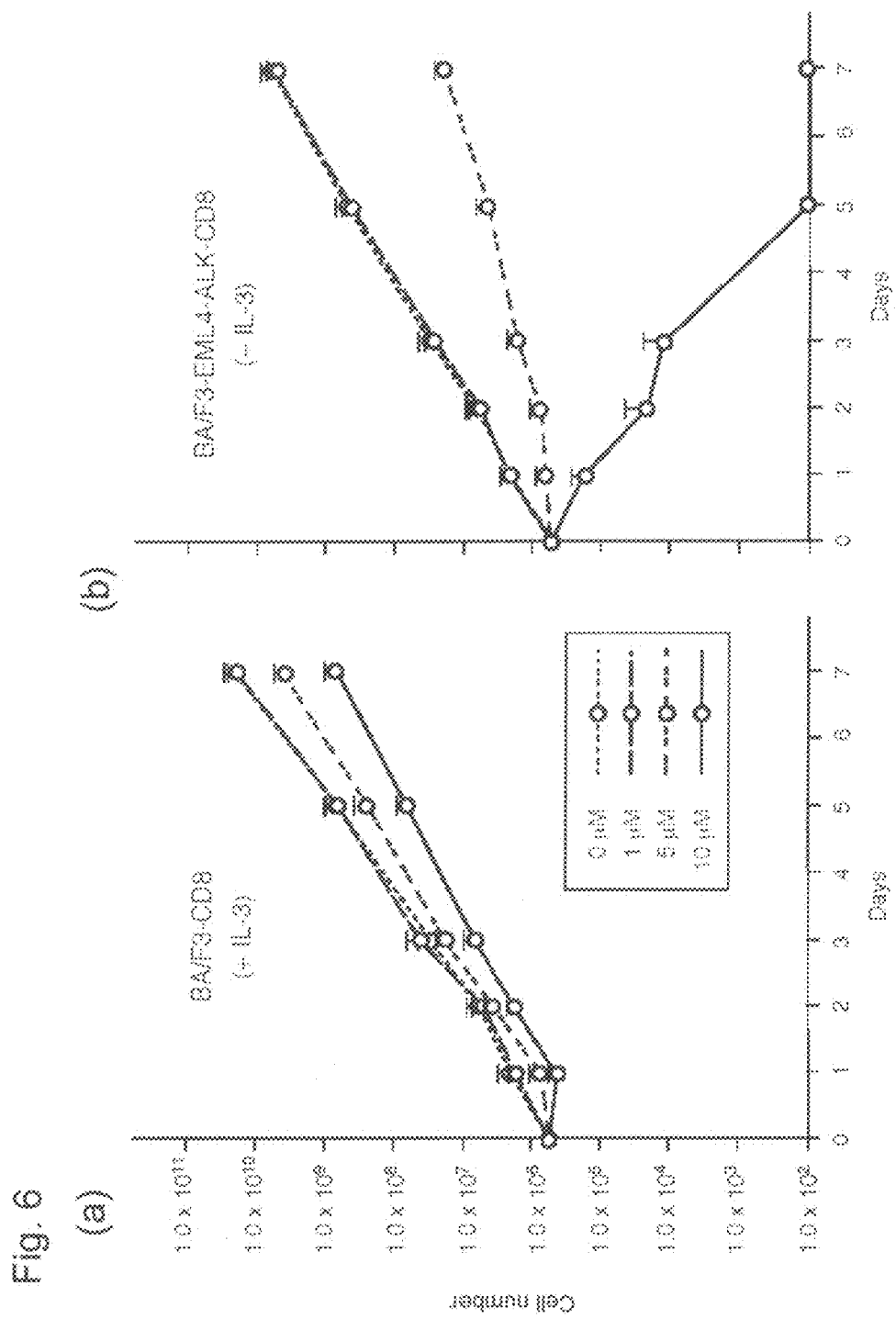

Fig. 7 siRNA-1
5'    UGGGAAAGGACCUAAAGTGTA    3'
3' GGACCCUUUCCUGGATTTCAC      5' siRNA-2
5'    GGGAAAGGACCUAAAGTGTAC   3'
3' GACCCUUUCCUGGAUTTCACA      5' siRNA-3
5'    GGACCUAAAGUGUACCGCCGG   3'
3' UUCCUGGAUUUCACATGGCGG      5' siRNA-4
5'    CCUAAAGUGUACCGCCGGAAG   3'
3' CUGGAUUUCACAUGGCGGCCT      5' siRNA-5
5'    AAAGUGUACCGCCGGAAGCAC   3'
3' GAUUUCACAUGGCGGCCTTCG      5' siRNA-6
5'    AAGUGUACCGCCGGAAGCACC   3'
3' AUUUCACAUGGCGGCCTTCGT      5' siRNA-7
5'    GGCCUGUAUACCGGATAATGA   3'
3' ACCCGGACAUAUGGCCTATTA      5' siRNA-8
5'    GGCCUGUAUACCGGAUAAUGA   3'
3' ACCCGGACAUAUGGCCUAUUA      5' siRNA-9
5'    CGGCUGCAAUCGATTGATAGC   3'
3' AAGCCGACGUUAGCUAACTAT      5'

EML4-ALK FUSION GENE

CROSS-REFERENCE TO RELATED APPLICATIONS

This is a divisional of application Ser. No. 13/086,245 filed Apr. 13, 2011, which is a divisional of application Ser. No. 12/466,920, filed May 15, 2009, now U.S. Pat. No. 7,964,710, issued Jun. 21, 2011, which is a divisional of application Ser. No. 11/845,498 filed Aug. 27, 2007, now U.S. Pat. No. 7,728,120, issued Jun. 1, 2010. The entire disclosure of the prior applications, U.S. patent application Ser. Nos. 11/845,498, 12/466,920 and 13/806,245, is hereby incorporated herein by reference in their entirety.

BACKGROUND OF THE INVENTION

1. Field of the Invention

The present invention relates to a polypeptide as a novel fusion protein, a polynucleotide encoding the polypeptide, a vector comprising the polynucleotide, a transformed cell comprising the vector, a method for detecting the fusion protein or polynucleotide, a method for screening a therapeutic agent for cancer, and a therapeutic agent for cancer.

2. Background Art (Carcinogenesis and Gene)

Several cancer-related genes have been known so far. In particular, tyrosine kinase genes, which encode important enzymes directly regulating cell growth, have been known to be activated even by substitution or deletion in amino acid sequences and thereby bring about carcinogenesis (Non-Patent Document 1).

For example, BCR-ABL fusion genes are found in most of patients with chronic myeloid leukemia. Proteins produced by this abnormal gene cause the abnormal growth of leukemia cells and simultaneously tend to inhibit blood cell apoptosis, leading to the onset of chronic myeloid leukemia (Non-Patent Document 24). Imatinib mesylate, an inhibitor of ABL tyrosine kinase, is effective for the treatment of this disease. Alternatively, TEL-JAK2 fusion proteins have been reported to be observed in acute lymphoblastic leukemia, while NPM-ALK fusion genes encoding NPM fused with ALK tyrosine kinase are observed in more than half of the cases of anaplastic large cell lymphoma (ALCL) and the activation of ALK kinase has been shown to be important for tumor cell growth by NPM-ALK (Non-Patent Documents 25 and 14).

(Lung Cancer and Oncogene)

In 2004, Paez et al. (Non-Patent Document 2) and Lynch et al. (Non-Patent Document 3) have shown that epidermal growth factor receptor (EGFR) genes having sequence abnormalities are expressed in some lung cancer cells. They have also reported that gefitinib (trademark: Iressa), a kinase activity inhibitor of EGFR, is therapeutically effective for patients having these EGFR mutations. Subsequent analyses have demonstrated that EGFR mutations are frequently observed in Asians, nonsmokers, and female patients with lung cancer, and that gefitinib is significantly effective for some of these cases (Non-Patent Documents 4 and 5).

Regarding the involvement of tumor suppressor genes, it has previously been reported that the inactivation of TP53 gene and Rb pathway occurs in lung cancer with a high frequency (Non-Patent Document 6). By contrast, regarding an active type of oncogene that strongly positively induces the cell growth of lung cancer, only KRAS1 gene activation in some cases has been reported (Non-Patent Document 7). The presence of a new type of abnormal kinase has been reported to be found in approximately 10% of lung cancer cases, and this report, however, has made no reference to specific molecules (Non-Patent Document 36).

In 2000, EML4 (echinoderm microtubule-associated protein like protein 4) (Non-Patent Document 26) has been reported as a cytoplasmic protein with a molecular weight of 120,000, which is highly expressed in the M phase of the cell cycle (Non-Patent Document 8). A human EML4 gene encodes a polypeptide with 981 amino acids and has 23 exons. This gene has been mapped to chromosome 2. The EML4 protein has a basic region at the amino terminus, as with other members of the EML family, and further has carboxyl-terminal WD domains. The physiological functions of EML4 have been little known. However, according to a recent report, EML4 participates in microtubule formation (Non-Patent Document 9).

On the other hand, ALK (Anaplastic Lymphoma Kinase) (Non-Patent Document 27) is receptor tyrosine kinase. This protein has a transmembrane domain in the central part and has a carboxyl-terminal tyrosine kinase region and an amino-terminal extracellular domain (Non-Patent Document 28). The ALK gene, which has 30 exons encoding a polypeptide with 1620 amino acids, has been mapped to chromosome 2. This ALK gene has been thought, from the site or timing of its expression, to participate in the development or functions of the nervous system (Non-Patent Document 10). Loren et al. have reported from the homolog analysis of *Drosophila* ALK that ALK participates in muscle differentiation (Non-Patent Document 11). However, no abnormality has been observed in ALK knockout mice, and its distinct physiological functions still remain to be elucidated (Non-Patent Document 12).

Full-length ALK expression has been reported so far in some cancer cells of ectodermal origin, such as neuroblastoma, glioblastoma, breast cancer, and melanoma (the full-length ALK expression has not been observed in cancer cells of endodermal and mesodermal origins) (Non-Patent Document 13). Full-length ALK is expressed in many neuroblastoma cell lines. However, the autophosphorylation of ALK is not observed in these neuroblastoma cell lines. Moreover, ALK expression has been reported, from the cohort analysis of neuroblastoma patients, to be weakly associated with canceration. It has been suggested that ALK expression in neuroblastoma may reflect its expression in normal neural differentiation, rather than its association with canceration (Non-Patent Document 10). On the other hand, in reported cases, ligands such as pleiotrophin and midkine as well as the gene amplification of ALK itself increase the autophosphorylation of ALK and mobilize intracellular signals. It has also been reported that ALK may contribute to cancer cell growth (Non-Patent Document 12).

In some cases of human malignant lymphoma and inflammatory myofibroblastic tumor, the ALK gene has been reported to be fused with other genes (NPM, CLTCL, TFG, CARS, SEC31L1, etc.) as a result of chromosomal translocation or inversion and thereby form a fusion type of tyrosine kinase (Non-Patent Documents 14 to 19 and 29 to 33). Moreover, a method for identifying a protein as a fusion partner for ALK using ALK antibodies has been reported (Non-Patent Document 35). On the other hand, a fusion gene of EML4 and ALK has not been reported. The intracellular localization of these ALK fusion proteins depends on a fusion partner molecule for ALK, and the ALK fusion proteins have been known to exist in cytoplasm, nucleus, and the like. Since most partner molecules have a complex formation domain, the fusion protein itself has been thought to form a complex. This complex formation has been considered to cause loss of control of the tyrosine kinase activity of ALK and induce carcinogenesis with abnormally activated intracellular signals (Non-Patent Document 10). Indeed, it has been reported that the use of ALK shRNA or ALK kinase-inhibiting compound for lymphoma cells expressing ALK fusion proteins can induce cell growth inhibition and cell death. Therefore, it has been suggested that the ALK fusion protein may serve as a therapeutic target for lymphoma and inflammatory myofibroblastic tumor (Non-Patent Documents 20 to 22). It has also been suggested that ALK may serve as a therapeutic target for other cancers whose growth involves ALK as described above (Non-Patent Documents 21 to 22).

Various low-molecular-weight compounds having an inhibitory activity against ALK have been reported so far. Marzec et al. have reported that WHI-P131 and WHI-P154 (both, EMD Biosciences), which have originally been utilized as JAK3 tyrosine kinase-inhibiting substances, inhibit the activity of NPM-ALK (Non-Patent Document 22). Another group has developed their own low-molecular-weight ALK-inhibiting substance and has demonstrated that this inhibitor induces the cell death of NPM-ALK-expressing lymphoma cell lines (Non-Patent Document 21). In addition, plural low-molecular-weight compounds having an inhibitory activity against ALK have been reported so far (Non-Patent Documents 23 and 34 and Patent Documents 1 to 4).

[Patent Document 1] Pamphlet of WO 2005/097765
[Patent Document 2] Pamphlet of WO 2005/009389
[Patent Document 3] Pamphlet of WO 2005/016894
[Patent Document 4] Pamphlet of WO 2004/080980
[Non-Patent Document 1] "The New England journal of medicine", (US), 2005, Vol. 353, p. 172-187
[Non-Patent Document 2] "Science", (US), 2004, Vol. 304, p. 1497-1500
[Non-Patent Document 3] "The New England journal of medicine", (US), 2004, Vol. 350, p. 2129-2139
[Non-Patent Document 4] "Cancer research", (US), 2004, Vol. 64, p. 8919-8923
[Non-Patent Document 5] "Proceedings of the national academy of sciences of the United States of America", (US), 2004, Vol. 101, p. 13306-13311
[Non-Patent Document 6] "Annual review of medicine", (US), 2003, Vol. 54, p. 73-87
[Non-Patent Document 7] "Seminars in oncology", (US), 1993, Vol. 20, p. 105-127
[Non-Patent Document 8] "Genomics", (US), 2000, Vol. 68, p. 348-350
[Non-Patent Document 9] "Experimental cell research", (US), 2006, doi: 10.1016/j.yexcr.2006.06.035
[Non-Patent Document 10] "Cellular and molecular life sciences", (Switzerland), 2004, Vol. 61, p. 2939-2953
[Non-Patent Document 11] "EMBO reports", (UK), 2003, Vol. 4, p. 781-786
[Non-Patent Document 12] "Journal of cellular physiology", (US), 2004, Vol. 199, p. 330-358
[Non-Patent Document 13] "International journal of cancer", (US), 2002, Vol. 100, p. 49-56
[Non-Patent Document 14] "Science", (US), 1994, Vol. 263, p. 1281-1284
[Non-Patent Document 15] "Blood", (US), 1995, Vol. 86, p. 1954-1960
[Non-Patent Document 16] "Blood", (US), 2000, Vol. 95, p. 3204-3207
[Non-Patent Document 17] "Blood", (US), 1999, Vol. 94, p. 3265-3268
[Non-Patent Document 18] "Laboratory investigation; a journal of technical methods and pathology", (US), 2003, Vol. 83, p. 1255-1265
[Non-Patent Document 19] "International journal of cancer", (US), 2006, Vol. 118, p. 1181-1186
[Non-Patent Document 20] "Blood", (US), 2006, Vol. 107, p. 689-697
[Non-Patent Document 21] "Blood", (US), 2006, Vol. 107, p. 1617-1623
[Non-Patent Document 22] "Laboratory investigation; a journal of technical methods and pathology", (US), 2005, Vol. 85, p. 1544-1554
[Non-Patent Document 23] "Journal of medicinal chemistry", (US), 2006, Vol. 49, p. 1006-1015
[Non-Patent Document 24] "Cellular and molecular life sciences", (Switzerland), 2004, Vol. 61, p. 2897-2911
[Non-Patent Document 25] "Science", (US), 1997, Vol. 278, p. 1309-1312
[Non-Patent Document 26] GenBank accession Number: NM 019063
[Non-Patent Document 27] GenBank accession Number: AB209477
[Non-Patent Document 28] Oncogene. 1997 Jan. 30; 14 (4): 439-49
[Non-Patent Document 29] Oncogene 9: 1567-1574, 1994
[Non-Patent Document 30] Am J Pathol 160: 1487-1494, 2002
[Non-Patent Document 31] Am J Pathol 157: 377-384, 2000
[Non-Patent Document 32] Blood 90: 2901-2910, 1997
[Non-Patent Document 33] Am J Pathol. 2000 March; 156 (3): 781-9
[Non-Patent Document 34] J Comb Chem. 8: 401-409, 2006
[Non-Patent Document 35] PNAS 2006 103, 7402-7407

An object of the present invention is to elucidate a polynucleotide as a novel oncogene and thereby provide a method and kit for detecting the polynucleotide, a method for screening a therapeutic agent for cancer, a method for treating cancer, and a therapeutic agent for cancer.

SUMMARY OF THE INVENTION

The present inventors successfully isolated, from samples obtained from lung cancer patients, the cDNA and genomic DNA of a novel fusion polynucleotide of an EML4 gene fused with an ALK gene as kinase (EML4-ALK fusion polynucleotide variant 1; hereinafter, referred to as an EML4-ALK fusion polynucleotide v1), which is produced by chromosomal inversion (Examples 1, 2, and 4(1)). The present inventors also successfully isolated the cDNA and genomic DNA of a novel fusion polynucleotide (EML4-ALK fusion polynucleotide variant 2; hereinafter, referred to as an EML4-ALK fusion polynucleotide v2) whose fused regions are different from those in the EML4-ALK fusion polynucleotide v1 (Examples 4(1) and 3(3)). Analysis using clinical samples showed that the EML4-ALK fusion polynucleotide v1 or EML4-ALK fusion polynucleotide v2 is present in some lung cancer patients (approximately 5% to 10%) (Example 3). On the other hand, since the EML4-ALK fusion polynucleotide is an oncogene that exhibits tumorigenicity depending on its kinase activity (Example 6, 10(3)), it was revealed that the EML4-ALK fusion polypeptide serves as a tool for screening a therapeutic agent for cancer that is shown to be positive for the fusion polynucleotide. Based on these findings, the present inventors constructed a method for detecting the fusion polynucleotide or fusion protein in a sample obtained from a test subject (Examples 3, 4(2), 5(2), and 9) and, subsequently, a method for screening an inhibitor of the fusion polynucleotide and/or the fusion polypeptide (i.e., a therapeutic agent for cancer that is shown to be positive for the fusion polynucleotide) causative of cancer (Examples 7 and 10(2)), and confirmed that compounds obtained by screening exhibit an anti-tumor effect (Examples 8(3), 8(7), and 8(8)).

As a result, a test subject from which the fusion polynucleotide has been detected can receive cancer treatment using the inhibitor of the fusion polynucleotide and/or the polypeptide encoded thereby. According to the detection method, subjects to which the therapeutic agent is applicable can be selected. As a result, tailor-made medical care expected as highly effective treatment using the inhibitor can be carried out.

Based on these findings, the present inventors provided a novel polynucleotide and polypeptide useful as screening tools, a screening method, and a method for treating cancer that is shown to be positive for a fusion gene of EML4 gene and ALK gene. The present inventors completed the present invention by further providing a detection method useful in the detection of cancer that is shown to be positive for the fusion gene of EML4 gene and ALK gene.

Specifically, the present invention relates to:

[1] an isolated polypeptide comprising the amino acid sequence represented by SEQ ID NO: 2 or 7 and having a kinase activity;

[2] the isolated polypeptide according to [1] consisting of the amino acid sequence represented by SEQ ID NO: 2 or 7;

[3] an isolated polynucleotide encoding the polypeptide according to [1];

[4] an expression vector comprising the polynucleotide according to [3];

[5] a cell transformed with the expression vector according to [4];

[6] a method for producing the polypeptide according to [1], comprising culturing a transformed cell according to [5] under conditions suitable for polypeptide expression and collecting the polypeptide from the cell;

[7] a method for detecting a fusion gene of EML4 gene and ALK gene, comprising the step of detecting the presence of the polynucleotide encoding the polypeptide according to [1] in a sample obtained from a test subject;

[8] a method for detecting a fusion protein encoded by a fusion gene of EML4 gene and ALK gene, comprising the step of detecting the presence of the polypeptide according to [1] in a sample obtained from a test subject;

[9] a kit for detection of a fusion gene of EML4 gene and ALK gene, comprising sense and antisense primers designed to specifically amplify a polynucleotide encoding the polypeptide according to [1];

[10] a primer set for detecting a fusion gene of EML4 gene and ALK gene, comprising an antisense primer consisting of a nucleic acid molecule hybridizing under stringent conditions to i) the polynucleotide according to [3], ii) a polynucleotide consisting of the nucleotide sequence represented by SEQ ID NO: 4, and/or iii) a polynucleotide consisting of the nucleotide sequence represented by SEQ ID NO: 5, and a sense primer consisting of nucleic acid molecule hybridizing under stringent conditions to complementary strands to the above i) to iii);

[11] a primer set of a sense primer comprising an oligonucleotide with at least any 16 consecutive bases located at base Nos. 1 to 1759 in SEQ ID NO: 1 and an antisense primer comprising an oligonucleotide complementary to an oligonucleotide with at least any 16 consecutive bases located at base Nos. 1760 to 3926 in SEQ ID NO: 1, or a primer set consisting of complementary strands thereof, wherein the sense and antisense primers give amplification products of 1 kb or less in size;

[12] the primer set of the sense primer and the antisense primer in according [11] selected from a group consisting of (1)-(11) below or complementary strands thereof; (1) SEQ ID NOs: 8 and 9, (2) SEQ ID NOs: 61 and 62, (3) SEQ ID NOs: 63 and 64, (4) SEQ ID NOs: 65 and 66, (5) SEQ ID NOs: 67 and 68, (6) SEQ ID NOs: 69 and 70, (7) SEQ ID NOs: 71 and 72, (8) SEQ ID NOs: 73 and 74, (9) SEQ ID NOs: 75 and 76, (10) SEQ ID NOs: 77 and 78, and (11) SEQ ID NOs: 79 and 80.

[13] a primer set of a sense primer comprising an oligonucleotide with at least any 16 consecutive bases located at base Nos. 1 to 2242 in SEQ ID NO: 6 and an antisense primer comprising an oligonucleotide complementary to an oligonucleotide with at least any 16 consecutive bases located at base Nos. 2243 to 3933 in SEQ ID NO: 6, or a primer set consisting of complementary strands thereof, wherein the sense and antisense primers give amplification products of 1 kb or less in size;

[14] the primer set of the sense primer and the antisense primer in according to [13] selected from a group consisting of (1)-(10) below or complementary strands thereof; (1) SEQ ID NOs: 81 and 82, (2) SEQ ID NOs: 83 and 84, (3) SEQ ID NOs: 85 and 86, (4) SEQ ID NOs: 87 and 88, (5) SEQ ID NOs: 89 and 90, (6) SEQ ID NOs: 91 and 92, (7) SEQ ID NOs: 93 and 94, (8) SEQ ID NOs: 95 and 96, (9) SEQ ID NOs: 97 and 98, and (10) SEQ ID NOs: 99 and 100.

[15] a primer set of a sense primer comprising an oligonucleotide with at least any 16 consecutive bases located at base Nos. 1 to 3629 in SEQ ID NO: 4 and an antisense primer comprising an oligonucleotide complementary to an oligonucleotide with at least any 16 consecutive bases located at base Nos. 3630 to 3979 in SEQ ID NO: 4, or a primer set consisting of complementary strands thereof, wherein the sense and antisense primers give amplification products of 1 kb or less in size;

[16] the primer set of the sense primer and the antisense primer in according to [15] selected from a group consisting of (1)-(10) below or complementary strands thereof; (1) SEQ ID NOs: 15 and 16, (2) SEQ ID NOs: 17 and 18, (3) SEQ ID NOs: 19 and 20, (4) SEQ ID NOs: 21 and 22, (5) SEQ ID NOs: 23 and 24, (6) SEQ ID NOs: 25 and 26, (7) SEQ ID NOs: 27 and 28, (8) SEQ ID NOs: 29 and 30, (9) SEQ ID NOs: 31 and 32, and (10) SEQ ID NOs: 33 and 34.

[17] a primer set of a sense primer comprising an oligonucleotide with at least any 16 consecutive bases located at base Nos. 1 to 579 in SEQ ID NO: 5 and an antisense primer comprising an oligonucleotide complementary to an oligonucleotide with at least any 16 consecutive bases located at base Nos. 580 to 853 in SEQ ID NO: 5, or a primer set consisting of complementary strands thereof;

[18] the primer set of the sense primer and the antisense primer in according to [17] selected from a group consisting of (1)-(11) below or complementary strands thereof; (1) SEQ ID NOs: 35 and 36, (2) SEQ ID NOs: 37 and 38, (3) SEQ ID NOs: 39 and 18, (4) SEQ ID NOs: 41 and 20, (5) SEQ ID NOs: 43 and 22, (6) SEQ ID NOs: 45 and 46, (7) SEQ ID NOs: 47 and 26, (8) SEQ ID NOs: 49 and 28, (9) SEQ ID NOs: 51 and 52, (10) SEQ ID NOs: 53 and 54, and (11) SEQ ID NOs: 55 and 34.

[19] a probe for detecting the polynucleotide of the present invention, comprising a nucleic acid molecule with at least 32 consecutive bases hybridizing under stringent conditions to i) the polynucleotide according to [3], ii) a polynucleotide consisting of the nucleotide sequence represented by SEQ ID NO: 4, iii) a polynucleotide consisting of the nucleotide sequence represented by SEQ ID NO: 5, or iv) complementary strands to the above i) to iii), and comprising positions 1744 to 1775 of the nucleotide sequence represented by SEQ ID NO: 1, positions 2227 to 2258 of the nucleotide sequence represented by SEQ ID NO: 6, positions 3614 to 3645 of the nucleotide sequence represented by SEQ ID NO: 4, positions 564 to 595 of the nucleotide sequence represented by SEQ ID NO: 5; or complementary strands thereof.

[20] a method for screening a substance inhibiting the polypeptide according to [1], comprising the steps of (1) bringing test substances into contact with the polypeptide or a cell expressing the polypeptide, (2) analyzing whether the polypeptide is inhibited or not, and (3) selecting a substance inhibiting the polypeptide;

[21] the screening method according to [20], further comprising the step of confirming that the selected test substance has a therapeutic activity against cancer that is shown to be positive for a fusion gene of EML4 gene and ALK gene;

[22] a method for treating cancer that is shown to be positive for a fusion gene of EML4 gene and ALK gene, comprising administering an effective amount of a substance inhibiting the polypeptide according to [1] to a target in need of treatment of cancer that is shown to be positive for a fusion gene of EML4 gene and ALK gene;

[23] the method for treating cancer that is shown to be positive for a fusion gene of EML4 gene and ALK gene according to [22], wherein the substance inhibiting the polypeptide according to [1] is 5-chloro-$N^4$-[2-(isopropylsulfonyl)phenyl]-$N^2$-{2-methoxy-4-[4-(4-methylpiperazin-1-yl)piperidin-1-yl]phenyl}pyrimidine-2,4-diamine or 2-[(5-bromo-2-{[2-methoxy-4-(4-methylpiperazin-1-yl)phenyl]amino}pyrimidin-4-yl)amino]-N-methylbenzenesulfonamide;

[24] a double-stranded nucleic acid having an inhibitory activity against the expression of the polypeptide according to [1], wherein a double-stranded portion is designed on the basis of bases at positions selected from a group consisting of (1) 1743 to 1761, (2) 1744 to 1762, (3) 1750 to 1768, (4) 1753 to 1771, (5) 1756 to 1774, and (6) 1757 to 1775 in SEQ ID NO: 1; and

[25] a method for treating cancer that is shown to be positive for a fusion gene of EML4 gene and ALK gene, comprising administering an effective amount of the double-stranded nucleic acid according to [24] to a subject in need of treatment of cancer that is shown to be positive for a fusion gene of EML4 gene and ALK gene.

None of above-mentioned documents have reported the formation of a fusion gene by EML4 gene and ALK gene, let alone the expression of the fusion gene of EML4 gene and ALK gene in some cancer patients. The formation of a fusion gene by EML4 gene and ALK gene and the expression of this fusion gene in some cancer patients were found for the first time by the present inventors. The screening method using a fusion gene of EML4 gene and ALK gene is an invention that was made for the first time by the present inventors. Moreover, the method for detecting the fusion gene useful in the detection of cancer that is shown to be positive for a fusion gene, the probe or primer set useful in this detection, and the kit for detection are inventions that were provided for the first time by the findings of the present inventors. Various ALK inhibitors (Patent Documents 3 to 4 and Non-Patent Documents 20 to 22 and 34) including 5-chloro-$N^4$-[2-(isopropylsulfonyl)phenyl]-$N^2$-{2-methoxy-4-[4-(4-methylpiperazin-1-yl)piperidin-1-yl]phenyl}pyrimidine-2,4-diamine and 2-[(5-bromo-2-{[2-methoxy-4-(4-methylpiperazin-1-yl)phenyl]amino}pyrimidin-4-yl)amino]-N-methylbenzenesulfonamide have been reported. Furthermore ALK inhibitors have been reported to induce growth inhibition and cell death in lymphoma cells expressing NPM-ALK fusion proteins (Non-Patent Documents 20 to 22). However, it has totally been unknown that these ALK inhibitors have therapeutic applications for cancer (particularly, lung cancer) that is shown to be positive for a fusion gene of EML4 gene and ALK gene. The method for treating cancer (particularly, lung cancer) that is shown to be positive for a fusion gene of EML4 gene and ALK gene is an invention that was provided for the first time by the findings of the present inventors. A NPM-ALK inhibitor which suppressed lymphomagenesis in ALK-positive ALCL has been reported (PNAS, 2007, Jan. 2, 104 (1), 270-275 Epub2006 December). However this PNAS article is the literature published within one year prior to the date of the present application. The presence of a new type of abnormal kinase found in approximately 10% of lung cancer cases have been reported (Proceedings of the 65th Annual Meeting of the Japanese Cancer Association, 0-324 (issued on Aug. 28, 2006)). EML4-ALK fusion gene and its transforming activity have been reported (Nature 448, 561-566, 2 Aug. 2007 (online on 11 Jul. 2007)). Further, in the Nature article, it has been described that the fusion kinase is a promising candidate for therapeutic target as well as for a diagnostic molecular marker in non-small-cell lung cancer. However, above 0-324 article and the Nature article are the literature published within one year prior to the date of the present application.

The polypeptide, polynucleotide, expression vector, and cell of the present invention can be used in the screening of a substance inhibiting the polypeptide of the present invention (particularly, a therapeutic agent for lung cancer that is shown to be positive for a fusion gene of EML4 gene and ALK gene). Subjects for which a fusion gene of EML4 gene and ALK gene is positive (particularly, lung cancer patients) can be detected by using the presence of the polypeptide and/or polynucleotide of the present invention as an index. According to the screening method of the present invention, a therapeutic agent for cancer (particularly, a therapeutic agent for lung cancer) that is shown to be positive for a fusion gene of EML4 gene and ALK gene can be screened. The probe or primer and kit for detection of the present invention can be utilized for detecting a cancer that is shown to be positive for a fusion gene of EML4 gene and ALK gene. The detection method of the present invention can be utilized as a method for detecting cancer (particularly, lung cancer) that is shown to be positive for the fusion gene of EML4 gene and ALK gene. Moreover, according to the detection method of the present invention, whether or not the therapeutic agent of the present invention is applicable to subjects can be determined. The substance inhibiting the polypeptide of the present invention is useful as a therapeutic agent for cancer, particularly lung cancer, that is shown to be positive for a fusion gene of EML4 gene and ALK gene.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 6(a) shows time dependent change of cell number when respective concentrations of compound A were added to BA/F3 cells expressing only CD8 and cultured in the presence of IL-3. (b) shows time dependent change of cell number when v1 expressing BA/F3 cells were cultured with respective concentration of compound A in the absence of IL-3. The horizontal axis of the figure is time course (Days) and the vertical axis is the cell number; and FIG. 7 shows siRNA1-siRNA9.

DETAILED DESCRIPTION OF THE PREFERRED EMBODIMENTS

Figure 1:
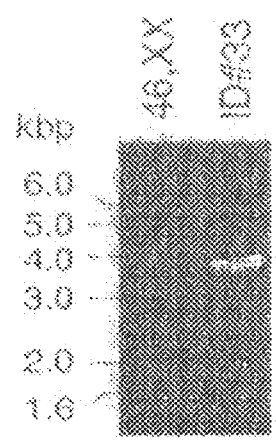
FIG. 1 shows the results of PCR. The left lane (46, XX) shows the result when the genomic DNA from a normal healthy subject was used as a substrate, and the right lane (ID #33) shows the result when the genomic DNA from a cancer patient was used as a substrate.

Hereinafter, the present invention will be described in detail. Gene manipulation techniques described herein can be practiced according to techniques known in the art, such as "Molecular Cloning", Sambrook, J et al., Cold Spring Harbor Laboratory Press, 1989, unless otherwise specified. Protein manipulation techniques described herein can be practiced according to techniques known in the art, such as "Experimental Protocol on Proteins", Shujunsha Co. Ltd. 1997, unless otherwise specified.

The phrase "the polypeptide of the present invention is inhibited" described herein encompasses both the phrases "the expression of the polypeptide of the present invention is inhibited" and "the activity of the polypeptide of the present invention is inhibited". A "substance inhibiting the polypeptide of the present invention" encompasses both a "substance inhibiting the expression of the polypeptide of the present invention" and a "substance inhibiting the activity of the polypeptide of the present invention".

<Polypeptide, Polynucleotide, Expression Vector, Transformed Cell, and Methods for Producing Polypeptide of the Present Invention>

The polypeptide of the present invention encompasses:

(1) a polypeptide consisting of the amino acid sequence represented by SEQ ID NO: 2 or 7; and (2) (a) a polypeptide comprising the amino acid sequence represented by SEQ ID NO: 2 and having a kinase activity (hereinafter, referred to as a v1 functionally equivalent modified polypeptide);

(b) a polypeptide comprising the amino acid sequence represented by SEQ ID NO: 7 and having a kinase activity (hereinafter, referred to as a v2 functionally equivalent modified polypeptide);

(hereinafter, the v1 functionally equivalent modified polypeptide and v2 functionally equivalent modified polypeptide are collectively referred to as a functionally equivalent modified polypeptide).

The phrase "having a kinase activity" means having an activity as an enzyme phosphorylating tyrosine. Whether a certain polypeptide "has a kinase activity" is confirmed by a method of Example 7(2).

Up to this point, the polypeptide of the present invention has been described. Hereinafter, the polypeptide consisting of the amino acid sequence represented by SEQ ID NO: 2 or 7, and the functionally equivalent modified polypeptide are collectively referred to as a "polypeptide of the present invention". Of the polypeptides of the present invention, the polypeptide consisting of the amino acid sequence represented by SEQ ID NO: 2, and the v1 functionally equivalent modified polypeptide are collectively referred to as a "polypeptide type v1 of the present invention". The polypeptide consisting of the amino acid sequence represented by SEQ ID NO: 7, and the v2 functionally equivalent modified polypeptide are collectively referred to as a "polypeptide type v2 of the present invention". A protein as the polypeptide consisting of the amino acid sequence represented by SEQ ID NO: 2 is referred to as an "EML4-ALK fusion polypeptide v1". A protein as the polypeptide consisting of the amino acid sequence represented by SEQ ID NO: 7 is referred to as "an EML4-ALK fusion polypeptide v2". The "EML4-ALK fusion polypeptide v1" and the "EML4-ALK fusion polypeptide v2" are collectively referred to as an "EML4-ALK fusion polypeptide".

The polypeptide of the present invention is, preferably, the "polypeptide consisting of the amino acid sequence represented by SEQ ID NO: 2 or 7", or the "polypeptide comprising the amino acid sequence represented by SEQ ID NO: 2 or 7 and having a kinase activity", more preferably, the "polypeptide consisting of the amino acid sequence represented by SEQ ID NO: 2 or 7".

A polynucleotide encoding the polypeptide of the present invention (hereinafter, referred to as a "polynucleotide of the present invention") is a polynucleotide represented by a nucleotide sequence encoding the EML4-ALK fusion polypeptide, or functionally equivalent modified polypeptide. The polynucleotide of the present invention is, preferably, a polynucleotide consisting of a nucleotide sequence encoding the amino acid sequence represented by SEQ ID NO: 2 or 7, more preferably, a polynucleotide consisting of the nucleotide sequence represented by SEQ ID NO: 1 (particularly preferably, positions 271 to 3447 in SEQ ID NO: 1) or 6.

Of the polynucleotides of the present invention, a gene encoding the polypeptide type v1 of the present invention is referred to as a "polynucleotide type v1 of the present invention". A gene encoding the polypeptide type v2 of the present invention is referred to as a "polynucleotide type v2 of the present invention".

A "fusion gene of EML4 gene and ALK gene" described herein refers to the polynucleotide of the present invention. A gene encoding the EML4-ALK fusion polypeptide v1, which is a polynucleotide type v1 of the present invention, is referred to as an "EML4-ALK fusion polynucleotide v1". A gene encoding the EML4-ALK fusion polypeptide v2, which is a polynucleotide type v2 of the present invention, is referred to as an "EML4-ALK fusion polynucleotide v2". The EML4-ALK fusion polynucleotides v1 and v2 are collectively referred to as an "EML4-ALK fusion polynucleotide".

The phrase "cancer that is shown to be positive for a fusion gene of EML4 gene and ALK gene" described herein means cancer positive for the polynucleotide of the present invention (i.e., the polynucleotide of the present invention is present) and, preferably, means cancer positive for the EML4-ALK fusion polynucleotide (i.e., the EML4-ALK fusion polynucleotide is present). Among "cancer that is shown to be positive for a fusion gene of EML4 gene and ALK gene" described herein, the EML4-ALK fusion polynucleotide-positive cancer is preferable.

Examples of a method for producing the polynucleotide of the present invention can include, but not particularly limited to, (1) a method using polymerase chain reaction (PCR), (2) a method using a standard genetic engineering approach (i.e., a method comprising selecting a transformed strain comprising desired amino acid sequence from strains transformed with a cDNA library), and (3) a chemical synthesis method. Each production method can be practiced in the same way as in WO 01/34785. However, the "novel protein of the present invention" described therein can be interpreted as a protein consisting of the polypeptide of the present invention described herein, and the "gene of the present invention" described therein can be interpreted as the polynucleotide of the present invention described herein.

In the method using PCR, the polynucleotide of the present invention can be produced, for example, according to procedures described in 1) Production method of protein gene, a) First production method in "Embodiments of the Invention" of the patent document. mRNA is extracted from cells or tissues having the ability to produce the protein of the present invention, for example, from lung tissues derived from a human patient with lung cancer. Subsequently, this mRNA can be subjected to reverse transcriptase reaction in the presence of random primers or oligo dT primers to synthesize single-stranded cDNA. The obtained single-stranded cDNA can be subjected to PCR using 2 primers interposing a partial region of the gene of interest to obtain the polynucleotide of the present invention or a portion thereof. More specifically, the polynucleotide of the present invention can be produced, for example, by a method described in Example 4(1).

Alternatively, the polynucleotide of the present invention may be produced by artificially synthesizing the polynucleotide of the present invention as separated fragments by reverse transcription (RT)-PCR and then fusing these obtained fragments. For example, (a) 1489 bases located from the initiation codon (ATG) of exon 1 to exon 13 in EML4 (for the polynucleotide type v1 of the present invention) or 2242 bases located from the initiation codon of exon 1 to exon 20 in EML4 (for the polynucleotide type v2 of the present invention) are amplified by RT-PCR using, as a template, mRNA extracted from cells (e.g., HeLa cells) or tissues endogenously expressing EML4 and using 2 primers interposing the gene region of interest. On the other hand, for example, (b) 1691 bases located from exon 21 to stop codon (TGA) in ALK (for both the polynucleotide type v1 of the present invention and the polynucleotide type v2 of the present invention) are amplified by RT-PCR using, as a template, mRNA extracted from cells (e.g., Rh30 or U-87MG cells) or tissues endogenously expressing ALK and using 2 primers interposing the gene region of interest. The amplified PCR products of (a) and (b) can be fused to obtain the polynucleotide of the present invention. This fusion can be practiced by devising the primers used in the RT-PCR of (a) and (b). For example, a primer is created by adding approximately 10 bases of the 5'-terminal antisense nucleotide sequence of exon 21 in ALK to the 5' terminus of an antisense primer for the RT-PCR amplification of the fragment of (a), and this created primer is used as an antisense primer to amplify the fragment of (a). Moreover, a primer is created by adding approximately 10 bases of the 3'-terminal sense nucleotide sequence of exon 13 in EML4 (for the polynucleotide type v1 of the present invention) or approximately 10 bases of the 3'-terminal sense nucleotide sequence of exon 20 in EML4 (for the polynucleotide type v2 of the present invention) to the 5' terminus of a sense primer for the RT-PCR amplification of the fragment of (b), and this created primer is used as a sense primer to amplify the fragment of (b). The polynucleotide of the present invention can be obtained by PCR using, as templates, these 2 kinds of PCR products obtained and using a sense primer comprising the initiation codon of EML4 and an antisense primer comprising the stop codon of ALK. Alternatively, the polynucleotide of the present invention can also be obtained by annealing and extension reactions using only these 2 kinds of PCR products obtained without using the sense primer comprising the initiation codon of EML4 and the antisense primer comprising the stop codon of ALK.

In the method using a standard genetic engineering approach, the polynucleotide of the present invention can be produced, for example, according to procedures described in 1) Production method of protein gene, b) Second production method in "Mode for Carrying Out the Invention" of WO 01/34785.

In the method using a chemical synthesis method, the polynucleotide of the present invention can be produced, for example, according to procedures described in 1) Production method of protein gene, c) Third production method and d) Fourth production method in "Mode for Carrying Out the Invention" of WO 01/34785. More specifically, the polynucleotide of the present invention can also be produced by binding nucleotide fragments produced by the chemical synthesis method. Alternatively, each polynucleotide oroligonucleotide can be synthesized with a DNA synthesizer (e.g., Oligo 1000M DNA Synthesizer (Beckman) or 394 DNA/RNA Synthesizer (Applied Biosystems).

The expression vector of the present invention, transformed cell of the present invention, and method for producing polypeptide of the present invention can be practiced, for example, according to procedures described in 2) Methods for the production of the vector of the invention, the host cell of the invention and the recombinant protein of the invention in "Mode for Carrying Out the Invention" of WO 01/34785. The isolated polynucleotide of the present invention can be incorporated again into appropriate vector DNA to thereby transform a eukaryotic or prokaryotic host cell therewith. Alternatively, an appropriate promoter and a sequence involved in phenotypic expression may be introduced to the vector to thereby cause each host cell transformed therewith to express the polynucleotide.

The expression vector of the present invention is not particularly limited as long as it comprises the polynucleotide of the present invention and it expresses the polypeptide of the present invention. Examples thereof can include an expression vector obtained by inserting the polynucleotide of the present invention into an expression vector known in the art, which is appropriately selected according to a host cell used.

Likewise, the cell of the present invention is not particularly limited as long as it comprises the polynucleotide of the present invention as a result of nucleic acid transfer by transfection or infection with the expression vector of the present invention. For example, the cell of the present invention can be a host cell comprising the polynucleotide of the present invention incorporated in the chromosome or can be a cell comprising the expression vector comprising the polynucleotide of the present invention. Moreover, the original cell that undergoes nucleic acid transfer can be a cell expressing the polypeptide of the present invention or can be a cell not expressing the polypeptide of the present invention. The cell of the present invention can be obtained, for example, by transfecting or infecting a desired cell with the expression vector of the present invention. More specifically, for example, the polynucleotide of the present invention can be incorporated to an expression vector for mammalian cells to thereby obtain an expression vector of the desired protein. This expression vector can be taken up into a cell by use of a commercially available transfection reagent Lipofectamine to thereby produce the transformed cell of the present invention. Alternatively, for example, the expression vector comprising the polynucleotide of the present invention and a plasmid for packaging (e.g., pGP or pE-eco) can be introduced into a BOSC23 cell by use of a commercially available transfection reagent Lipofectamine, as described in Example 1, to thereby produce an expression retrovirus. A BA/F3 cell can be infected with this retrovirus to thereby produce the transformed cell of the present invention.

The desired transformed cell thus obtained can be cultured according to a standard method. A protein consisting of the polypeptide of the present invention is produced by this culture. A medium used in the culture can be selected appropriately according to a host cell used from among a variety of routine media. For example, an RPMI1640 medium supplemented with serum components such as fetal bovine serum (FBS) can be used for the BA/F3 cell.

The polypeptide of the present invention thus produced by the transformed cell can be separated and purified by a variety of separation operation techniques known in the art using the physical or biochemical properties of the polypeptide.

The polypeptide of the present invention can be fused in frame with a marker sequence and expressed to thereby achieve the confirmation of expression of the protein as well as the purification of the protein. Examples of the marker sequence include FLAG epitope, Hexa-Histidine tag, Hemagglutinin tag, and myc epitope. Alternatively, a specific amino acid sequence recognizable by protease such as enterokinase, factor Xa, or thrombin can be inserted between the marker sequence and the polypeptide of the present invention to thereby remove the marker sequence portion by cleavage with the protease.

The polynucleotide of the present invention can be used as a control template for reaction in the detection method using PCR and is useful in the determination of a subject for which the polynucleotide of the present invention is positive. Moreover, the polypeptide of the present invention can be used as a control for detecting and quantifying expression levels.

<Probe or Primer of the Present Invention>

The present invention encompasses a probe or primers useful in the detection of the presence of the polynucleotide of the present invention.

Specifically, the present invention encompasses:

(1) a primer set for detecting the polynucleotide of the present invention, comprising nucleic acid molecules with at least 16 consecutive bases hybridizing under stringent conditions (preferably, more stringent conditions) to a polynucleotide type v1 of the present invention (preferably, aEML4-ALK fusion polynucleotide v1, more preferably, a polynucleotide consisting of the nucleotide sequence represented by SEQ ID NO: 1), a polynucleotide type v2 of the present invention (preferably, a EML4-ALK fusion polynucleotide v2, more preferably, a polynucleotide consisting of the nucleotide sequence represented by SEQ ID NO: 6), a polynucleotide consisting of the nucleotide sequence represented by SEQ ID NO: 4, which is one of sequences comprising the fusion point of a polynucleotide belonging to EML4-ALK fusion polynucleotide v1, and/or a polynucleotide consisting of the nucleotide sequence represented by SEQ ID NO: 5, which is one of sequences comprising the fusion point of a polynucleotide belonging to EMK4-ALK fusion polynucleotide v2, or complementary strands thereof;

(2) a probe for detecting the polynucleotide of the present invention, comprising a nucleic acid molecule with at least 32 consecutive bases hybridizing under stringent conditions (preferably, more stringent conditions) to a polynucleotide type v1 of the present invention (preferably, aEML4-ALK fusion polynucleotide v1, more preferably, a polynucleotide consisting of the nucleotide sequence represented by SEQ ID NO: 1), a polynucleotide encoding the polypeptide type v2 of the present invention (preferably, aEML4-ALK fusion polynucleotide v2, more preferably, a polynucleotide consisting of the nucleotide sequence represented by SEQ ID NO: 6), a polynucleotide consisting of the nucleotide sequence represented by SEQ ID NO: 4, which is one of sequences comprising the fusion point of a polynucleotide belonging to EML4-ALK fusion polynucleotide v1, a polynucleotide consisting of the nucleotide sequence represented by SEQ ID NO: 5, which is one of sequences comprising the fusion point of a polynucleotide belonging to EMK4-ALK fusion polynucleotide v2; or complementary strands thereof, and comprising positions 1744 to 1775 of the nucleotide sequence represented by SEQ ID NO: 1, positions 2227 to 2258 of the nucleotide sequence represented by SEQ ID NO: 6, positions 3614 to 3645 of the nucleotide sequence represented by SEQ ID NO: 4, positions 564 to 595 of the nucleotide sequence represented by SEQ ID NO: 5; or complementary strands thereof (preferably, positions 1742 to 1777 of the nucleotide sequence represented by SEQ ID NO: 1, positions 2225 to 2260 of the nucleotide sequence represented by SEQ ID NO: 6, positions 3612 to 3647 of the nucleotide sequence represented by SEQ ID NO: 4, or positions 562 to 597 of the nucleotide sequence represented by SEQ ID NO: 5, particularly preferably, positions 1740 to 1779 of the nucleotide sequence represented by SEQ ID NO: 1, positions 2223 to 2262 of the nucleotide sequence represented by SEQ ID NO: 6, positions 3610 to 3649 of the nucleotide sequence represented by SEQ ID NO: 4, or positions 560 to 599 of the nucleotide sequence represented by SEQ ID NO: 5; or complementary strands thereof);

(3) a primer set of a sense primer comprising an oligonucleotide with at least any 16 consecutive bases located at base Nos. 1 to 1759 (preferably, base Nos. 271 to 1759) in SEQ ID NO: 1 and an antisense primer comprising an oligonucleotide complementary to an oligonucleotide with at least any 16 consecutive bases located at base Nos. 1760 to 3926 (preferably, base Nos. 1760 to 3447) in SEQ ID NO: 1, or a primer set consisting of complementary strands thereof, wherein the spacing between the selected positions of the sense and antisense primers in SEQ ID NO: 1 is 1 kb or less, or wherein the sense and antisense primers give amplification products of 1 kb or less in size;

(4) a primer set of a sense primer comprising an oligonucleotide with at least any 16 consecutive bases located at base Nos. 1 to 2242 in SEQ ID NO: 6 and an antisense primer comprising an oligonucleotide complementary to an oligonucleotide with at least any 16 consecutive bases located at base Nos. 2243 to 3933 in SEQ ID NO: 6, or a primer set consisting of complementary strands thereof, wherein the spacing between the selected positions of the sense and antisense primers in SEQ ID NO: 6 is 1 kb or less, or wherein the sense and antisense primers give amplification products of 1 kb or less in size;

(5) a primer set of a sense primer comprising an oligonucleotide with at least any 16 consecutive bases located at base Nos. 1 to 3629 in SEQ ID NO: 4 and an antisense primer comprising an oligonucleotide complementary to an oligonucleotide with at least any 16 consecutive bases located at base Nos. 3630 to 3979 in SEQ ID NO: 4, or a primer set consisting of complementary strands thereof, wherein the spacing between the selected positions of the sense and antisense primers in SEQ ID NO: 4 is 1 kb or less, or wherein the sense and antisense primers give amplification products of 1 kb or less in size; and (6) a primer set of a sense primer comprising an oligonucleotide with at least any 16 consecutive bases located at base Nos. 1 to 579 in SEQ ID NO: 5 and an antisense primer comprising an oligonucleotide complementary to an oligonucleotide with at least any 16 consecutive bases located at base Nos. 580 to 853 in SEQ ID NO: 5, or a primer set consisting of complementary strands thereof. Examples of a preferable primer set include:

(7) the primer set or the primer set consisting of complementary strands thereof according to any of (3) to (6), wherein the sense and antisense primers are represented by (i) SEQ ID NOs: 8 and 9, (ii) SEQ ID NOs: 15 and 16, 17 and 18, 19 and 20, 21 and 22, 23 and 24, 25 and 26, 27 and 28, 29 and 30, 31 and 32, or 33 and 34, (iii) SEQ ID NOs: 35 and 36, 37 and 38, 39 and 18, 41 and 20, 43 and 22, 45 and 46, 47 and 26, 49 and 28, 51 and 52, 53 and 54, or 55 and 34, (iv) SEQ ID NOs: 61 and 62, 63 and 64, 65 and 66, 67 and 68, 69 and 70, 71 and 72, 73 and 74, 75 and 76, 77 and 78, or 79 and 80, or (v) SEQ ID NOs: 81 and 82, 83 and 84, 85 and 86, 87 and 88, 89 and 90, 91 and 92, 93 and 94, 95 and 96, 97 and 98, or 99 and 100.

The primer sets (7) (i) (in Example 3(1)), (7) (ii) (in Example 3(2)), (7) (iii) (in Example 3(3)), and (7) (iv) and (v) (in Example 4(2)) were used for detecting the presence of the polynucleotide of the present invention.

Fusion point in this specification means a point where a portion derived from EML4 gene and a portion derived from ALK gene are fused. Fusion point in SEQ ID No: 1 is the point where a nucleotide of base position 1759 and a nucleotide of base position 1760 are fused. Fusion point in SEQ ID No: 6 is the point where a nucleotide of base position 2242 and a nucleotide of base position 2243 are fused. Fusion point in SEQ ID No: 4 is the point where a nucleotide of base position 3629 and a nucleotide of base position 3630 are fused. Fusion point in SEQ ID No: 5 is the point where a nucleotide of base position 579 and a nucleotide of base position 580 are fused.

The "stringent conditions" comprise hybridization conditions on the order of "5×SSPE, 5×Denhardt's solution, 0.5% SDS, 50% formamide, 200 μg/ml salmon sperm DNA, 42° C. overnight" and washing conditions on the order of "0.5×SSC, 0.1% SDS, 42° C.". The "more stringent conditions" comprise hybridization conditions on the order of "5×SSPE, 5×Denhardt's solution, 0.5% SDS, 50% formamide, 200 μg/ml salmon sperm DNA, 42° C. overnight" and washing conditions on the order of "0.2×SSC, 0.1% SDS, 65° C.".

The probe or primers of the present invention can be utilized as a probe for detecting and isolating the polynucleotide of the present invention or as primers for amplifying the polynucleotide of the present invention. For primer use, its chain length is usually 15 to 40 bases, preferably 16 to 24 bases, more preferably 18 to 24 bases, particularly preferably 20 to 24 bases. Alternatively, for probe use, the DNA is at least 32 bases, more preferably, at least 36 bases, particularly preferably, at least 40 bases or longer, in chain length.

Methods for producing the probe and primers of the present invention are not particularly limited. The probe and primers of the present invention can be produced by the chemical synthesis method used for the method for producing the polynucleotide of the present invention.

Based on the present invention, an array of oligonucleotide probes comprising the nucleotide sequence of the polynucleotide of the present invention or a fragment thereof can be constructed. The array technique is known in the art and has been used for analyzing gene expression (Chee, M. et al. (1996) Science, 274, 610-613).

<Detection Method and Kit for Detection of the Present Invention>

The present invention encompasses a method for detecting the polynucleotide of the present invention and a method for detecting a fusion protein consisting of the polypeptide of the present invention. The EML4-ALK fusion polynucleotide was found in some human patients with cancer (specifically, non-small cell lung cancer). Therefore, cancer (preferably, lung cancer) that is shown to be positive for the polynucleotide of the present invention can be detected by utilizing the presence of this fusion polynucleotide. Specifically, an aspect comprising the step below is exemplified. Specifically, the method for detecting the polynucleotide of the present invention comprises the step of (1) detecting the presence of the polynucleotide of the present invention in a sample obtained from a test subject.

A sample collected from a test subject (a sample separated from the body), specifically, any collected body fluid (preferably, blood), bronchoalveolar lavage fluid, biopsied sample, or sputum sample is used as the sample obtained from a test subject. Preferably, a biopsy sample of the affected part of the lung of the test subject or a sputum sample of the test subject is used. Genomic DNA extracted from the sample or a transcription product (product as a result of transcription and translation of the genome; e.g., mRNA, cDNA, or a protein) thereof can be used. Particularly preferably, mRNA or cDNA is prepared for use.

In the method for detecting the polynucleotide of the present invention, the "step of detecting the presence of the polynucleotide" may be practiced by detecting the presence of the polynucleotide represented by SEQ ID NO: 4 (genomic sequence comprising the fusion point) or SEQ ID NO:5 (genomic sequence comprising the fusion point) in the genome of the sample obtained from a test subject or detecting the presence of mRNA or cDNA corresponding to the polynucleotide type v1 of the present invention (preferably, the EML4-ALK fusion polynucleotide v1) or the polynucleotide type v2 of the present invention (preferably, the EML4-ALK fusion polynucleotide v2) by preparing a transcription product (e.g., mRNA or cDNA) of genomic DNA extracted from the sample obtained from a test subject.

The genomic DNA extraction can be performed by a method known in the art and can be performed conveniently with a commercially available DNA extraction kit. Examples of the commercially available DNA extraction kit include, but not limited to, G-DEX™ genomic DNA extraction kit (Cosmo Bio Co., Ltd.) and Get pure DNA Kit-Cell, Tissue (Dojindo Co., Ltd.).

The detection step at the step (1) can be practiced according to a gene analysis method known in the art (e.g., PCR commonly used as a gene detection method, LCR (Ligase chain reaction), SDA (Strand displacement amplification), NASBA (Nucleic acid sequence-based amplification), ICAN (Isothermal and chimeric primer-initiated amplification of nucleic acids), LAMP (Loop-mediated isothermal amplification), TMA (Gen-Probe's TMA system), and well known methods such as a microarray). For example, a hybridization technique using, as a probe, a nucleic acid hybridizing to the polynucleotide of the present invention or a gene amplification technique using, as primers, DNAs hybridizing to the polynucleotide of the present invention is utilized. Specifically, a nucleic acid, for example, mRNA, derived from the sample obtained from a test subject is used for measurement. The mRNA level is measured by a gene amplification reaction method using primers designed to specifically amplify the polynucleotide sequence of the present invention. The gene amplification reaction method is not particularly limited. For example, PCR or nucleic acid amplification using RNA polymerase can be utilized. Primers used in the detection method of the present invention or primers contained in the kit for detection of the present invention are not particularly limited as long as they can specifically amplify the polynucleotide sequence of the present invention. These primers are designed on the basis of the nucleotide sequence of the polynucleotide of the present invention. Primer design for a PCR amplification monitoring method can be achieved by utilizing primer design software Primer Express (PE Biosystems). PCR products with a large size reduce amplification efficiency. Therefore, it is appropriate that sense and antisense primers should be designed to give amplification products of 1 kb or less in size in the amplification of mRNA or cDNA. More specifically, a sense primer (5'-primer) and an antisense primer (3'-primer) are designed from an EML4-encoding portion (e.g., any portion within the EML4 gene region of the EML4-ALK fusion polynucleotide (particularly, cDNA)) and from an ALK-encoding portion (e.g., any portion within the ALK gene region of the EML4-ALK fusion polynucleotide (particularly, cDNA)), respectively. Preferably, primers contained in the kit for detection of the present invention, more preferably, most suitable primers contained in the kit for detection of the present invention, are used. Whether the gene of interest (the whole sequence or its specific portion) is amplified or not can be confirmed by a method suitable for each amplification technique. For example, for PCR, the PCR products can be subjected to analysis by agarose gel electrophoresis and ethidium bromide staining to thereby confirm whether an amplification fragment with the size of interest is obtained or not. If the amplification fragment with the size of interest is obtained, then the polynucleotide of the present invention is present in the sample obtained from a test subject. In this way, the presence of the polynucleotide of the present invention can be detected.

Detection using the hybridization technique is performed, for example, by a northern hybridization, dot-blot, or DNA microarray method. Furthermore, a gene amplification technique such as RT-PCR can be utilized. In the RT-PCR method, the presence of the polynucleotide of the present invention can be analyzed more quantitatively by using a PCR amplification monitoring (real-time PCR) method (Genome Res., 6 (10), 986, 1996) in the gene amplification process. For example, ABI PRISM 7900 (PE Biosystems) can be used as the PCR amplification monitoring method. The real-time PCR is a method known in the art and can be performed conveniently by utilizing a commercially available apparatus and a kit for real-time PCR.

The EML4 gene and ALK gene are distantly positioned on the chromosome in opposite orientations. If the EML4-ALK fusion polynucleotide is absent, therefore, RT-PCR using the primers designed for the respective genes does not produce PCR products. Specifically, PCR, even if performed by increased cycles, does not amplify products in normal cells free from chromosomal inversion between both the genes and in cases of cancer (e.g., lung cancer) free from EML4-ALK inversion. Thus, cells or tissues having the polynucleotide of the present invention can be detected with exceeding sensitivity and with few false positives by PCR using the primer set and using genomic DNA, mRNA, or cDNA as a substrate.

A method for detecting a fusion protein encoded by the polynucleotide of the present invention comprises the step of (2) detecting the presence of the polypeptide of the present invention in a sample obtained from a test subject.

Such a detection step can be practiced by preparing a solubilized solution derived from a sample obtained from a test subject (e.g., a cancer tissue or cell obtained from the test subject) and detecting the polypeptide of the present invention (particularly, the EML4-ALK fusion polypeptide v1) contained therein by an immunological measurement or enzyme activity measurement method using anti-EML4 and anti-ALK antibodies in combination. Preferably, a qualitative or quantitative approach using a monoclonal or polyclonal antibody specific to the polypeptide of the present invention (particularly, the EML4-ALK fusion polypeptide v1) can be used, such as enzyme immunoassay, two-antibody sandwich ELISA, fluoroimmunoassay, radioimmunoassay, or western blotting.

More preferably, the presence of the polypeptide of the present invention can be detected, as shown in Example 9, by subjecting cell extracts from a cell likely to have the polypeptide of the present invention to immunoprecipitation with an anti-EML4 antibody and performing detection using an anti-ALK antibody for the precipitates. In the method of Example 9, immunoprecipitation with the anti-ALK antibody and detection with the anti-EML4 antibody may also be used. After the immunoprecipitation and detection thus performed, it is preferred to further confirm that the protein detected by the detection antibody has the size of the polypeptide of the present invention of interest. Even if cell extracts of tissues or cells free from the polypeptide of the present invention are subjected to immunoprecipitation and detection using those 2 antibodies, the polypeptide of the present invention is not detected therein. The antibodies used in this detection may be any antibody that can specifically bind to a polypeptide sequence from exon 1 to exon 20 (preferably, from exon 1 to exon 13) of EML4 or a polypeptide sequence from exon 21 to exon 30 of ALK, and may be monoclonal or polyclonal antibodies.

If the polynucleotide of the present invention or the polypeptide of the present invention (particularly, the EML4-ALK fusion polypeptide v1) is detected from the sample obtained from a test subject, the test subject is a target (patient) having cancer that is shown to be positive for the polynucleotide of the present invention and serves as a target to which the pharmaceutical composition of the present specification is applicable.

The kit for detection of the present invention comprises at least sense and antisense primers designed to specifically amplify the polynucleotide of the present invention (preferably, the EML4-ALK fusion polynucleotide). The set of sense and antisense primers are polynucleotides that function as primers for amplification of the polynucleotide of the present invention (preferably, the EML4-ALK fusion polynucleotide). Examples thereof include the primers (1) and (3) to (7) described in the paragraph <Probe or primer of the present invention>. Most preferable primers are the primers (7).

Examples of other reagents that can be contained in the kit for detection of the present invention can include reagents (e.g., Taq polymerase, nucleotide substrates, and buffer solutions) necessary for PCR.

<Screening Method of the Present Invention>

The screening method of the present invention encompasses a method for screening a substance inhibiting the polypeptide of the present invention and a method for screening a therapeutic agent for cancer (preferably, lung cancer) that is shown to be positive for the polynucleotide of the present invention.

(1) Method for screening a substance inhibiting the polypeptide of the present invention (inhibiting the activity and/or expression of the polypeptide of the present invention)

The method for screening a substance inhibiting the polypeptide of the present invention (preferably, the EML4-ALK fusion polypeptide v1 or the EML4-ALK fusion polypeptide v2) is not particularly limited as long as it comprises the following steps (i) to (iii):

(i) bringing test substances into contact with the polypeptide of the present invention or a cell expressing the polypeptide of the present invention;

(ii) analyzing whether the polypeptide is inhibited or not, and (iii) selecting a substance inhibiting the polypeptide.

If desired, the method for screening a substance inhibiting the polypeptide of the present invention may further comprise the step of confirming that the selected test substance has a therapeutic activity against cancer that is shown to be positive for the polynucleotide of the present invention.

Preferably, the substance inhibiting the polypeptide of the present invention can be screened by methods described in Examples 7(3), 7(4), 8(5), 8(6), 8(3), 8(7), 8(8), and 8(9).

(2) Method for screening a therapeutic agent for cancer (preferably, lung cancer) that is shown to be positive for the polynucleotide of the present invention.

As shown in Examples below (Example 6(1)), a transformed focus, a feature of cancer cells, was formed by causing a 3T3 normal cell to express the EML4-ALK fusion polynucleotide v1. When this cell was subcutaneously inoculated into a nude mouse, tumor was formed, showing that the EML4-ALK fusion polynucleotide v1 is an oncogene. Alternatively, similar analysis using a variety of mutants (Example 6(2)) and analysis of transformability and tumorigenicity (Example 10(3)) showed that the EML4-ALK fusion polynucleotide v2 is also an oncogene. Furthermore, the presence of the EML4-ALK fusion polynucleotide was detected in some lung cancer patients.

Thus, the therapeutic agent for cancer (preferably, lung cancer) that is shown to be positive for the polynucleotide of the present invention can be screened by selecting a substance inhibiting the polypeptide of the present invention. From the novel findings gained by the present inventors that the anchorage-independent cell growth was inhibited (i.e., an anti-cancer effect is exhibited) by inhibiting the activity and/or expression of the polypeptide of the present invention (Example 8), it was shown that the substance inhibiting the polypeptide of the present invention (inhibiting the activity and/or expression of the polypeptide of the present invention) has a therapeutic effect on cancer. Specifically, the method for screening a substance inhibiting the polypeptide of the present invention (inhibiting the activity and/or expression of the polypeptide of the present invention) can be utilized as a method for screening a therapeutic agent for cancer (preferably, lung cancer) that is shown to be positive for the polynucleotide of the present invention.

The substance obtained by the screening method (i) to (iii) can be subjected to an evaluation system known in the art about therapeutic agents for cancer or a modified evaluation system thereof to determine whether or not the substance is useful as a therapeutic agent for cancer. For example, a therapeutic effect on cancer that is shown to be positive for the polynucleotide of the present invention can be confirmed and determined on the basis of the inhibitory effect of the inhibiting substance on the anchorage-independent growth of a cell expressing the polynucleotide of the present invention or on the basis of the inhibitory effect of the inhibiting substance on the growth of tumor formed in a nude mouse inoculated with a cell expressing the polynucleotide of the present invention. Alternatively, the substance obtained by the screening method can be subjected to an evaluation system similar to that for the therapeutic effect using a lung cancer cell expressing the polynucleotide of the present invention to thereby determine whether or not the substance is useful as a therapeutic agent for lung cancer that is shown to be positive for the polynucleotide of the present invention.

The screening method of the present invention encompasses the following methods:

(a) In Vitro Screening Method;

a method for screening a substance inhibiting the activity of the polypeptide of the present invention, comprising the steps of (1) bringing test substances into contact with the polypeptide of the present invention, (2) analyzing whether the activity of the polypeptide is inhibited or not, and (3) selecting a substance inhibiting the activity of the polypeptide;

(b) Cell-Based Screening Method;

a method for screening a substance inhibiting the activity of the polypeptide of the present invention, comprising the steps of (1) bringing test substances into contact with a cell expressing the polypeptide of the present invention, (2) analyzing whether the activity of the polypeptide is inhibited or not, and (3) selecting a substance inhibiting the activity of the polypeptide; and (c) Expression Inhibition-Based Screening Method;

a method for screening a substance inhibiting the expression of the polypeptide of the present invention, comprising the steps of (1) bringing test substances into contact with a cell expressing the polypeptide of the present invention, (2) analyzing whether the expression of the polypeptide is inhibited or not, and (3) selecting a substance inhibiting the expression of the polypeptide.

Each screening method will be described below.

<In Vitro Screening Method>

The in vitro screening method comprises: bringing test substances into contact with the purified polypeptide of the present invention by addition (contact step); analyzing whether the activity of the polypeptide of the present invention is inhibited or not by the test substance(s), by comparison with the activity of the polypeptide of the present invention not brought into contact with the test substances (analysis step); and selecting a substance inhibiting the activity of the polypeptide of the present invention (i.e., a therapeutic agent for cancer, particularly, a therapeutic agent for lung cancer).

In the screening method of the present invention, each step can specifically be practiced, for example, as described below. The polypeptide of the present invention is expressed in cells (e.g., BA/F3 cells). The expressed polypeptide is isolated and purified from the cells by affinity purification using affinity for a tag such as GST, Flag, or His or by immunoprecipitation using an antibody responding to the polypeptide of the present invention (e.g., an anti-EML4, anti-ALK, or tag antibody). Subsequently, test substances are brought into contact with the purified polypeptide by addition. After the addition of ATP, the activity of the polypeptide is measured. Solvents (e.g., DMSO) for the test substances are brought as a control into contact with the purified polypeptide by mixing. After the addition of ATP, the activity of the polypeptide is measured. A condition without the addition of ATP can be set as a background control. Whether the activity (i.e., phosphorylating activity) of the polypeptide of the present invention is inhibited or not by the test substance (s) is analyzed. Whether the activity (i.e., phosphorylating activity) of the polypeptide of the present invention is inhibited or not by the test substance(s) can be determined by analyzing a test substance-induced change in the tyrosine phosphorylation level of the polypeptide of the present invention. Specifically, when the addition (i.e., contact) of a test substance inhibits the activity (i.e., phosphorylating activity) of the polypeptide of the present invention as compared with the addition (i.e., contact) of the solvent control, this test substance is selected as a substance inhibiting the activity of the polypeptide of the present invention (i.e., a therapeutic agent for cancer, particularly, a therapeutic agent for lung cancer). Of the screening methods of the present invention, preferably, the in vitro screening method is practiced under the conditions described in Example 7(3). A substance that can inhibit 50% or more activity by this method at a concentration of 10 μM or lower, preferably 1 μM or lower, more preferably 0.1 μM or lower is selected as a substance inhibiting the activity of the polypeptide of the present invention.

<Cell-Based Screening Method>

The cell-based screening method comprises: bringing test substances into contact with a cell expressing the polypeptide of the present invention (preferably, a cell caused to express the polypeptide of the present invention) by mixing (i.e., addition) (contact step); analyzing whether the activity of the polypeptide of the present invention is inhibited or not by the test substance(s), by comparison with the activity of the polypeptide of the present invention not brought into contact with the test substances (analysis step); and selecting a substance inhibiting the activity of the polypeptide of the present invention (i.e., a therapeutic agent for cancer, particularly, a therapeutic agent for lung cancer). This screening method can specifically be practiced, for example, as described below.

First, test substances or solvent controls (e.g., DMSO) are brought into contact with a cell expressing the polypeptide of the present invention (i.e., a cell naturally expressing the polypeptide of the present invention or a cell caused to express the polypeptide of the present invention by its transformation with a vector comprising the polynucleotide of the present invention). The cells are cultured for a given time. The activity (i.e., autophosphorylating activity) of the polypeptide of the present invention is measured using cell lysates prepared from the cultured cells by dissolution, by SDS electrophoresis known in the art and immunoblotting using an anti-phosphorylated ALK antibody (e.g., Cell Signaling Technology) to thereby analyze whether the activity (i.e., autophosphorylating activity) of the polypeptide of the present invention is inhibited or not by the test substance(s). Whether the activity (i.e., autophosphorylating activity) of the polypeptide of the present invention is inhibited or not by the test substance(s) can be determined by analyzing a test substance-induced change in the tyrosine phosphorylation (i.e., autophosphorylation) level of the polypeptide of the present invention. Specifically, when the addition (i.e., contact) of a test substance inhibits the activity (i.e., autophosphorylating activity) of the polypeptide of the present invention as compared with the addition (i.e., contact) of the solvent control, this test substance is selected as a substance inhibiting the activity of the polypeptide of the present invention (i.e., a therapeutic agent for cancer, particularly, a therapeutic agent for lung cancer). Of the screening methods of the present invention, preferably, the cell-based screening method is practiced under the conditions described in Example 7(4) or 10(2). A substance that can inhibit 50% or more activity by this method at a concentration of 10 μM or lower, preferably 1 μM or lower, more preferably 0.1 μM or lower is selected.

<Expression Inhibition-Based Screening Method>

The expression inhibition-based screening method comprises: bringing test substances into contact with a cell expressing the polypeptide of the present invention (preferably, a cell caused to express the polypeptide of the present invention) by mixing (i.e., addition) (contact step); analyzing whether the expression of the polypeptide of the present invention is inhibited or not by the test substance(s), by comparison with the expression of the polypeptide of the present invention not brought into contact with the test substances (analysis step); and selecting a substance inhibiting the expression of the polypeptide of the present invention (i.e., a therapeutic agent for cancer, particularly, a therapeutic agent for lung cancer, that is shown to be positive for the polynucleotide of the present invention). This screening method can specifically be practiced, for example, as described below.

Test substances or solvent controls (e.g., DMSO) are brought into contact with any cell expressing the polypeptide of the present invention (i.e., a cell naturally expressing the polypeptide of the present invention or a cell caused to express the polypeptide of the present invention by its transformation with a vector comprising the polynucleotide of the present invention). After culture, extracts are prepared from the cells and subsequently used to analyze whether the expression of the polypeptide of the present invention is inhibited or not by the test substance(s). Whether the expression of the polypeptide of the present invention is inhibited or not can be analyzed by analyzing whether the mRNA or protein expression of the polypeptide of the present invention is inhibited or not. More specifically, the mRNA or protein level of the polypeptide of the present invention present in the cell extracts is identified by an expression level analysis method known in the art, for example, northern blotting, quantitative PCR, immunoblotting, or ELISA. More specifically, the inhibition of the mRNA or protein expression of the polypeptide of the present invention can be analyzed by a method described in Example 8(5) or 8(6). Whether the expression of the polypeptide of the present invention is inhibited or not by the test substance(s) can be determined by analyzing a test substance-induced change in the expression level of the polypeptide of the present invention. Specifically, when the contact of a test substance inhibits the expression level (i.e., mRNA or protein level) of the polypeptide of the present invention as compared with the contact of the solvent control, this test substance is selected as a substance inhibiting the expression of the polypeptide of the present invention (i.e., a therapeutic agent for cancer, particularly, a therapeutic agent for lung cancer). Of the screening methods of the present invention, preferably, the expression inhibition-based screening method is practiced under the conditions described in Example 8(5) or 8(6). A substance that can inhibit 50% or more activity by this method at a concentration of 10 μM or lower, preferably 1 μM or lower, more preferably 0.1 μM or lower is selected. Preferably, the selected test substance has an inhibitory activity on all cells used. However, a test substance having an inhibitory activity on one cell can also be selected.

Preferably, the screening method of the present invention further comprises, in addition to analyzing whether the polypeptide of the present invention is inhibited or not and selecting a substance inhibiting the polypeptide of the present invention, the step of confirming that the selected test substance has a therapeutic activity against cancer (particularly, lung cancer) that is shown to be positive for the polynucleotide of the present invention.

Examples of the step of confirming that the selected substance has a therapeutic activity against cancer (particularly, lung cancer) that is shown to be positive for the polynucleotide of the present invention include a step of practicing an evaluation method known in the art or a modified method thereof, for example, a method comprising analyzing the therapeutic activity of the selected substance against cancer (particularly, lung cancer) by treating, with the substance, cultured cells or tumor model animals expressing the polypeptide of the present invention (Clinical Oncology, 2nd ed., Cancer and Chemotherapy Publishers, Inc.).

Examples of the cultured cells expressing the polypeptide of the present invention include human cancer-derived (particularly, lung cancer-derived) cancer cells endogenously expressing the polypeptide of the present invention and cells artificially transformed from normal cells such as NIH3T3 by the expression of the polypeptide of the present invention. When the therapeutic activity against cancer that is shown to be positive for the polynucleotide of the present invention is examined using the cancer cells endogenously expressing the polypeptide of the present invention, a growth-inhibiting effect or cell death-inducing effect on the cancer cells expressing the polypeptide of the present invention by the test substance can be confirmed by adding the test substance selected by the screening method of the present invention to a culture medium of the cancer cells and measuring a cell count or cell death rate after culture by a standard method. If the selected test substance exhibits the growth-inhibiting effect and/or cell death-inducing effect on the cells, this selected test substance is confirmed to have a therapeutic activity against cancer (particularly, lung cancer) that is shown to be positive for the polynucleotide of the present invention. The test substance may be added to the medium under conditions in which the test substance is added at the start of culture or during culture once or any number of times without limitations. A culture period in the presence of the test substance can be set appropriately and is 5 minutes to 2 weeks, preferably 1 hour to 72 hours. Any of a variety of cell measurement methods may be used, such as trypan blue staining, Sulforhodamine, MTT, intracellular ATP measurement, and thymidine uptake methods, and any of a variety of cell death measurement methods may be used, such as LDH release measurement, annexin V staining, and caspase activity measurement methods.

When the transformed cells caused to express the polypeptide of the present invention are used, the inhibitory effect of the test substance on the growth of the transformed cells can be examined with anchorage-independent growth, one feature of cancer cells, as an index to thereby determine a therapeutic activity against cancer. The anchorage-independent growth refers to, in contrast to adherent normal cells that must adhere to the extracellular matrix (anchorage) for their survival and growth, the general essential property of cancer cells capable of growing even without such an anchorage. One of most reliable methods for examining the carcinogenesis of cells is to confirm that the cells can grow without an anchorage. Whether cells transformed from normal cells by gene expression exhibit an anchorage-independent growth ability can be examined to determine whether the gene is an oncogene. As described above, the EML4-ALK fusion polynucleotide is an oncogene. The transformed cells caused to express the polypeptide of the present invention also acquire an anchorage-independent growth ability. Therefore, the therapeutic activity of the test substance against cancer that is shown to be positive for the polynucleotide of the present invention can be examined with this property as an index. The anchorage-independent growth of the transformed cells caused to express the polypeptide of the present invention can be achieved by a method for cell culture in a soft agar medium or a method for cell culture in a plate capable of cell-culturing spheroids (cell aggregates). Measurement may be performed by the cell measurement methods described above. The transformed cell used may be any mammalian cell capable of expressing the polypeptide of the present invention and anchorage-independently growing. Examples thereof include, but not limited to, mouse fibroblast-derived cell line NIH3T3 cells caused to express the polypeptide of the present invention.

In the method using the tumor model animal, the test substance selected by the screening method of the present invention is administered to a mammalian individual that expresses the polypeptide of the present invention and forms tumor. The mammalian species that can be used is a non-human mammal and is, preferably, a mouse, rat, or hamster, more preferably, a mouse or rat. A cancer-bearing model animal serving as a tumor model animal can also be used in which the cancer cells endogenously expressing the polypeptide of the present invention or the cells transformed by the expression of the polypeptide of the present invention are transplanted subcutaneously, intradermally, or intraperitoneally or into each organ (e.g., a nude mouse in which NIH3T3 cells caused to express the polypeptide of the present invention are transplanted). Furthermore, an animal caused to overexpress the EML4-ALK fusion polynucleotide can also be used. The therapeutic activity of the test substance against cancer that is shown to be positive for the polynucleotide of the present invention can be confirmed by administering the test substance by a variety of administration methods such as oral, intravenous, subcutaneous, and intraperitoneal administrations and measuring the volume or weight of the tumor of the model animal. Preferably, the therapeutic activity of the selected substance against cancer that is shown to be positive for the polynucleotide of the present invention can be confirmed by a method described in Example 8(8).

Examples of the test substances used in the screening method of the present invention can include, but not particularly limited to, commercially available compounds (including peptides), a variety of compounds (including peptides) known in the art and registered in chemical files, compound groups obtained by a combinatorial chemistry technique (N. Terrett et al., Drug Discov. Today, 4 (1): 41, 1999), microorganism culture supernatants, plant- or marine organism-derived natural components, animal tissue extracts, double-stranded nucleic acids, antibodies or antibody fragments, and compounds (including peptides) chemically or biologically modified from compounds (including peptides) selected by the screening method of the present invention.

<Method for Treating Cancer that is Shown to be Positive for the Polynucleotide of the Present Invention and Double-Stranded Nucleic Acid>

The present invention encompasses a method for treating cancer that is shown to be positive for the polynucleotide of the present invention, comprising administering an effective amount of a substance inhibiting the polypeptide of the present invention (e.g., a substance [e.g., a double-stranded nucleic acid (including siRNA), protein (including an antibody or antibody fragment), peptide, or other compounds] obtained by the screening method of the present invention) to a subject in need of treatment of cancer that is shown to be positive for the polynucleotide of the present invention. As a substance in the method for treating cancer that is shown to be positive for the polynucleotide of the present invention, the following pharmaceutical composition (hereinafter, referred to as pharmaceutical composition of the present specification) can be used.

The active ingredient in the pharmaceutical composition of the present specification can be selected by the screening method of the present invention. Examples of the substance selected by the screening method of the present invention can include compounds A to D and a double-stranded nucleic acid described in Examples 7 and 8 below respectively. Alternatively, a compound selected by the screening method of the present invention from a low-molecular-weight compound with an inhibitory activity against ALK (ALK inhibitor) known in the art can be used as an active ingredient in the pharmaceutical composition of the present specification. The ALK inhibitor can be exemplified by ALK inhibitors described in WO 2005/097765 and WO 2005/016894. Particularly, a compound described in Wan W et al., Blood 107: 1617-1623, 2006 as well as WHI-P131 (4-(4'-Hydroxyphenyl)amino-6,7-dimethoxyquinazoline) and WHI-P154 (4-[(3'-Bromo-4'-hydroxyphenyl)amino]-6,7-dimethoxyquinazoline) (both, EMD Biosciences; hereinafter, WHI-P154 is referred to as a compound A; Marzec M et al., Lab Invest 85: 1544-1554, 2005) can be used. Alternatively, N-[2-(3-chlorophenyl)ethyl]-2-[({[4-(trifluoromethoxy)phenoxy]acetyl}amino)methyl]-1,3-thiazole-4-carboxamide (WO 2005/097765; hereinafter, referred to as a compound B), 5-chloro-$N^4$-[2-(isopropylsulfonyl)phenyl]-$N^2$-{2-methoxy-4-[4-(4-methylpiperazin-1-yl)piperidin-1-yl]phenyl}pyrimidine-2,4-diamine (WO 2005/016894; hereinafter, referred to as a compound C), or 2-[(5-bromo-2-{[2-methoxy-4-(4-methylpiperazin-1-yl)phenyl]amino}pyrimidin-4-yl)amino]-N-methylbenzenesulfonamide (WO 2005/016894; hereinafter, referred to as a compound D) can be used as an ALK inhibitor.

The double-stranded nucleic acid exemplified as an active ingredient in the pharmaceutical composition of the present specification comprises a double-stranded nucleic acid (RNA or DNA) portion and, preferably, 3'-terminal overhangs of the sense and antisense strands and induces RNAi. The RNAi is an evolutionarily conserved phenomenon, which occurs via a double-stranded nucleic acid with 21 to 23 bases produced by RNase III endonuclease (Genes Dev. 15, 485-490, 2001). The 3'-terminal overhangs are respectively any nucleic acid with 1 or 2 bases, preferably 2 bases. The number of bases (21 to 23 bases) described above is the number of bases of the sense or antisense strand including its overhang. The sense and antisense strands can have the same number of bases or a different number of bases and, preferably, have the same number of bases.

For example, U (uridine), A (adenosine), G (guanosine), or C (cytidine) can be used as ribonucleic acids constituting the 3'-terminal overhangs of the double-stranded nucleic acid. For example, dT (deoxythymidine), dA (deoxyadenosine), dG (deoxyguanosine), or dC (deoxycytidine) can be used as deoxyribonucleic acids constituting the 3'-terminal overhangs thereof.

The double-stranded nucleic acid that can be used as an active ingredient in the pharmaceutical composition of the present specification comprises a double-stranded portion designed on the basis of bases at positions 1743 to 1761, 1744 to 1762, 1750 to 1768, 1753 to 1771, 1756 to 1774, or 1757 to 1775 in SEQ ID NO: 1 and has an inhibitory activity on the expression of the polypeptide of the present invention (hereinafter, referred to as a double-stranded nucleic acid of the present invention). Examples of preferable aspects of such a double-stranded nucleic acid include siRNA-1 to siRNA-6 described in Example 8 (i.e., a double-stranded nucleic acid, one strand of which consists of the nucleotide sequence represented by SEQ ID NO: 111 and the other strand of which consists of the nucleotide sequence represented by SEQ ID NO: 112; a double-stranded nucleic acid, one strand of which consists of the nucleotide sequence represented by SEQ ID NO: 113 and the other strand of which consists of the nucleotide sequence represented by SEQ ID NO: 114; a double-stranded nucleic acid, one strand of which consists of the nucleotide sequence represented by SEQ ID NO: 115 and the other strand of which consists of the nucleotide sequence represented by SEQ ID NO: 116; a double-stranded nucleic acid, one strand of which consists of the nucleotide sequence represented by SEQ ID NO: 117 and the other strand of which consists of the nucleotide sequence represented by SEQ ID NO: 118; a double-stranded nucleic acid, one strand of which consists of the nucleotide sequence represented by SEQ ID NO: 119 and the other strand of which consists of the nucleotide sequence represented by SEQ ID NO: 120; and a double-stranded nucleic acid, one strand of which consists of the nucleotide sequence represented by SEQ ID NO: 121 and the other strand of which consists of the nucleotide sequence represented by SEQ ID NO: 122). The double-stranded nucleic acid of the present invention can be produced by standard methods (e.g., J. Am. Chem. Soc., 120, 11820-11821, 1998; and Methods, 23, 206-217, 2001). Alternatively, a contract manufacturer for double-stranded nucleic acids (e.g., RNAi Co., Ltd.) is well known by those skilled in the art and can be utilized in the production of the double-stranded nucleic acid. The target sequences of the siRNA-1 to siRNA-6 were confirmed by an siRNA sequence design system (commercial version siDirect (registered trademark), RNAi Co., Ltd.) to be specific to the polypeptide of the present invention.

The double-stranded nucleic acid of the present invention can be designed on the basis of DNA nucleotide sequences (bases at positions 1743 to 1761, 1744 to 1762, 1750 to 1768, 1753 to 1771, 1756 to 1774, or 1757 to 1775 in SEQ ID NO: 1) targeted by the siRNA-1 to siRNA-6. Such a double-stranded nucleic acid inhibits the polypeptide of the present invention, as with the siRNA-1 to siRNA-6. For example, siRNA can be designed which has a double-stranded portion consisting of an RNA nucleotide sequence directly converted from the whole target DNA nucleotide sequence. Alternatively, chimeric DNA-RNA double-stranded nucleic acid (which comprises both RNA and DNA in the identical strand) can be designed which has an RNA sequence converted from any portion of the target DNA nucleotide sequence. Furthermore a hybrid double-stranded nucleic acid, one strand of which is DNA and the other strand of which is RNA can be designed and produced for use. The conversion of the RNA nucleotide sequence from the DNA nucleotide sequence described herein means that dT in the DNA nucleotide sequence is converted to U and other bases, that is, dA, dG, and dC are converted to A, G, and C, respectively.

The double-stranded nucleic acid of the present invention exhibited an inhibitory effect on the anchorage-independent growth of a cell expressing the polypeptide of the present invention (Example 8(7)). Therefore, the double-stranded nucleic acid of the present invention can be utilized in the treatment of cancer that is shown to be positive for the polynucleotide of the present invention, comprising administering an effective amount thereof to a subject in need of treatment of cancer that is shown to be positive for the polynucleotide of the present invention.

A therapeutic effect on cancer that is shown to be positive for the polynucleotide of the present invention can be confirmed by use of a method generally known by those skilled in the art or a modified method thereof (see the "step of confirming that the selected substance has a therapeutic activity against cancer).

A preparation comprising, as an active ingredient, a substance inhibiting the polypeptide of the present invention (e.g., a substance [e.g., a double-stranded nucleic acid, protein (including an antibody or antibody fragment), peptide, or other compounds] obtained by the screening method of the present invention) can be prepared as a pharmaceutical composition using pharmacologically acceptable carriers, excipients, and/or other additives usually used in the preparation production according to the type of the active ingredient.

Examples of administration can include: oral administration using tablets, pills, capsules, granules, subtle granules, powders, or oral liquid agents; and parenteral administration using injections for intravenous injection (including intravenous drip), intramuscular injections, or subcutaneous injection, suppositories, percutaneous administration agents, or transmucosal administration agent. Particularly, parenteral administration such as intravenous injection is preferable for peptides that are digested in the stomach.

To prepare a solid composition for oral administration, 1 or more active substances can be mixed with at least one inactive diluent, for example, lactose, mannitol, glucose, microcrystalline cellulose, hydroxypropylcellulose, starch, polyvinyl pyrrolidone, or magnesium aluminometasilicate. The composition can contain additives other than the inactive diluent, for example, lubricants, disintegrants, stabilizers, or solvents or solubilizers according to a standard method. Tablets or pills can be coated, if necessary, with a sugar coating or with a film such as a gastrosoluble or enteric substance.

A liquid composition for oral administration can comprise, for example, an emulsion, solution, suspension, syrup, or elixir and can contain an inactive diluent generally used, for example, purified water or ethanol. The composition can contain additives other than the inactive diluent, for example, moisturizers, suspensions, sweeteners, flavors, or antiseptics.

A parenteral injection can comprise an aseptic aqueous or non-aqueous solution, suspension, or emulsion. A water-soluble solution or suspension can contain, for example, distilled water or saline for injection, as a diluent. A water-insoluble solution or suspension can contain, for example, propylene glycol, polyethylene glycol, plant oil (e.g., olive oil), alcohols (e.g., ethanol), or polysorbate 80 as a diluent. The composition can further contain moisturizers, emulsifiers, dispersants, stabilizers, solvents or solubilizers, or antiseptics. The composition can be sterilized, for example, by filtration using a bacterium-impermeable filter, formulation of germicides thereinto, or irradiation. Alternatively, an aseptic solid composition can be produced and dissolved in aseptic water or other aseptic media for injection for use.

A dose can be determined appropriately in consideration of the activity intensity of the active ingredient, that is, the substance obtained by the screening method of the present invention, conditions, the age or gender of a subject receiving administration, and so on. Preferably, the dose can be calculated according to a route as an amount that gives a serum concentration around tumor or intratumoral concentration 3 to 30 timers, for example, 10 times, higher than a drug concentration inhibiting 50% of the activity or expression of the polypeptide of the present invention. For example, the dose in oral administration in adult (60 kg in body weight) is usually approximately 0.1 to 100 mg/day, preferably, 0.1 to 50 mg/day. The dose in parenteral administration is 0.01 to 50 mg/day, preferably, 0.01 to 10 mg/day, in terms of an injection.

A therapeutic target by the pharmaceutical composition of the present specification is a test subject from which the presence of the polynucleotide of the present invention (preferably, the polynucleotide type v1 of the present invention and/or the polynucleotide type v2 of the present invention, particularly preferably, the EML4-ALK fusion polynucleotide v1 and/or the EML4-ALK fusion polynucleotide v2) and/or the polypeptide of the present invention (preferably, the polypeptide type v1 of the present invention and/or the polypeptide type v2 of the present invention, particularly preferably, the EML4-ALK fusion polypeptide v1 and/or the EML4-ALK fusion polypeptide v2) has been detected. The substance inhibiting the polypeptide of the present invention kills cells that have transformed due to the EML4-ALK fusion polynucleotide v1. Therefore, the substance inhibiting the polypeptide of the present invention serves as an effective therapeutic agent for cancer (particularly, lung cancer) that is shown to be positive for the polynucleotide of the present invention.

EXAMPLES

The present invention will be described in detail below by Examples, but the present inventions are not limited by these Examples. Further, unless otherwise stated the process of the present invention can be carried out according to publicly known methods. Also, commercially available reagents and kits can be used in accordance with the instructions of the commercial products.

A full length ALK cDNA was kindly supplied by Dr. Steve Morris of St. Jude Children's Research Hospital. Further, this research project was approved by the ethics committee for gene analysis study at Jichi Medical University.

Anti-phosphorylated ALK antibody and anti-ALK antibody used were produced by Cell Signaling Technology Inc. and NEOMARKERS Inc., respectively.

Example 1

Isolation of EML4-ALK Fusion Polynucleotide v1

(1) Construction of cDNA Library

Using a RNA purification kit (RNeasy Mini Column; Qiagen Inc.), RNA was extracted from a resected specimen of lung adenocarcinoma of a 62 year old male who gave informed consent and cDNA was synthesized using reverse transcriptase (Power Script Reverse Transcriptase) and primers (an oligonucleotide of SEQ ID NO: 42 and CDS primer IIA) (all from Clontech Inc.). After selectively amplifying the full length cDNA by polymerase chain reaction (PCR) (17 cycles of 98° C. for 10 seconds and 68° C. for 6 minutes) using a primer (5'-PCR primer IIA; Clontech Inc.) and a polymerase (primeSTAR HSDNA polymerase, Takara Bio Inc.), a BstX1 adapter (Invitrogen Co.) was attached to the both ends of cDNA. The cDNA thus obtained was ligated to a retrovirus plasmid, and a retrovirus plasmid library was constructed by introducing this plasmid to *E. coli* DH10B (Invitrogen Inc.). As the result, the plasmid library containing clones more than 1,500,000 colony forming units in total has been successfully constructed.

(2) Focus Formation Assay

2 μg of the plasmid of the library described above and 0.5 μg of a plasmid for packaging (pGP, and pE-eco, both of which were obtained from Takara Bio Inc.) were transfected to BOSC23 packaging cells using a transfection reagent. Two days after the transfection, the culture supernatant was recovered as a solution of recombinant retrovirus library, mixed with polybrene (Sigama Inc.) at a concentration of 4 μg/ml, and the mixture was added to mouse 3T3 cells at MOI (multiplicity of infection) of 0.1 concentration. Two days later, the culture supernatant of 3T3 cells was changed to DMEM-F12 medium (Invitrogen Inc.) supplemented with 5% bovine serum (Invitrogen Inc.) and 2 mM L-glutamine, and cells were cultured 2 more weeks to obtain 10 or more kinds of transformed foci. After isolating each 3T3 cell clone, the culturing of the clones was continued separately, and the genomic DNA of each clone was extracted. The viral cDNA integrated in each 3T3 clone was amplified and recovered by carrying out PCR (30 cycles of 98° C. for 10 seconds and 68° C. for 6 minutes) using 10 ng of the genomic DNA as a template, 5'-PCR primer IIA primer and DNA polymerase (PrimeStar HS DNA polymerase; Takara Bio Inc.), and cloned in pT7Blue-2 vector.

One of the cDNA thus obtained was 3926 base pair long (SEQ ID NO: 1) and had a single long open reading frame (from the 271st to 3447th base of SEQ ID NO: 1) coding for a protein having 1059 amino acid residues (SEQ ID NO: 2). Interestingly, about half of the amino-terminus of the protein (1-496 amino acid residues of SEQ ID NO: 2), coded by the present cDNA having a novel full-length sequence, was perfectly matched to 1-496 amino acid residues of echinoderm microtubule associated protein like-4; EML4 (GenBank accession No. NM_019063), and on the other hand, about half of the carboxyl terminus (497-1059 amino acid residues of SEQ ID NO: 2) was perfectly matched to the amino acid sequence of anaplastic lymphoma kinase; ALK (GenBank accession No. AB209477. Also, in the nucleotide sequence (SEQ ID NO: 1) of the cDNA that we identified, 99.9% of the 35-1759 base matched the 1-1725 base of the reported human EML4 cDNA, and the 1760-3677 base of our cDNA (SEQ ID NO: 1) matched the 3613-5530 base of human ALK cDNA by 99.9%. Although respective sequences are a little different from the reported base sequences, any of these differences do not lead to amino acid replacement, and therefore it may be possible that they are gene sequence polymorphism. From the above results, the present cDNA was believed to be a fused cDNA between a part of EML4 cDNA and a part of ALK cDNA. Further, the obtained cDNA (the cDNA of EML4-ALK fused polynucleotide v1) contained a domain of ALK tyrosine kinase.

Example 2

Confirmation of EML4-ALK Fusion Polynucleotide v1

The EML4 gene and ALK gene in human are both mapped in the short arm of the second chromosome in opposite directions (head to head direction). For the cDNA of the EML4-ALK fusion polynucleotide found in Example 1 to be produced, respective genomes are needed to be cut in the intron downstream from the exon 13 of the EML4 gene and the intron upstream from the exon 21 of the Alk gene, and re-ligated with the one gene in the reverse direction. To prove this directly, PCR (after 94° C. for 1 minute, 40 cycles of 98° C. for 20 seconds and 68° C. for 9 minutes) was carried out using primers having the base sequences of SEQ ID NO: 40 (a sequence designed in the sense strand of the 3' terminus of the exon 13 of the EML4 gene) and SEQ ID NO: 36 (a sequence designed in the anti-sense strand of the exon 21 of the ALK gene), templates of the genomic DNA of a patient (ID 33) and the control genomic DNA (the genomic DNA of peripheral monocytes of normal healthy female (46, XX)) and DNA polymerase (LA Taq polymerase; Takara Bio Inc.).

As the result, as shown in FIG. 1, a PCR product having about 4 kbp length was obtained only by the genomic DNA of the present patient. That is, it was confirmed as expected that in the genomic level the EML4 gene and the ALK gene were cut at the introns and re-ligated in the reverse direction. Further, this PCR product of about 4 kbp was cloned into a pT7Blue-2 vector (Novagen Inc.) and the total base sequence was determined. It was made clear that the cuts were located approximately 3.6 kbp downstream from the exon 13 of the EML4 gene and 297 bp upstream from the exon 21 of the ALK gene. The base sequence is shown in SEQ ID NO: 4. SEQ ID NO: 4 is a genomic sequence including the fusion point of the EML4 gene and ALK gene.

Example 3

Screening for EML4-ALK Fusion Polynucleotide in Clinical Specimens (1) Detection of EML4-ALK fusion polynucleotide using cDNA cDNAs were synthesized from 33 cases of clinical specimens (resected specimens of non-small cell lung cancer) including the case (ID 33) used in the present Example 1 and 2 and from peripheral monocytes of one case of a normal healthy subject (46, XX).

Figure 2:
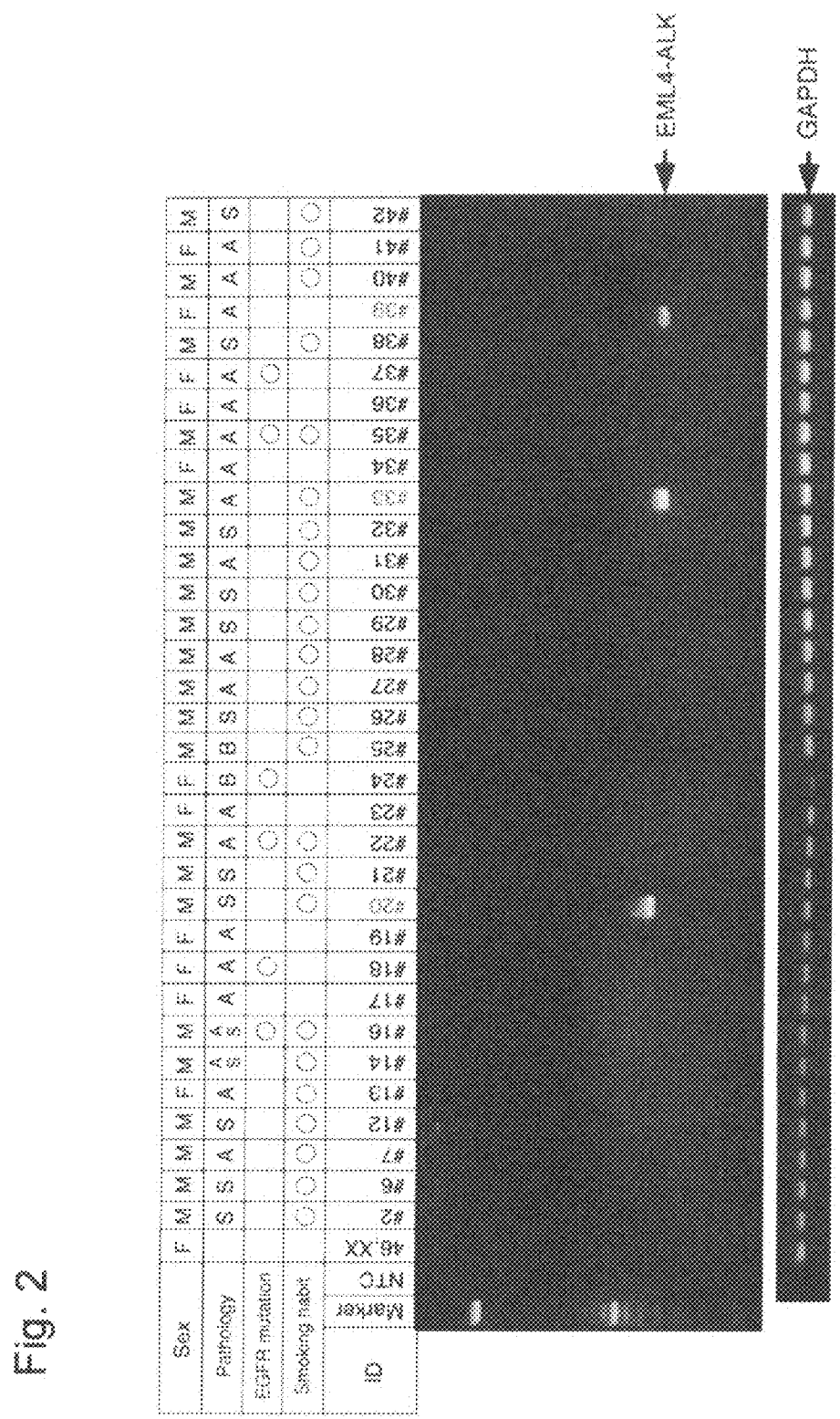
FIG. 2 shows the results of the screening for EML4-ALK fusion polynucleotide in specimens of lung cancer patients. Lane "46, XX" shows the result of using peripheral monocytes of a normal healthy female subject, and "ID #2" to "ID #42" show the result of using samples obtained from excised specimens from lung cancer patients. In addition, lane "NTC" shows the result without added substrate cDNA. Lane "marker" is the lane where the size marker DNA was electrophoresed (upper section). The results of amplification of GAPDH cDNA are shown in the lower section. Sex (M, male; F, female), pathology (S, squamous cell carcinoma; A, adenocarcinoma; AS, adenosquamous carcinoma; B, bronchioloaleveolar carcinoma) and the presence or absence of EGFR mutation and the presence or absence of smoking history are shown in the upper part of the figure.

To detect the cDNA of EML4-ALK fusion polynucleotide v1, PCR (50 cycles of 94° C. for 15 seconds, 60° C. for 30 seconds and 72° C. for 1 minute) was carried out using a quantitative PCR kit (QuantiTect SYBR Green; Qiagen Inc.), the cDNAs as substrates prepared from the clinical specimens and the normal healthy subject described above and oligonucleotides of SEQ ID NO: 8 and 9 as primers. Using the same specimens, PCR amplifications of the glyceraldehyde-3-phosphate dehydrogenase (herein after GAPDH) cDNA was tried as a control. To detect the GAPDH cDNA, oligonucleotides consisting of the nucleotide sequences represented by SEQ ID NO: 10 and 11 were used as primers. Amplified respective samples were electrophoresed with a size marker DNA (Marker: 50 bp ladder, Invitrogen Inc.). As the result, as shown in the upper part of FIG. 2, in the total 3 cases including ID 33, the cDNA of the EML4-ALK fusion polynucleotide v1 was detected. Further, in all the cases analyzed, an amplification of the GAPDH cDNA was confirmed clearly (Lower part of FIG. 2). In addition, the base sequence of the PCR products identified in the cases of ID 20 and ID 39 were analyzed and the result confirmed that the sequence was identical to that of ID 33 (the 247 bp including the fusion point of the EML4 gene and the ALK gene. SEQ ID NO: 14). That is, the result of the analyses of the 33 cases of non-small cell lung cancer confirmed that the fusion of the EML4 gene and the ALK gene occurs in 9.1% of the cases (3/33 cases). Further, in the cases where the cDNA of the EML4-ALK fusion polynucleotide v1 was positive, one case (ID 20) was a squamous cell carcinoma specimen and the other (ID 39) was an adenocarcinoma specimen.

Mutation in the EGFR gene has been known to be one of the causes of lung cancer. In the 33 specimens of the cases analyzed as described above, the analysis of the presence of an abnormality in the base sequence of the EGFR gene according to the known method confirmed a partial deletion of the exon 19 in 6 cases. The cases having the EGFR gene mutation and the cases positive for the EML4-ALK fusion polynucleotide belonged to different subgroups. That is, the existing therapeutic agents for lung cancer, which are therapeutic agent for the lung cancer caused by the mutation in the EGFR gene, are expected to be not effective for the lung cancer patients who are positive for the EML4-ALK fusion polynucleotide.

Also, the 33 cases analyzed as described above were subjected to the investigation whether the full length ALK gene existed, and it was found that it existed in 8 cases. The specimens of the 7 cases among these 8 cases did not contain the EML4-ALK fusion polynucleotide. (That is, the full length ALK gene did not exist in the 2 cases among the 3 cases where the EML4-ALK fusion polynucleotide was positive).

Further, analyses of 42 cases of other non-small cell lung cancer cases by a similar method as described above gave about 1 kbp PCR products in 4.8% of the cases (2/42 cases), which are larger than those detected in the cases of ID 20 and ID 39 cases. These were cloned in pT7Blue-2 vector and the base sequence was analyzed. The results indicated that these were not the exon 13 of the EML4 gene but a fusion product of the exon 20 of the EML4 gene and the exon 21 of the ALK gene (SEQ ID NO: 3). That is, in these products the fused ALK gene fragment was the same, but the point of cleavage in the EML4 was different. The cDNA sequence of the fusion gene of the exon 1-20 of the EML4 gene and the exon 21-30 of the ALK gene, which contains the fusion point of the EML gene and the ALK gene found in SEQ ID NO: 3, is shown in SEQ ID NO: 6, and the amino acid sequence of the polypeptide coded thereby is shown in SEQ ID NO: 7. In the present description, the gene that codes for the protein consisting of the polypeptide represented by SEQ ID NO: 7 is called the EML4-ALK fusion polynucleotide v2. The plasmid produced here in which a partial fragment of the EML4-ALK fusion polynucleotide v2 is cloned is designated as EML4-ALKv2 partial/pT7Blue-2.

(2) Detection of the EML4-ALK Fusion Polynucleotide v1 Using Genomic DNA

It turned out that the presence of the EML4-ALK fusion polynucleotide can be detected in samples obtained from the test subjects by PCR using the genomic DNA samples extracted from the clinical specimens (especially the lung tissue) of the test subjects as Example 2. Thus, as shown below, detection of EML4-ALK fusion polynucleotide v1 was tried using various primers. Using 1 ng of pT7Blue-2 vector as a template, in which the PCR product of about 4 kbp produced as described above was cloned and using a pair of oligonucleotides having 16 to 20 bases as a sense primer and an antisense primer [total 10 pairs of the primer set (SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, and SEQ ID NO: 33 and SEQ ID NO: 34)], PCR (30 cycles of 94° C. for 15 seconds, 55° C. for 30 seconds and 72° C. for 1 minute) was carried out by a DNA polymerase (rTaq DNA polymerase; Takara Bio Inc.). The results indicated that a single DNA fragment having an expected size (from about 270 to 380 bp) was amplified in each PCR. It became clear from the above results that the detection of the EML4-ALK fusion polynucleotide v1 is possible by carrying out PCR using the genomic DNA extracted from the clinical specimens as a template and various primer sets which are thought to specifically detect the presence of the EML4-ALK fusion polynucleotide v1.

(3) Detection of the EML4-ALK Fusion Polynucleotide v2 Using Genomic DNA

An oligonucleotide having the base sequence represented by SEQ ID NO: 35 in the EML4 exon 20 and an oligonucleotide having the base sequence represented by SEQ ID NO: 36 in the antisense side of the ALK exon 21 were designed as a sense primer and antisense primer, respectively. Using these and using the genomic DNA of a patient (ID#KL-3121) as a template in which the cDNA of the EML4-ALK fusion polynucleotide v2 was detected, PCR (after 94° C. for 1 minute, 40 cycles of 98° C. for 20 seconds and 68° C. for 6 minutes) was carried out with a DNA polymerase (LA Taq polymerase; Takara Bio Inc.). As the result, a PCR product of about 850 bp was obtained. The PCR product was cloned in pT7Blue-2 vector, the base sequence was determined and an 853 bp sequence shown in SEQ ID NO: 5 was obtained. The analyses of the sequence revealed that the 35 bp located at the 3' terminus of the EML4 exon 20 and the 544 bp of the intron sequence downstream from the EML4 exon 20 were linked to the 233 bp of the intron sequence upstream from the ALK exone 21 and the 41 bp located at the 5' terminus of the ALK exon 21. That is, it has become clear that the cleavage of the genome occurred at a location 544 bp downstream from the EML4 exon 20 and at a location 233 bp upstream from the ALK exon 21. Using 1 ng of pT7Blue-2 vector as a template, in which the 853 bp PCR product prepared as described above was cloned, and using a pair of oligonucleotides having 16 to 20 bases as a sense primer and an antisense primer [total 10 pairs of the primer set (SEQ ID NO: 37 and SEQ ID NO: 38, SEQ ID NO: 39 and SEQ ID NO: 18, SEQ ID NO: 41 and SEQ ID NO: 20, SEQ ID NO: 43 and SEQ ID NO: 22, SEQ ID NO: 45 and SEQ ID NO: 46, SEQ ID NO: 47 and SEQ ID NO: 26, SEQ ID NO: 49 and SEQ ID NO: 28, SEQ ID NO: 51 and SEQ ID NO: 52, SEQ ID NO: 53 and SEQ ID NO: 54, and SEQ ID NO: 55 and SEQ ID NO: 34)], PCR reaction was carried out under the same conditions as those in Example 3(2). As the result, a single DNA fragment having the expected size (from about 270 to 380 bp) was amplified in each PCR. It turned out from the above results that the detection of the presence of the EML4-ALK fusion polynucleotide v2 is possible by carrying out PCR using the genomic DNA extracted from the clinical specimens as a template and primer sets which are thought to specifically detect the EML4-ALK fusion polynucleotide v2.

Example 4

Method for Detecting mRNA of the EML4-ALK Fusion Polynucleotide (1) Construction of EML4-ALK Fusion Polypeptide v1 Expression Vector and Cloning of EML4-ALK Fusion Polynucleotide v2

From the clone in which the EML4-ALK fusion polynucleotide v1 was cloned in the positive direction (designated as EML4-ALKv1/pT7Blue-2) the insert was taken out by digesting with restriction enzymes EcoRI and SalI and subcloned at the EcoRI-SalI sites of pMXS (JBC 275, 24945-24952, 2000). This was designated as EML4-ALKv1/pMXS. Also, the cDNA of the coding region of EML4-ALK fusion polynucleotide (from codon 3 to the last codon) having the sites at the both ends which are recognized by restriction enzyme EcoRI was amplified by carrying out PCR (25 cycles of 98° C. for 10 seconds, 68° C. for 5 minutes) using EML4-ALKv1/pT7Blue-2 plasmid as a template and oligonucleotides consisting of the base sequence represented by SEQ ID NO: 59 and SEQ ID NO: 60 as primers and a DNA polymerase (PrimeStar HS DNA polymerase). After digesting with EcoRI, this was inserted at the EcoRI site of an expression vector pcDNA3, which is modified so that the insert can be expressed with an FLAG tag added to the N-terminus, to produce an expression plasmid (FLAG-EML4-ALKv1/pcDNA3) for EML4-ALK fusion polypeptide v1 having the FLAG tag at the N-terminus (hereinafter, FLAG-EML4-ALKv1). Further, the cDNA of FLAG-EML4-ALKv1 was taken out from this vector by digesting with restriction enzymes HindIII and XbaI, and after converting the both ends to blunt, an EcoRI-NotI-BamHI adaptor (Takara Bio Inc.) was ligated to both ends. The product was inserted at the EcoRI site of an expression vector, by which the inserted cDNA and cell surface antigen CD8 can be expressed at the same time (bicistronic vector pMX-iresCD8; J. Biol. Chem. 2001, vol. 276, p 39012-39020), to produce an expression vector which expresses both FLAG-EML4-ALKv1 and CD8. This was designated as FLAG-EML4-ALKv1/pMX-iresCD8.

EML4-ALK fusion polynucleotide v2 was cloned as follows.

Using a full length polynucleotide of EML4 cloned in pT7Blue-2 according to the non-patent document 8 as a template for obtaining a polynucleotide fragment coding for EML4 of the EML4-ALK fusion polynucleotide v2, and using an oligonucleotide represented by SEQ ID NO: 57, in which an EcoRI cleavage sequence is attached to the 5'-terminus of the start codon ATG of the EML4 gene exon 1 and an oligonucleotide represented by SEQ ID NO: 58, the sequence of which consists of 10 bases of the 5' terminus of the antisense sequence of the ALK gene exon 21 fused to the 5' terminus of the antisense sequence to the 20 bases of 3' terminus of the EML4 gene exon 20, respectively as a sense and an antisense primers, and using a DNA polymerase (Pyrobest DNA polymerase; Takara Bio Inc.), PCR (25 cycles of 94° C. for 20 seconds, 60° C. for 30 seconds, 72° C. for 1 minute) was carried out to obtain a PCR product of about 2260 bp. This product was designated as PCR product A.

While, using EML-ALKv1/pTBlue-2 produced in the present Example 4(1) as a template to obtain the ALK polynucleotide fragment of the EML4-ALK fusion polynucleotide v2, and using an oligonucleotide represented by SEQ ID NO: 101, the sequence of which consists of the 10 bases of the sense sequence at the 3' terminus of the EML4 gene exon 20 fused to the 5' terminus of the 20 bases of the sense sequence at the 5' terminus of the ALK gene exon 21 and an oligonucleotide represented by SEQ ID NO: 102, in which the Xba I cleavage sequence is attached to the 5' terminus of the antisense sequence area containing the stop codon present in the ALK gene exon 30 as a sense and an antisense primers, respectively, PCR was carried out under the same condition as that for obtaining PCR product A to obtain a PCR product of about 1700 bp. This was designated PCR product B.

PCR products A and B described above were mixed, and annealing and extension reactions (3 cycles of 94° C. for 1 minute, 55° C. for 30 seconds and 72° C. for 2 minutes and 30 seconds) were carried out using a DNA polymerase (Pyrobest DNA polymerase; Takara Bio Inc.) to obtain a product of about 4000 bp. This product was TA-cloned into pCR2.1-TOPO vector using TOPO TA Cloning kit (Invitrogen Inc.), and the base sequence was analyzed. As shown in SEQ ID NO: 6, the result indicated that the EML4-ALK fusion polynucleotide v2 which consisted of 2242 bases from the start codon ATG of the EML4 gene to the exon 20 and 1691 bases from the ALK gene exon 21 to the stop codon of the exon 30 was obtained.

(2) Method for Detecting mRNA of EML4-ALK Fusion Polynucleotide v1 and v2

Using 1 ng of FLAG-EML4-ALKv1/pMX-iresCD8 described in (1) as the template of EML4-ALK fusion polynucleotide v1 and 1 ng of EML4-ALKv2 partial/pT7Blue-2 in Example 3 as the template for EML4-ALK fusion polynucleotide v2, and using a pair of oligonucleotides having 16 to 20 bases for each variant as a sense primer and an antisense primer [total 10 pairs of the primer set for EML4-ALK fusion polynucleotide v1; (SEQ ID NO: 61 and SEQ ID NO: 62, SEQ ID NO: 63 and SEQ ID NO: 64, SEQ ID NO: 65 and SEQ ID NO: 66, SEQ ID NO: 67 and SEQ ID NO: 68, SEQ ID NO: 69 and SEQ ID NO: 70, SEQ ID NO: 71 and SEQ ID NO: 72, SEQ ID NO: 73 and SEQ ID NO: 74, SEQ ID NO: 75 and SEQ ID NO: 76, SEQ ID NO: 77 and SEQ ID NO: 78, and SEQ ID NO: 79 and SEQ ID NO: 80) and the primer set for EML4-ALK fusion polynucleotide v2; (SEQ ID NO: 81 and SEQ ID NO: 82, SEQ ID NO: 83 and SEQ ID NO: 84, SEQ ID NO: 85 and SEQ ID NO: 86, SEQ ID NO: 87 and SEQ ID NO: 88, SEQ ID NO: 89 and SEQ ID NO: 90, SEQ ID NO: 91 and SEQ ID NO: 92, SEQ ID NO: 93 and SEQ ID NO: 94, SEQ ID NO: 95 and SEQ ID NO: 96, SEQ ID NO: 97 and SEQ ID NO: 98, and SEQ ID NO: 99 and SEQ ID NO: 100)], PCR (30 cycles of 94° C. for 15 seconds, 55° C. for 30 seconds and 72° C. for 1 minute) was carried out by a DNA polymerase (rTaq DNA polymerase; Takara Bio Inc.). As the result, in all the primer set, a single DNA fragment, each having the expected size (about from 260 to 350 bp), was amplified. From the above results, it was confirmed that detection of the presence of the EML4-ALK fusion polynucleotide v1 and/or v2 is possible by carrying out RT-PCR according to the present Example using mRNA extracted from the samples of test subjects as the template.

The results of Example 3 and 4(2) described above indicated that the presence of the EML4-ALK fusion polynucleotide v1 and v2 can be detected by using either cDNA or genomic DNA prepared from the clinical specimens obtained from test subjects. This fact suggests that patients having the EML4-ALK fusion polynucleotide can be selected and that a tailor-made treatment can be practiced by which the patients to be treated by the administration of inhibitors of the EML4-ALK fusion polynucleotide and/or polypeptide are selected beforehand and then treated.

Example 5

Detection of EML4-ALK Fusion Polynucleotide v1 in Sputum (1) Production of Mouse BA/F3 Cells Expressing FLAG-EML4-ALKv1

A recombinant retrovirus was produced by a similar method as described before using FLAG-EML4-ALKv1/pMX-iresCD8 and a blank vector (pMX-iresCD8), and mouse lymphatic cell line BA/F3 cells were infected therewith. Cells expressing CD8 on the cell surface were simply purified using magnetic beads reagent for cell separation and a purification column (anti-CD8 monoclonal antibody bound magnetic beads and MiniMACS purification column, both Miltenyi Biotec Inc.).

(2) Detection of EML4-ALK Fusion Polynucleotide v1 in Sputum

After mixing sputum samples of normal healthy subjects with the BA/F3 cells expressing EML4-ALK fusion polynucleotide v1 (hereinafter v1 expressing BA/F3 cells) at 0/mL, 10 cells/mL, 100 cells/mL, 1000 cells/mL and 10,000 cells/mL, cDNA was synthesized by the standard method. The presence of the EML4-ALK fusion polynucleotide v1 in sputum was examined by carrying out a PCR reaction (50° C. for 2 minutes, 95 minutes for 15 minutes and further 40 cycles of the following reaction (94° C. for 15 seconds, 60° C. for 30 seconds and 72° C. for 1 minute)) using the cDNA described above as a substrate, and oligonucleotides consisting of the base sequence represented by SEQ ID NO: 8 and SEQ ID NO: 9 as primers and a quantitative PCR kit (QuantiTect SYBR Green; Qiagen Inc.), and PCR products were obtained. As the results, in every case except at 0/mL, the presence of EML4-ALK fusion polynucleotide could be confirmed.

Conventionally cytopathological examination using sputum samples has been an important diagnostic method for lung cancer diagnosis. This diagnosis for lung cancer is based on the presence of atypical cells in sputum but reliable diagnosis cannot be made unless many lung cancer cells exist in the sputum. However, most of the time, such cases were already in the advanced stage and it has been almost impossible to practice effective early diagnosis for lung cancer. According to the present invention, if the EML4-ALK fusion polynucleotide is present in sputum, it became clear that it can be detected by PCR even if a minute amount.

Example 6

Investigation of Transformability and Tumorgenicity of EML4-ALK Fusion Polypeptide v1

(1) Analysis for the EML4-ALK Fusion Polypeptide v1

EML4-ALK (K589M)/pMXS, in which the 589th amino acid (ATP binding site), a lysine residue, of the EML4-ALK fusion polypeptide v1 was replaced with methionine was produced using EML4-ALKv1/pMXS as a substrate and using a mutation introducing kit (QuickChange Site-Directed Mutagenesis Kit; Stratagene Inc.). In the reaction, oligonucleotides of SEQ ID NO: 103 and SEQ ID NO: 104 were used. The ALK cDNA (Morris, S W et al, Science. 1994 Mar. 4; 263 (5151):1281-4) was cloned to a retrovirus vector pMXS and pMX-iresCD8 according to the standard method (designated as ALK/pMXS and ALK/pMX-iresCD8, respectively).

Figure 3:
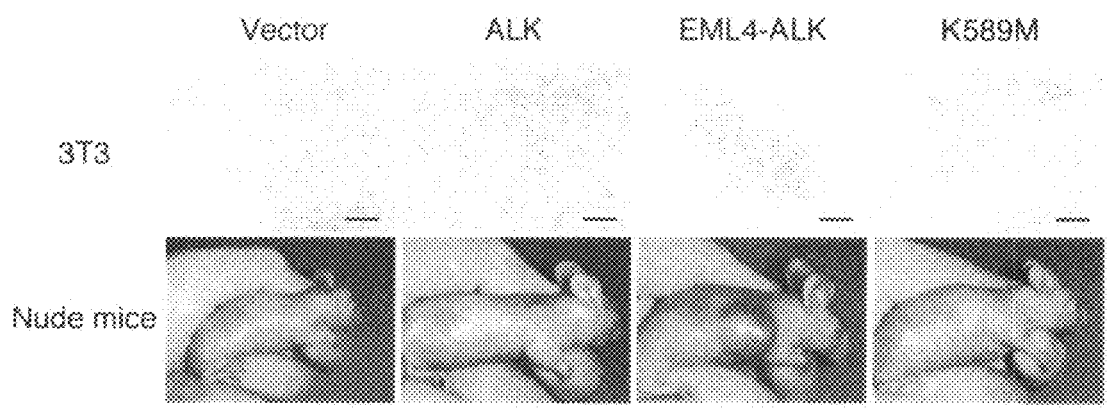
FIG. 3 shows tumorgenicity of the genes. The upper section of the figure (3T3) shows 3T3 fibroblast cells when a blank vector (Vector), and expression plasmid such as full length ALK/pMXS (ALK), EML4-ALKv1/pMXS (EML4-ALK) or EML4-ALK (K589M)/pMXS were introduced. The scale bar represents 100 μm. The lower section of the figure (Nude mice) shows the result of the inoculation of each 3T3 fibroblast cell line to nude mice.

EML4-ALKv1/pMXS described above, full length ALK/pMXS, a plasmid expressing EML4-ALK (K589M)/pMXS and a blank vector without inserted cDNA (pMXS) were transfected to 3T3 fibroblast cells by the phosphate calcium method and cultured for 21 days. As shown in the upper part of FIG. 3, many transformation foci were observed only when the EML4-ALK fusion polypeptide v1 expressing vector was transfected. The scale bar indicates 100 µm. Further, the same transfected 3T3 cells were inoculated subcutaneously to nude mice at $5 \times 10^5$ cells/mouse and observed for 20 days. It turned out also that tumor was formed only when EML4-ALK fusion polypeptide v1 expressing cells were inoculated. The tumor formation numbers (the number of inoculation sites of 3T3 cells and the number of tumor formation among them) are as follows. The tumor formation number of the full length ALK expression was 0 among 8, while the tumor formation number in the EML4-ALK fusion polypeptide v1 expressing cells was 8 among 8. In addition the tumor formation number of EML4-ALK (K589M) expressing cells was 0 among 8. These results demonstrate that since the full length ALK polypeptide expression does not induce tumor but the EML4-ALK fusion polypeptide v1 is tumorgenic, the EML4-ALK fusion polynucleotide v1 is the causal gene of cancer. Also, since the tumorgenicity of EML4-ALK was not observed in EML4-ALK (K589M), it would appear that the tumorgenicity was dependent on the kinase activity. Hereinafter, the 3T3 cells in which EML4-ALK fusion polypeptide v1 is expressed are designated as the v1 expressing 3T3 cells.

(2) Analysis of Various Deletion Mutants of EML4-ALK Fusion Polynucleotide v1

Various deletion mutants (ΔBasic deletion mutant, ΔHELP deletion mutant, ΔWD deletion mutant) of the EML4 part of the EML4-ALK fusion polynucleotide v1 was prepared by PCR reaction using FLAG-EML4-ALKv1/pMX-iresCD8 as a template and using a cloning kit (ExSite PCR-based Site-Directed Mutagenesis; Stratagene Inc.). For preparing ABasic deletion mutant (31-140th amino acids of the EML4-ALK fusion polypeptide v1 were deleted), the oligonucleotides having the base sequences represented by SEQ ID NO: 105 and SEQ ID NO: 106 were used as the primer set; for preparing ΔHELP deletion mutant (220-296th amino acids of the EML4-ALK fusion polypeptide v1 were deleted) the oligonucleotides having the base sequences represented by SEQ ID NO: 107 and SEQ ID NO: 108 were used; and for preparing ΔWD deletion mutant (305-475th amino acids of the EML4-ALK fusion polypeptide v1 were deleted) the oligonucleotides having the base sequences represented by SEQ ID NO: 109 and SEQ ID NO: 110 were used. Using these deletion mutant plasmids, retrovirus solutions were prepared using a similar method to that of Example 1 to obtain infected 3T3 cells. These respective infected cells were inoculated subcutaneously to nude mice to investigate the tumorgenicity, and it was found that tumors were formed by 3T3 cells expressing ΔHELP deletion mutant and ΔWD deletion mutant. The tumor forming number of respective 3T3 cells expressing ABasic deletion mutant, ΔHELP deletion mutant and ΔWD deletion mutant was 0 among 8, 7 among 8 and 8 among 8, respectively. Since no tumor formation was observed in the ABasic deletion mutant, it is demonstrated that the 31-140th amino acids of the EML4-ALK fusion polypeptide v1 are important in tumorgenesis. Since the EML4-ALK fusion polypeptide v2, like the EML4-ALK fusion polypeptide v1, appears to contain the aforementioned the 31-140th amino acids and the ALK kinase region, the EML4-ALK fusion polynucleotide v2, like the EML4-ALK fusion polynucleotide, is considered to be the causal gene of cancer which codes for the polypeptide having the transformability and tumorgenicity to 3T3 cells.

Example 7

Method for Screening for the EML4-ALK Fusion Polypeptide Inhibitors (1) Preparation the EML4-ALK Fusion Polypeptide v1

The v1 expressing BA/F3 cells (Example 5(1)) were cultured in RPM1640 medium containing 10% of fetal bovine serum to obtain $2.7 \times 10^9$ cells. After washing 3 times with PBS, cells were lysed in a lysis solution (50 mM Tris.HCl (pH7.4), 150 mM NaCl, 1% Triton X100, 5 mM EDTA, 5 mM EGTA, 1 mM NaVO$_4$, 1 mM DTT and protease inhibitor cocktail complete). The EML4-ALK fusion polypeptide v1 present in the supernatant obtained after a centrifugation was purified using ANTI-FLAG M2 Affinity Gel (SIGMA-ALDRICH Inc) according to the method described in the product information document. For washing and elution, the washing solution (50 mM Tris HCl (pH7.4), 250 mM NaCl, 0.05% Brij35, 1 mM EDTA, 1 mM EGTA, 1 mM NaVO$_4$, 1 mM DTT, complete) and the elution solution (50 mM Tris.HCl (pH7.4), 150 mM NaCl, 0.05% Brij35, 1 mM DTT, 0.5 mg/mL FLAG peptide) were used, respectively. Immunoblotting using anti-ALK antibody and anti FLAG M2 antibody (SIGMA-ALDRICH Inc.) and silver staining were carried out for the eluate to detect the EML4-ALK fusion polypeptide v1. It was demonstrated that the EML4-ALK fusion polypeptide v1 can be prepared by this method.

(2) Detection of the In Vitro Kinase Activity of the EML4-ALK Fusion Polypeptide v1

The EML4-ALK fusion polypeptide v1 purified as described above was diluted in a reaction solution (15 mM Tris.HCl (pH7.4), 0.25 mM $MgCl_2$, 0.01% Tween-20, 2 mM DTT), and then ATP was not added or ATP 20 µM was added. The respective mixtures were reacted at room temperature for 1 hour. After the reaction, the auto phosphorylated EML4-ALK fusion polypeptide v1 and the EML4-ALK fusion polypeptide v1 were detected by immunoblotting using anti-phosphorylated ALK antibody, which recognizes specifically the product phosphorylated at the 1604th tyrosine residue of ALK, and anti-ALK antibody, and quantitated by an image analysis system (VersaDoc Imaging System; Bio-Rad Inc.). The amount of phosphorylation was calibrated by dividing the count of the autophosphorylated EML4-ALK fusion polypeptide v1 by the count of the EML4-ALK fusion polypeptide v1. As the result, the autophosphorylated EML4-ALK fusion polypeptide v1 band was detected at the location of about 130 kDa under the condition of ATP addition, and the amount of phosphorylation was increased by about 205 folds compared to no-ATP addition.

In addition, the phosphorylation activity toward a peptide substrate was investigated using a kinase activity detection kit (HTRF KinEASE-TK; Cisbio Inc.). Using TK substrate 1, which was included in the kit, as the substrate, and after adding no ATP or 100 µM ATP, the mixtures were reacted at room temperature for 1 hour, and the count of HTRF was detected as recommended by the Kits manufacturer. As the result it became clear that the count of HTRF (that is, phosphorylation of the peptide substrate) was increased by about 12 times by the addition of ATP compare to no addition of ATP. As shown above, the in vitro kinase activity of the EML4-ALK fusion polypeptide v1 can be detected using anti-phosphorylated ALK antibody and the kinase activity detection kit.

(3) Inhibitory Effect of Compounds Against the In Vitro Kinase Activity of the EML4-ALK Fusion Polypeptide v1

The inhibitory effect of compound A-D against the in vitro kinase activity of the EML4-ALK fusion polypeptide v1 was investigated using anti-phosphorylated ALK antibody and the kinase activity detection kit. Respective compounds were added to the reaction solution containing the EML4-ALK fusion polypeptide v1 at a final concentration of 10 µM or 10 nM, and then the reaction was carried out with or without the addition of ATP. The rest of the operations were carried out according to the method (2) described above. In the absence of the compound, the phosphorylation count without ATP addition and with ATP addition was assumed to be 100% inhibition and 0% inhibition, respectively. The inhibition (%) of the kinase activity of the EML4-ALK fusion polypeptide v1 by a compound was calculated by the following formula.

[Kinase activity inhibition (%) by a compound]=(1−[phosphorylation count when the compound and ATP were added−phosphorylation count when the compound was not added and ATP was not added]/[phosphorylation count when the compound was not added and ATP was added−phosphorylation count when the compound was not added and ATP was not added])×100

As the result, it was found that compound A-D inhibited the phosphorylation activity of the purified EML4-ALK fusion polypeptide v1 on itself and the peptide substrate (Table 1). Compound A and B could be selected as substances which inhibited the activity of the EML4-ALK fusion polypeptide v1 by 50% or more at a concentration of 10 µM or less, and compound C and D could be selected as substances which inhibited the activity of the EML4-ALK fusion polypeptide v1 by 50% or more at a concentration of 0.1 µM or less.

TABLE 1

| Compound | Final concentration | Inhibition on autophosphorylation | Inhibition on peptide substrate |
| --- | --- | --- | --- |
| A | 10 µM | 104% | 99% |
| B | 10 µM | 68% | 56% |
| C | 10 nM | 102% | 99% |
| D | 10 nM | 96% | 99% |

The above results indicated that screening (an in vitro type screening) for a substance which inhibits the activity of the polypeptide of the present invention could be performed by preparing the EML4-ALK fusion polypeptide and using the in vitro kinase activity as an index.

Figure 4:
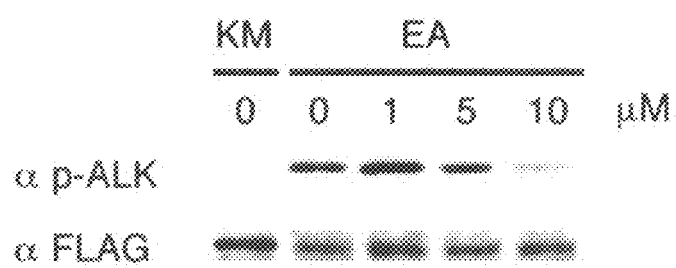
FIG. 4 shows the inhibitory effect of a EML4-ALK fusion polypeptide inhibitor (compound A) on intracellular autophosphorylation. "KM" indicates when EML4-ALK (K589M) expressing cells were used, and "EA" shows when v1 expressing BA/F3 cells were used. "αp-ALK" (upper panel) shows the result of the immunoblotting when anti-phosphorylated ALK antibody was used, and "αFLAG" (lower panel) shows the result of the immunoblotting when anti-FLAG antibody was used.

(4) Inhibitory Effect of EML4-ALK Fusion Polypeptide v1 Inhibitors on Intracellular Autophosphorylation (4-1) BA/F3 Cells Compound A (1 µM, 5 µM and 10 µM) was added to the culture medium of v1 expressing BA/F3 cells (Example 5(1)) or not added, and cultured for 3 hours. In addition, BA/F3 cells expressing FLAG-EML4-ALKv1 (K589M) were produced using pMX-iresCD8 vector in which EML4-ALK (K589M) was integrated so that FLAG can be added, and cultured. After culturing, cells were counted and the level of phosphorylation of tyrosine of EML4-ALK fusion polypeptide v1 was measured by immunoblotting using anti-phosphorylated ALK antibody. Further, for the same transfer membrane, immunoblotting analysis by anti-FLAG tag antibody (Eastman Kodak Inc.) was carried out, and total protein quantity of the FLAG attached EML4-ALK fusion polypeptide v1 was measured. As shown in the upper part of FIG. 4, tyrosine phosphorylation level of the EML4-ALK fusion polypeptide v1 was detected in v1 expressing BA/F3 cells, but no tyrosine phosphorylation was detected when EML4-ALK (K589M) was expressed. This fact indicates that the tyrosine phosphorylation of the EML4-ALK fusion polypeptide v1 detected in BA/F3 cells is an autophosphorylation by the EML4-ALK fusion polypeptide v1 itself. Also, it has been confirmed that compound A inhibits the intracellular autophosphorylation of the EML4-ALK fusion polypeptide v1 in a concentration-dependent manner. In addition, it has been shown that the amount of protein expression itself of the EML4-ALK fusion polypeptide v1 in all the samples has been almost constant (FIG. 4, lower part).

Inhibitory effect of compound B-D on the intracellular autophosphorylation was examined in a similar manner as described above. However, the culturing time after the addition of the compounds was 6 hours, and the total protein amount of the EML4-ALK fusion polypeptide v1 was measured using anti-ALK antibody. In addition, the amount of phosphorylation was calculated by quantitating as in Example 7(2). Also, for compound A, the amount of phosphorylation was calculated by quantitating in experiment under this condition. The rate of inhibition was calculated from the amount of phosphorylation when the compound was added, using the value when the compound was not added (the solvent of the compound, DMSO was added) as a control (0% inhibition). Every compound clearly inhibited the kinase activity of the EML4-ALK fusion polypeptide v1 in BA/F3 cells (Table 2). Compound A and B can be selected as the substance which inhibit the EML4-ALK fusion polypeptide v1 activity by 50% or more at a concentration of 10 μM or less, and compound C and D can be selected as the substance which inhibit the EML4-ALK fusion polypeptide v1 activity by 50% or more at a concentration of 0.1 μM or less, and it has been demonstrated that substances which inhibit the activity of the polypeptide of the present invention can be screened (cell type screening).

(4-2) 3T3 Cells

In a similar manner as in (4-1) except compound A-D were added to v1 expressing 3T3 cells (Example 6(1)) at 10 μM or 10 nM and cultured for 4 hours, the amount of phosphorylation of tyrosine of EML4-ALK fusion polypeptide v1 and the total protein amount of the EML4-ALK fusion polypeptide v1 were measured, and the inhibition rate of respective compounds on intracellular kinase activity was calculated. Each compound inhibited clearly the kinase activity of the EML4-ALK fusion polypeptide v1 in the v1 expressing 3T3 cells (Table 2). It became clear that various cells such as BA/F3 cells, 3T3 cells and the like can be used as cells expressing the polypeptide of the present invention in the cell type screening method of the present invention.

TABLE 2

| Compound | Final concentration | Inhibition on autophosphorylation (BA/F3 cells) | Inhibition on autophosphorylation (3T3 cells) |
|---|---|---|---|
| A | 10 μM | 74% | 82% |
| B | 10 μM | 77% | 49% |
| C | 10 nM | 84% | 77% |
| D | 10 nM | 90% | 86% |

The above results indicated that the kinase activity inhibiting compound of the EML4-ALK fusion polypeptide v1 activity can be obtained by using as an index the autophosphorylation in the cells expressing the EML4-ALK fusion polypeptide v1.

Example 8

Growth Inhibitory Effect of the Inhibitors of EML4-ALK Fusion Polypeptide on Cells Expressing the EML4-ALK Fusion Polynucleotide v1

(1) Growth Potential of v1 Expressing BA/F3

Figure 5:
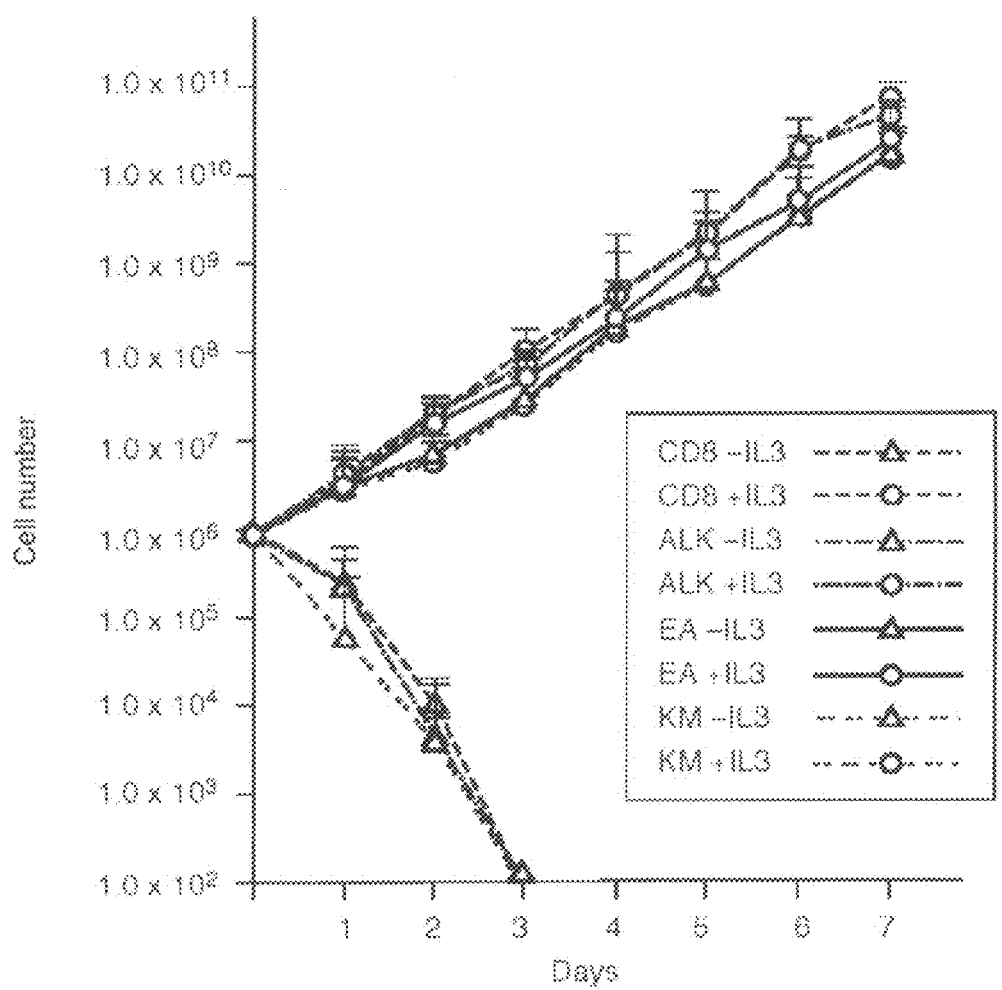
FIG. 5 shows the growth potential of cells which express CD8 protein only (CD8), or co-express CD8 and ALK (ALK), CD8 and EML4-ALK fusion polypeptide v1 (EA) or CD8 and EML4-ALK (K589M) (KM) in the presence (+IL-3) or absence (−IL-3) of IL-3. The horizontal axis of the figure is time course (Days) and the vertical axis is the cell number.

For growth of BA/F3 cells expressing only CD8 protein (Example 5(1)), BA/F3 cells expressing CD8 as well as ALK, the EML4-ALK fusion polypeptide v1 (Example 5(1)) or the EML4-ALK (K589M) defecting kinase activity, the change in the number of cells starting from 8×10⁵ cells in the time course was counted in the presence or absence of a growth factor IL-3. The results are shown in FIG. 5. The v1 expressing BA/F3 cells can grow with or without IL-3. However BA/F3 cells expressing only CD8 did grow in the presence of IL-3 but died rapidly when IL-3 was removed. This fact indicates that the EML4-ALK fusion polynucleotide v1 has an activity as oncogene. Further, cells expressing the full length human ALK and BA/F3 cells expressing EML4-ALK (K589M) that defect kinase activity similarly died in the absence of IL-3. These results indicate that cells obtain the growth potential, even in the absence of the growth factor, by expressing the EML4-ALK fusion polypeptide v1 and that the growth potential is dependent on the kinase activity of the EML4-ALK fusion polypeptide v1. BA/F3 cells expressing the full length ALK was obtained according to Example 5(1) and Example 6(1).

(2) Growth Inhibitory Effect of the Inhibitors of the EML4-ALK Fusion Polypeptide on v1 Expressing BA/F3 Cells Next, compound A, which is a substance that inhibits the EML4-ALK fusion polypeptide v1, was added to BA/F3 cells which obtained the IL-3 independent growth potential by expressing the EML4-ALK fusion polypeptide v1, and its effect on cell growth was investigated. When compound A was added at 1 nM, 5 nM or 10 nM, or not added (0 μM) to the control, CD8 expressing BA/F3 cells, which grow in the presence of IL-3 and the cell growth was measured, cells could grow although a slight growth inhibition was observed as shown in FIG. 6(*a*). On the other hand, when compound A was added to v1 expressing BA/F3 cells which were growing in the absence of IL-3, the cell growth was markedly inhibited by concentration-dependence of compound A and cell death was induced as shown in FIG. 6(*b*). That is, it was confirmed that cells, growing dependently on the EML4-ALK fusion polynucleotide (oncogene), were killed by an inhibitor of the EML4-ALK fusion polypeptide v1.

(3) Inhibitory Effect of the Inhibitors of EML4-ALK Fusion Polypeptide on Anchorage Independent Growth of Cells Expressing the EML4-ALK Fusion Polypeptide v1 and the Full Length ALK Polypeptide Measurement for anchorage independent cell growth (colony method, etc) has been known to be a system for investigating an antitumor effect (pharmacologic effect) of compounds (Clinical Oncology, second edition, Cancer and Chemotherapy Publishers Inc.). In place of the colony method, there is a following method using spheroid plates for measuring the growth of non-attached cells.

The v1 expressing 3T3 cells (Example 6(1)) and one of the human glioma cells expressing the full length ALK polypeptide and not expressing EML4-ALK fusion polynucleotide endogenously, U-87 MG cells, were seeded to a 96 well spheroid plate (Sumilon Celltight Spheroid 96U, Sumitomo Bakelite Inc.) at 3000 cells per well in a medium containing 10% fetal bovine serum (DMEM for v1 expressing 3T3 cells and RPMI 1640 for U-87MG). Under 5% $CO_2$, cells were cultured overnight at 37° C., and then compound A or B was added to a final concentration of 10 μM, compound C or D was added to a final concentration of 10 nM and as a negative control the solvent of the compounds, DMSO, was added to make the same concentration as the compounds. At the same time, cells were counted before the addition of drugs (Day 0). Then, cells were cultured under 5% $CO_2$, at 37° C. for 3 days, mixed with a reagent for measuring cell number (CellTiter-Glo™ Luminescent Cell Viability Assay; Promega Inc.) stirred for 20 minutes, and the measurements (day 3) were carried out using a luminometer (ML3000 microtiter plate luminometer; Dynatech Laboratories Inc.). The results show that all the compounds had growth inhibitory activity on v1 expressing 3T3 cells but almost no inhibitory activity on U-87MG cells. The inhibition rate of the compounds was calculated assuming the cell number at Day 0 and Day 3 were 100% inhibition and 0% inhibition, respectively (Table 3).

TABLE 3

| Compound | Final concentration | v1 expressing 3T3 cells | U-87MG cell |
|---|---|---|---|
| A | 10 μM | 106% | 15% |
| B | 10 μM | 91% | 34% |
| C | 10 nM | 131% | −2% |
| D | 10 nM | 135% | −2% |

Above results indicate that compound A-D inhibited the anchorage independent cell growth of v1 expressing 3T3 cells by inhibiting the kinase activity of the EML4-ALK fusion polypeptide v1. In addition, it became clear that these compounds could not inhibit the anchorage independent cell growth of U-87MG cells expressing the full length ALK polypeptide. These results indicate that the inhibitors of EML4-ALK fusion polypeptide can inhibit the growth of cancer cells and tumors which express the EML4-ALK fusion polypeptide.

(4) Preparation of siRNA to the EML4-ALK Fusion Polynucleotide v1 siRNAs, which were composed of a sense strand consisting of the base sequences represented by SEQ ID NO: 111, 113, 115, 117, 119, or 121, and an antisense strand consisting of the base sequences represented by SEQ ID NO: 112, 114, 116, 118, 120, or 122, were prepared as the siRNA (siRNA-1 to siRNA-6) which have a 100% homology to the fusion area of the EML4-ALK fusion polypeptide v1 and is expected to have inhibitory activity on the expression of EML4-ALK fusion polypeptide v1. In addition, siRNAs composed of a sense strand consisting of the base sequences represented by SEQ ID NO: 123 or 125 and an antisense strand consisting of the base sequence represented by SEQ ID NO: 124 or 126 were designed and prepared, as the siRNA (siRNA-7, siRNA-8) which shows 100% homology to the ALK area of the EML4-ALK fusion polypeptide v1 and are expected to have an inhibitory effect on the expression of the ALK gene, using an siRNA sequence design system (Commercial siDirect (registered trade mark) RNAi Inc.). It has been confirmed by the siRNA sequence design system (Commercial siDirect (registered trade mark) RNAi Inc.) that the base sequences corresponding to siRNA-1 to siRN-8 do not show a 100% homology to the gene other than the EML4-ALK fusion polynucleotide and ALK genes. For control experiments to investigate the influence of non specific siRNA, siRNA composed of a sense strand consisting of a base sequence represented by SEQ ID NO: 127 and an antisense strand consisting of a base sequence represented by SEQ ID NO: 128 was prepared as siRNA (siRNA-9) corresponding to a base sequence not present in mammalian cells. siRNA-1 is a product of annealing SEQ ID NO: 111 (sense strand) and SEQ ID NO: 112 (antisense strand), and siRNA-2 and others are the same (FIG. 7).

(5) Inhibitory Effect of siRNA on mRNA Expression of the EML4-ALK Fusion Polynucleotide and ALK Gene in Cells Expressing the EML4-ALK Fusion Polynucleotide v1 and Full Length ALK The v1 expressing 3T3 cells and U-87MG cells were seeded to 12 well plates (IWAKI; Asahi techno glass corp.) at 50,000 cells and 150,000 cells, respectively. Four hours later, using a transfection reagent (Lipofectamine RNAiMax; Invitrogen Inc.), siRNA-1 to siRNA-9 were prepared to a final concentration of 20 nM and transfected to cells according to the attached instruction. In addition, as a control no siRNA transfection samples were prepared. After 72 hours, the medium was removed, and total RNA was extracted using an RNA purification kit (RNeasy Mini Kit; QIAGEN Inc.) according to the attached instruction, and cDNA was prepared using a cDNA synthesizing kit (ThermoScript RT-PCR System; Invitrogen Inc.) according to the attached instruction.

The amount of expressed mRNA of the EML4-ALK fusion polynucleotide v1 in v1 expressing 3T3 cells and the amount of mRNA of the ALK gene in U-87MG cells were quantitated using a quantitative PCR reagent (Power SYBR Green PCR Master Mix; Applied Biosystems Inc.) The PCR reaction was carried out as follows: after 10 minutes incubation at 95° C., 45 cycles of 95° C. for 15 seconds and 60° C. for 60 seconds, and then one cycle of 95° C. for 15 seconds, 60° C. for 15 seconds and 95° C. for 15 seconds to complete the reaction. In addition, to calibrate the amount of expression, the amount of expression of the mouse cyclophilin B gene and the human GAPDH gene was similarly quantitated for v1 expressing 3T3 cells and U-87MG cells, respectively. Analyses were carried out using a sequence detector (ABI PRISM 7900 Sequence Detection System; Perkin-Elmer Applied Biosystems Inc.).

Oligo nucleotides consisting of the base sequences represented by SEQ ID NO: 44 and 48, SEQ ID NO: 50 and 56, SEQ ID NO: 44 and 48 and SEQ ID NO: 12 and 13 were used as the primer sets that specifically recognize the EML4-ALK fusion polynucleotide v1, the mouse cyclophilin B gene, the human ALK gene and the human GAPDH gene. Also, to obtain a standard curve to calculate the amount of respective mRNA, PCR was performed using human genomic DNA (Clontech) as a template for EML4-ALK fusion polynucleotide v1, human ALK and human GAPDH, and using mouse genomic DNA (Clontech) as a template for mouse cyclophilin B and the aforementioned primer sets under the same condition. Since a primer set corresponding to human ALK polynucleotide exon 29 was used to detect the EML4-ALK fusion polynucleotide v1, the standard curve can be obtained using human genomic DNA. The expression amount of the EML4-ALK fusion polynucleotide v1 and the human ALK gene in respective samples was calibrated with the expression amount of the mouse cyclophilin B gene and the human GAPDH gene to obtain the calibrated expression amount. Further, assuming the respective calibrated expression amount of the EML4-ALK fusion polynucleotide v1 and the human ALK gene in the absence of siRNA to be 100%, the relative expression amount of the calibrated expression amount of the EML4-ALK fusion polynucleotide v1 andt human ALK gene was determined and the inhibition rate for expression was calculated when respective siRNAs were transfected (Table 4).

As the result, siRNA-1 to siRNA-8, which correspond to the EML4-ALK fusion polynucleotide v1, inhibited the expression of the EML4-ALK fusion polynucleotide by 50% or more. For the human ALK gene, siRNA-7 and siRNA-8, which correspond to the human ALK gene, inhibited by 50% or more. The negative control, siRNA-9, did not demonstrate strong expression inhibitory effect on the EML4-ALK fusion polynucleotide and the human ALK gene. These results demonstrate that substances inhibiting the expression of the EML4-ALK fusion polynucleotide can be screened.

TABLE 4

| siRNA | Inhibition rate for EML4-ALK gene expression (v1 expressing 3T3 cells) | Inhibition rate for ALK gene expression (U-87 MG cells) |
|---|---|---|
| siRNA-1 | 80% | −12% |
| siRNA-2 | 66% | 11% |
| siRNA-3 | 62% | 10% |
| siRNA-4 | 86% | 22% |
| siRNA-5 | 76% | −22% |
| siRNA-6 | 69% | 15% |
| siRNA-7 | 67% | 66% |
| siRNA-8 | 70% | 58% |
| siRNA-9 | 29% | −31% |
| siRNA not introduced | 0% | 0% |

(6) Inhibitory Effect of siRNA on Expression and Autophosphorylation of the EML4-ALK Fusion Polypeptide v1 in v1 Expressing 3T3 Cells.

By the similar method described before, v1 expressing 3T3 cells were seeded to 12 well plates at 50,000 cells per well, and 4 hours later, siRNA-1 to siRNA-9 were transfected. In addition, cells to which no siRNA was transfected were prepared as a control. After 72 hours of the transfection, the medium was removed, and the autophosphorylation of the intracellular EML4-ALK fusion polypeptide v1 and protein amount of the EML4-ALK fusion polypeptide v1 were quantitated by the similar method as in Example 7(4). Also, to confirm that total protein in each sample for measurement was the same amount, the actin protein was quantitated using anti-actin antibody (SIGMA-ALDRICH Inc.). siRNA-1 to siRNA-8 were clearly inhibited the expression of the EML4-ALK fusion polypeptide v1 and the kinase activity in the v1 expressing 3T3 cells.

(7) Growth Inhibitory Effect of siRNA on v1 Expressing 3T3 Cells and Full Length ALK Expressing Cells Cell growth inhibition rate was calculated with or without transfecting siRNA by the similar method as in Example 8(3), except that each siRNA was added to 96 well spheroid plates beforehand and then v1 expressing 3T3 cells and U-87MG cells were seeded and cultured for 3 days.

Results of these experiments are shown in Table 5. Each siRNA (siRNA-1 to siRNA-8), which had been demonstrated to have inhibitory effect on the expression of the EML4-ALK fusion polypeptide v1 in Example 8(5) (6), strongly inhibited anchorage independent growth of v1 expressing 3T3 cells. Since the cell number of v1 expressing 3T3 cells, to which siRNA-1, 3, 4 and 5 were transfected, was lower at the measuring time (Day 3) than when siRNA was transfected (Day 0) resulting in the growth inhibition rate being over 100%, cell death is believed to have been induced. On the other hand, siRNA-7 and siRNA-8 were shown to inhibit the expression of the ALK gene in Example 8(5) but did not inhibit the growth of U-87MG cells expressing the full length ALK. siRNA-1 to siRNA-6 did not show growth inhibition on U-87MG cells and the negative control, siRNA-9, did not inhibit the growth of v1 expressing 3T3 cells and U-87MG cells.

TABLE 5

| siRNA | v1 expressing 3T3 cells growth inhibition rate | U-87MG cell growth inhibition rate |
| --- | --- | --- |
| siRNA-1 | 110% | −13% |
| siRNA-2 | 94% | 25% |
| siRNA-3 | 108% | −21% |
| siRNA-4 | 120% | −8% |
| siRNA-5 | 110% | −13% |
| siRNA-6 | 97% | 16% |
| siRNA-7 | 87% | 15% |
| siRNA-8 | 94% | −21% |
| siRNA-9 | −35% | −16% |
| siRNA not introduced | 0% | 0% |

From the above results, it became clear that, by transfecting siRNA which is against the EML4-ALK fusion polynucleotide v1 to cancer cells expressing the EML4-ALK fusion polynucleotide v1, the expression of the EML4-ALK fusion polynucleotide v1 mRNA is inhibited resulting in the reduction of the EML4-ALK fusion polypeptide and in the inhibition of autophosphorylation causing the growth inhibition of cancer cells. Also, for cancer cells expressing the full length ALK, the growth inhibition did not occur when the expression of ALK was inhibited. From the above results, it became clear that the siRNA against the EML4-ALK fusion polynucleotide v1, for example, siRNA-1 to siRNA-8, is useful as a therapeutic agent against the tumor expressing the EML4-ALK fusion polynucleotide for the EML4-ALK fusion polynucleotide positive patients.

(8) Anti-Tumor Test for Inhibitors of the EML4-ALK Fusion Polypeptide Against v1 Expressing 3T3 Cells $3 \times 10^6$ cells of v1 expressing 3T3 cells suspended in PBS were inoculated subcutaneously by injection to the back of 5 weeks old male BALB/c nude mice (Japan Charles River Inc.). After 7 days of the inoculation, the administration of compound C, an inhibitor of the EML4-ALK fusion polypeptide (Table 1 to 3), was initiated. The test was conducted in the solvent group and compound C group, 4 animals per group. Compound C was dissolved in a solvent composed of 10% 1-methyl-2-pyrrolidinone (SIGMA-ALDRICH Inc.)/90% polyethylene glycol 300 (Fluka Inc.) and administered orally at the dose of 10 mg/kg. Administrations were performed once a day for 14 days, and body weight and tumor size were measured every other day. Tumor volume was calculated using the following formula.

[Tumor volume (mm$^3$)]=[Tumor major axis (mm)]× [tumor minor axis (mm)]$^2$×0.5

Assuming the tumor volume of the solvent group on the day of starting and the day of finishing administration was 100% inhibition and 0% inhibition, respectively, the inhibition rate of compound C was calculated. The results indicated that compound C inhibited the growth of v1 expressing 3T3 cells (tumor) by 103%.

The antitumor effect of compound D was investigated by the similar procedure with the following exceptions. The administration of the compound D was started after 6 days of the inoculation and carried out once a day for 10 days, and then the tumor size was measured. Compound D inhibited the growth of v1 expressing 3T3 cells (tumor) by 101%.

(9) Kinase Inhibitory Effect by Repeated Administrations of the Inhibitors of EML4-ALK Fusion Polypeptide to v1 Expressing 3T3 Tumor The kinase inhibitory effect of compound C was observed by a similar manner as in Example 8(8) with the following exceptions. $1 \times 10^6$ cells of v1 expressing 3T3 cells were inoculated and the administration of compound C was initiated after 13 day of the inoculation. The test was conducted in the solvent group and the compound C group, 3 animals for each group. The administrations were carried out once a day for 3 days. Animals were dissected 4 hours after the last administration, and the tumor was extirpated. Then, protein extracts were prepared from the tissues and immunoblotting was carried out using anti-phosphorylated ALK antibody. The results indicate that in the compound C group, tyrosine autophosphorylation of the EML4-ALK fusion polypeptide v1 in the tumor was significantly decreased compared to the solvent group. From this result it was confirmed that the anti-tumor effect of compound C in the animal model described above was based on the kinase inhibitory effect of the EML4-ALK fusion polypeptide v1 in the tumor.

Example 9

Detection of the EML4-ALK Fusion Polypeptide v1

A method for detecting the EML4-ALK fusion polypeptide v1 in cells was constructed as follows. The v1 expressing 3T3 cells and U-87MG cells were cultured. After washing 3 times with PBS, cells were lysed with the lysis solution (Example 7(1)). To 4 mg of the supernatant obtained after centrifugation, anti-EML4 antibody (Cell Signaling Inc.) was added and reacted overnight at 4° C. Then, protein G beads (Protein G Sepharose 4 Fast Flow; GE Healthcare Inc.) were added and immunoprecipitation was carried out for 2 hours. After centrifugation, the precipitates were washed 3 times with the washing solution (Example 7(1)) and suspended in an SDS dissolving solution. The supernatant was subjected to immunoblotting using anti-ALK antibody. As the result, the EML4-ALK fusion polypeptide v1 was detected in the immunoprecipitates of v1 expressing 3T3 cells but not detected in U-87MG cells. From the results described above, it became possible to detect the presence of the EML4-ALK fusion polypeptide v1 in cancer cells and cancer tissues expressing the EML4-ALK fusion polypeptide v1 using anti-EML4 antibody and anti-ALK antibody in combination, and it became clear that the EML4-ALK fusion polypeptide v1 positive cancer patients can be determined.

Example 10

Analysis of the EML4-ALK Fusion Polypeptide v2

(1) Construction of an Expression Vector of EML4-ALK Fusion Polypeptide v2

By consulting the non-patent document 8, using the full length EML4 polynucleotide cloned to pT7Blue as a template, an oligonucleotide represented by the SEQ ID NO: 129 which was provided with the cleavage sequence of restriction enzyme HindIII at the 5' terminus side of the start codon ATG of the EML4 gene and an oligonucleotide represented by SEQE ID NO: 130 which was designed to contain the cleavage sequence of XhoI present in the EML4 gene as primers, and a DNA polymerase (Pyrobest DNA polymerase; Takara Bio Inc.), PCR (25 cycles of 94° C. for 20 seconds, 60° C. for 30 seconds and 72° C. for 1 minute) was carried out to obtain a PCR product of 238 bp. Using this PCR product as a template, an oligonucleotide represented by SEQ ID NO: 131 which was provided with the cleavage sequence of restriction enzyme XhoI at the 5' terminus and the aforementioned oligonucleotide represented by SEQ ID NO: 130 as primers, PCR was carried out in the same conditioned as described above to obtain a PCR product of 247 bp. This product was digested with restriction enzyme XhoI and ligated with restriction enzyme XhoI digested pCR2.1-TOPO vector in which the EML4-ALK fusion polynucleotide v2 produced in Example 4(1) was cloned to produce a vector in which the cleavage sequence of restriction enzyme HindIII was integrated at the 5' terminus side of the start codon of the EML4-ALK fusion polynucleotide v2 (EML4-ALKv2/pCR2.1).

EML4-ALKv2/pCR2.1 was digested with restriction enzyme HindIII, the EML4-ALK fusion polynucleotide v2 was excised, the both termini were blunted, an adapter (EcoRI-NotI-BamHI adaptor; Takara Bio Inc.) was then ligated to both termini, and the fragment was inserted to the EcoRI site of a retrovirus vector pMXS. This was designated as EML4-ALKv2/pMXS.

Also, EML4-ALKv2/pCR2.1 was digested with restriction enzyme HindIII and XbaI, the EML4-ALK fusion polynucleotide v2 was excised and inserted to the HindIII/XbaI site of an expression vector pcDNA3.1/Zeo (Invitrogen Inc.) which was modified so that the FLAG tag was attached to the N-terminus on expression to produce an expression plasmid for EML4-ALK fusion polypeptide v2 to which the FLAG tag was attached to the N terminus (FLAG-EML4-ALKv2/pcDNA3).

(2) Confirmation of an Intracellular Autophosphorylation Activity of the EML4-ALK Fusion Polypeptide v2 and Screening for the Substances which Inhibit its Activity To 293EBNA cells (Invitrogen Inc.) seeded in collagen I coated 24 well plates (IWAKI; Asahi techno glass corp.) at $1 \times 10^5$ cells per well in DMEM medium containing 10% fetal bovine serum, 100 ng of FLAG-EML4-ALKv2/pcDNA3 (Example 10(1) or pcDNA3 (blank vector) as a control was introduced using a transfection reagent (Lipofectamin2000; Invitrogen Inc.). After culturing for 20 hours, compound C or D each was added, and the culture was incubated for 4 hours and then cells were recovered. Expression of EML4-ALK fusion polypeptide v2 and tyrosine phosphorylation level were measured by immunoblotting using anti-ALK antibody and anti-phosphorylated ALK antibody.

As the results, in the immunoblot using anti-ALK antibody, a band was confirmed at the location of about 160 kDa where the EML4-ALK fusion polynucleotide v2 was expected to be present, and it was demonstrated that the amount of protein expression itself of the EML4-ALK fusion polynucleotide v2 was almost constant in all the samples. In addition, a band was confirmed at the same location in the immunoblot using anti-phosphorylated ALK antibody. The amount of phosphorylation was calculated by quantitating in a similar manner as in Example 7(2). The inhibition rate of phosphorylation by a compound was calculated from the amount of phosphorylation when the compound was added, assuming the value when no compound was added (the solvent of the compound, DMSO, was added) was 0% inhibition rate, and the value when the empty vector, pcDNA3, was introduced was 100% inhibition rate. The results indicate that each compound clearly inhibited the kinase activity of the EML4-ALK fusion polynucleotide v2 in 293EBNA cells (Table 6). Compound C and D could be selected as substances which inhibited the activity of the EML4-ALK fusion polypeptide v2 by 50% or more at a concentration of 0.1 µM or less. It is confirmed that screening for the substances inhibiting the activity of the polypeptide of the present invention (cell type screening) can be performed using the EML4-ALK fusion polypeptide v2 as well as the EML4-ALK fusion polypeptide v1.

TABLE 6

| Compound | Final concentration | Autophosphorylation inhibition (293EBNA cells) |
| --- | --- | --- |
| C | 10 nM | 90% |
| D | 10 nM | 95% |

(3) Investigation of Transformability and Tumorigenicity of EML4-ALK Fusion Polypeptide v2
(3-1) Focus Formation Assay By a similar manner described as in Example 6(1), the focus forming ability of EML4-ALK fusion polynucleotide v2 was investigated using EML4-ALKv2/pMXS (Example 10(1)). As a result, transformed foci of 3T3 cells were observed 21 days after transfection.
(3-2) Tumorigenicity in Nude Mice FLAG-EML4-ALKv2/pcDNA3 (Example 10(1)) was transfected into 3T3 cells using a transfection regent (FuGENE HD; Roche Diagnostics Inc.) according to the attached instruction. The EML4-ALK fusion polynucleotide v2 stably expressing 3T3 cells were established by resistance to 80 µg/ml zeocin. The expression of EML4-ALK fusion polynucleotide v2 in the 3T3 cells was confirmed by immunoblotting using anti-ALK antibody and anti-phosphorylated ALK antibody. The 3T3 cells in which EML4-ALK fusion polypeptide v2 is expressed are designated as the v2 expressing 3T3 cells. The v2 expressing 3T3 cells were inoculated subcutaneously to 4 weeks old male BALB/c nude mice (Japan Charles River Inc.) at $2 \times 10^6$ cells/mouse and observed for 15 days. As in the case of the v1 expressing cells (the lower section of the FIG. 3), it turned out that tumor was also formed in EML4-ALK fusion polypeptide v2 expressing 3T3 cells. The tumor formation number was 4 among 4.

From above results, it was confirmed that the EML4-ALK fusion polynucleotide v2, like the EML4-ALK fusion polynucleotide v1, is also an oncogene which codes for the polypeptides having the transformability and tumorigenicity to 3T3 cells.

What is claimed is:

1. A cDNA encoding a polypeptide comprising the amino acid sequence represented by SEQ ID NO: 2 or 7 and having a kinase activity.

2. An expression vector comprising the cDNA according to claim 1.

3. A cell transformed with the expression vector according to claim 2.

4. A method for producing an isolated polypeptide comprising the amino acid sequence represented by SEQ ID NO: 2 or 7 and having a kinase activity, comprising culturing a transformed cell according to claim 3 under conditions suitable for polypeptide expression and collecting the polypeptide from the cell.

* * * * *

SEQUENCE LISTING

```
<160> NUMBER OF SEQ ID NOS: 131

<210> SEQ ID NO 1
<211> LENGTH: 3900
<212> TYPE: DNA
<213> ORGANISM: Homo sapiens
<220> FEATURE:
<220> FEATURE:
<221> NAME/KEY: CDS
<222> LOCATION: (271)..(3447)

<400> SEQUENCE: 1
ggcggcgcgg cgcggcgctc gcggctgctg cctgggaggg aggccgggca ggcggctgag      60
cggcgcggct ctcaacgtga cggggaagtg gttcgggcgg ccgcggctta ctaccccagg     120
gcgaacggac ggacgacgga ggcgggagcc ggtagccgag ccgggcgacc tagagaacga     180
gcgggtcagg ctcagcgtcg gccactctgt cggtccgctg aatgaagtgc ccgcccctct     240
gagcccggag cccggcgctt tccccgcaag atg gac ggt ttc gcc ggc agt ctc     294
                                  Met Asp Gly Phe Ala Gly Ser Leu
                                    1               5 gat gat agt att tct gct gca agt act tct gat gtt caa gat cgc ctg      342
Asp Asp Ser Ile Ser Ala Ala Ser Thr Ser Asp Val Gln Asp Arg Leu
         10                  15                  20 tca gct ctt gag tca cga gtt cag caa caa gaa gat gaa atc act gtg      390
Ser Ala Leu Glu Ser Arg Val Gln Gln Gln Glu Asp Glu Ile Thr Val
 25                  30                  35                  40 cta aag gcg gct ttg gct gat gtt ttg agg cgt ctt gca atc tct gaa      438
Leu Lys Ala Ala Leu Ala Asp Val Leu Arg Arg Leu Ala Ile Ser Glu
                 45                  50                  55 gat cat gtg gcc tca gtg aaa aaa tca gtc tca agt aaa ggc caa cca      486
Asp His Val Ala Ser Val Lys Lys Ser Val Ser Ser Lys Gly Gln Pro
             60                  65                  70 agc cct cga gca gtt att ccc atg tcc tgt ata acc aat gga agt ggt      534
Ser Pro Arg Ala Val Ile Pro Met Ser Cys Ile Thr Asn Gly Ser Gly
         75                  80                  85 gca aac aga aaa cca agt cat acc agt gct gtc tca att gca gga aaa      582
Ala Asn Arg Lys Pro Ser His Thr Ser Ala Val Ser Ile Ala Gly Lys
 90                  95                 100 gaa act ctt tca tct gct gct aaa agt ggt aca gaa aaa aag aaa gaa      630
Glu Thr Leu Ser Ser Ala Ala Lys Ser Gly Thr Glu Lys Lys Lys Glu
105                 110                 115                 120 aaa cca caa gga cag aga gaa aaa aag gag gaa tct cat tct aat gat      678
Lys Pro Gln Gly Gln Arg Glu Lys Lys Glu Glu Ser His Ser Asn Asp
                125                 130                 135 caa agt cca caa att cga gca tca cct tct ccc cag ccc tct tca caa      726
Gln Ser Pro Gln Ile Arg Ala Ser Pro Ser Pro Gln Pro Ser Ser Gln
            140                 145                 150 cct ctc caa ata cac aga caa act cca gaa agc aag aat gct act ccc      774
Pro Leu Gln Ile His Arg Gln Thr Pro Glu Ser Lys Asn Ala Thr Pro
        155                 160                 165 acc aaa agc ata aaa cga cca tca cca gct gaa aag tca cat aat tct      822
Thr Lys Ser Ile Lys Arg Pro Ser Pro Ala Glu Lys Ser His Asn Ser
    170                 175                 180
```

| | | |
|---|---|---|
| tgg gaa aat tca gat gat agc cgt aat aaa ttg tcg aaa ata cct tca<br>Trp Glu Asn Ser Asp Asp Ser Arg Asn Lys Leu Ser Lys Ile Pro Ser<br>185                    190                    195                    200 | | 870 |
| aca ccc aaa tta ata cca aaa gtt acc aaa act gca gac aag cat aaa<br>Thr Pro Lys Leu Ile Pro Lys Val Thr Lys Thr Ala Asp Lys His Lys<br>                  205                    210                    215 | | 918 |
| gat gtc atc atc aac caa gaa gga gaa tat att aaa atg ttt atg cgc<br>Asp Val Ile Ile Asn Gln Glu Gly Glu Tyr Ile Lys Met Phe Met Arg<br>220                    225                    230 | | 966 |
| ggt cgg cca att acc atg ttc att cct tcc gat gtt gac aac tat gat<br>Gly Arg Pro Ile Thr Met Phe Ile Pro Ser Asp Val Asp Asn Tyr Asp<br>                  235                    240                    245 | | 1014 |
| gac atc aga acg gaa ctg cct cct gag aag ctc aaa ctg gag tgg gca<br>Asp Ile Arg Thr Glu Leu Pro Pro Glu Lys Leu Lys Leu Glu Trp Ala<br>250                    255                    260 | | 1062 |
| tat ggt tat cga gga aag gac tgt aga gct aat gtt tac ctt ctt ccg<br>Tyr Gly Tyr Arg Gly Lys Asp Cys Arg Ala Asn Val Tyr Leu Leu Pro<br>265                    270                    275                    280 | | 1110 |
| acc ggg gaa ata gtt tat ttc att gca tca gta gta gta cta ttt aat<br>Thr Gly Glu Ile Val Tyr Phe Ile Ala Ser Val Val Val Leu Phe Asn<br>                  285                    290                    295 | | 1158 |
| tat gag gag aga act cag cga cac tac ctg ggc cat aca gac tgt gtg<br>Tyr Glu Glu Arg Thr Gln Arg His Tyr Leu Gly His Thr Asp Cys Val<br>300                    305                    310 | | 1206 |
| aaa tgc ctt gct ata cat cct gac aaa att agg att gca act gga cag<br>Lys Cys Leu Ala Ile His Pro Asp Lys Ile Arg Ile Ala Thr Gly Gln<br>                  315                    320                    325 | | 1254 |
| ata gct ggc gtg gat aaa gat gga agg cct cta caa ccc cac gtc aga<br>Ile Ala Gly Val Asp Lys Asp Gly Arg Pro Leu Gln Pro His Val Arg<br>330                    335                    340 | | 1302 |
| gtg tgg gat tct gtt act cta tcc aca ctg cag att att gga ctt ggc<br>Val Trp Asp Ser Val Thr Leu Ser Thr Leu Gln Ile Ile Gly Leu Gly<br>345                    350                    355                    360 | | 1350 |
| act ttt gag cgt gga gta gga tgc ctg gat ttt tca aaa gca gat tca<br>Thr Phe Glu Arg Gly Val Gly Cys Leu Asp Phe Ser Lys Ala Asp Ser<br>                  365                    370                    375 | | 1398 |
| ggt gtt cat tta tgt gtt att gat gac tcc aat gag cat atg ctt act<br>Gly Val His Leu Cys Val Ile Asp Asp Ser Asn Glu His Met Leu Thr<br>                    380                    385                    390 | | 1446 |
| gta tgg gac tgg cag aag aaa gca aaa gga gca gaa ata aag aca aca<br>Val Trp Asp Trp Gln Lys Lys Ala Lys Gly Ala Glu Ile Lys Thr Thr<br>395                    400                    405 | | 1494 |
| aat gaa gtt gtt ttg gct gtg gag ttt cac cca aca gat gca aat acc<br>Asn Glu Val Val Leu Ala Val Glu Phe His Pro Thr Asp Ala Asn Thr<br>410                    415                    420 | | 1542 |
| ata att aca tgc ggt aaa tct cat att ttc ttc tgg acc tgg agc ggc<br>Ile Ile Thr Cys Gly Lys Ser His Ile Phe Phe Trp Thr Trp Ser Gly<br>425                    430                    435                    440 | | 1590 |
| aat tca cta aca aga aaa cag gga att ttt ggg aaa tat gaa aag cca<br>Asn Ser Leu Thr Arg Lys Gln Gly Ile Phe Gly Lys Tyr Glu Lys Pro<br>                  445                    450                    455 | | 1638 |
| aaa ttt gtg cag tgt tta gca ttc ttg ggg aat gga gat gtt ctt act<br>Lys Phe Val Gln Cys Leu Ala Phe Leu Gly Asn Gly Asp Val Leu Thr<br>460                    465                    470 | | 1686 |
| gga gac tca ggt gga gtc atg ctt ata tgg agc aaa act act gta gag<br>Gly Asp Ser Gly Gly Val Met Leu Ile Trp Ser Lys Thr Thr Val Glu<br>                  475                    480                    485 | | 1734 |
| ccc aca cct ggg aaa gga cct aaa gtg tac cgc cgg aag cac cag gag<br>Pro Thr Pro Gly Lys Gly Pro Lys Val Tyr Arg Arg Lys His Gln Glu<br>490                    495                    500 | | 1782 |

-continued

| | |
|---|---|
| ctg caa gcc atg cag atg gag ctg cag agc cct gag tac aag ctg agc<br>Leu Gln Ala Met Gln Met Glu Leu Gln Ser Pro Glu Tyr Lys Leu Ser<br>505                  510                515               520 | 1830 |
| aag ctc cgc acc tcg acc atc atg acc gac tac aac ccc aac tac tgc<br>Lys Leu Arg Thr Ser Thr Ile Met Thr Asp Tyr Asn Pro Asn Tyr Cys<br>              525                530               535 | 1878 |
| ttt gct ggc aag acc tcc tcc atc agt gac ctg aag gag gtg ccg cgg<br>Phe Ala Gly Lys Thr Ser Ser Ile Ser Asp Leu Lys Glu Val Pro Arg<br>         540                 545                550 | 1926 |
| aaa aac atc acc ctc att cgg ggt ctg ggc cat gga gcc ttt ggg gag<br>Lys Asn Ile Thr Leu Ile Arg Gly Leu Gly His Gly Ala Phe Gly Glu<br>555                  560                565 | 1974 |
| gtg tat gaa ggc cag gtg tcc gga atg ccc aac gac cca agc ccc ctg<br>Val Tyr Glu Gly Gln Val Ser Gly Met Pro Asn Asp Pro Ser Pro Leu<br>    570                575                580 | 2022 |
| caa gtg gct gtg aag acg ctg cct gaa gtg tgc tct gaa cag gac gaa<br>Gln Val Ala Val Lys Thr Leu Pro Glu Val Cys Ser Glu Gln Asp Glu<br>585                  590                595               600 | 2070 |
| ctg gat ttc ctc atg gaa gcc ctg atc atc agc aaa ttc aac cac cag<br>Leu Asp Phe Leu Met Glu Ala Leu Ile Ile Ser Lys Phe Asn His Gln<br>              605                610               615 | 2118 |
| aac att gtt cgc tgc att ggg gtg agc ctg caa tcc ctg ccc cgg ttc<br>Asn Ile Val Arg Cys Ile Gly Val Ser Leu Gln Ser Leu Pro Arg Phe<br>         620                 625                630 | 2166 |
| atc ctg ctg gag ctc atg gcg ggg gga gac ctc aag tcc ttc ctc cga<br>Ile Leu Leu Glu Leu Met Ala Gly Gly Asp Leu Lys Ser Phe Leu Arg<br>635                  640                645 | 2214 |
| gag acc cgc cct cgc ccg agc cag ccc tcc tcc ctg gcc atg ctg gac<br>Glu Thr Arg Pro Arg Pro Ser Gln Pro Ser Ser Leu Ala Met Leu Asp<br>              650                655               660 | 2262 |
| ctt ctg cac gtg gct cgg gac att gcc tgt ggc tgt cag tat ttg gag<br>Leu Leu His Val Ala Arg Asp Ile Ala Cys Gly Cys Gln Tyr Leu Glu<br>665                  670                675               680 | 2310 |
| gaa aac cac ttc atc cac cga gac att gct gcc aga aac tgc ctc ttg<br>Glu Asn His Phe Ile His Arg Asp Ile Ala Ala Arg Asn Cys Leu Leu<br>              685                690               695 | 2358 |
| acc tgt cca ggc cct gga aga gtg gcc aag att gga gac ttc ggg atg<br>Thr Cys Pro Gly Pro Gly Arg Val Ala Lys Ile Gly Asp Phe Gly Met<br>         700                 705                710 | 2406 |
| gcc cga gac atc tac agg gcg agc tac tat aga aag gga ggc tgt gcc<br>Ala Arg Asp Ile Tyr Arg Ala Ser Tyr Tyr Arg Lys Gly Gly Cys Ala<br>715                  720                725 | 2454 |
| atg ctg cca gtt aag tgg atg ccc cca gag gcc ttc atg gaa gga ata<br>Met Leu Pro Val Lys Trp Met Pro Pro Glu Ala Phe Met Glu Gly Ile<br>         730                 735                740 | 2502 |
| ttc act tct aaa aca gac aca tgg tcc ttt gga gtg ctg cta tgg gaa<br>Phe Thr Ser Lys Thr Asp Thr Trp Ser Phe Gly Val Leu Leu Trp Glu<br>745                  750                755               760 | 2550 |
| atc ttt tct ctt gga tat atg cca tac ccc agc aaa agc aac cag gaa<br>Ile Phe Ser Leu Gly Tyr Met Pro Tyr Pro Ser Lys Ser Asn Gln Glu<br>              765                770               775 | 2598 |
| gtt ctg gag ttt gtc acc agt gga ggc cgg atg gac cca ccc aag aac<br>Val Leu Glu Phe Val Thr Ser Gly Gly Arg Met Asp Pro Pro Lys Asn<br>         780                 785                790 | 2646 |
| tgc cct ggg cct gta tac cgg ata atg act cag tgc tgg caa cat cag<br>Cys Pro Gly Pro Val Tyr Arg Ile Met Thr Gln Cys Trp Gln His Gln<br>795                  800                805 | 2694 |
| cct gaa gac agg ccc aac ttt gcc atc att ttg gag agg att gaa tac<br>Pro Glu Asp Arg Pro Asn Phe Ala Ile Ile Leu Glu Arg Ile Glu Tyr<br>              810                815               820 | 2742 |

|     |     |     |     |     |     |     |     |     |     |     |     |     |     |     |     |      |
|---|---|---|---|---|---|---|---|---|---|---|---|---|---|---|---|---|
| tgc | acc | cag | gac | ccg | gat | gta | atc | aac | acc | gct | ttg | ccg | ata | gaa | tat | 2790 |
| Cys | Thr | Gln | Asp | Pro | Asp | Val | Ile | Asn | Thr | Ala | Leu | Pro | Ile | Glu | Tyr |      |
| 825 |     |     |     |     | 830 |     |     |     |     | 835 |     |     |     |     | 840 |      |

|     |     |     |     |     |     |     |     |     |     |     |     |     |     |     |     |      |
|---|---|---|---|---|---|---|---|---|---|---|---|---|---|---|---|---|
| ggt | cca | ctt | gtg | gaa | gag | gaa | gag | aaa | gtg | cct | gtg | agg | ccc | aag | gac | 2838 |
| Gly | Pro | Leu | Val | Glu | Glu | Glu | Glu | Lys | Val | Pro | Val | Arg | Pro | Lys | Asp |      |
|     |     |     |     |     | 845 |     |     |     |     | 850 |     |     |     |     | 855 |      |

|     |     |     |     |     |     |     |     |     |     |     |     |     |     |     |     |      |
|---|---|---|---|---|---|---|---|---|---|---|---|---|---|---|---|---|
| cct | gag | ggg | gtt | cct | cct | ctc | ctg | gtc | tct | caa | cag | gca | aaa | cgg | gag | 2886 |
| Pro | Glu | Gly | Val | Pro | Pro | Leu | Leu | Val | Ser | Gln | Gln | Ala | Lys | Arg | Glu |      |
|     |     |     | 860 |     |     |     |     | 865 |     |     |     |     | 870 |     |     |      |

|     |     |     |     |     |     |     |     |     |     |     |     |     |     |     |     |      |
|---|---|---|---|---|---|---|---|---|---|---|---|---|---|---|---|---|
| gag | gag | cgc | agc | cca | gct | gcc | cca | cca | cct | ctg | cct | acc | acc | tcc | tct | 2934 |
| Glu | Glu | Arg | Ser | Pro | Ala | Ala | Pro | Pro | Pro | Leu | Pro | Thr | Thr | Ser | Ser |      |
|     |     | 875 |     |     |     |     | 880 |     |     |     |     | 885 |     |     |     |      |

|     |     |     |     |     |     |     |     |     |     |     |     |     |     |     |     |      |
|---|---|---|---|---|---|---|---|---|---|---|---|---|---|---|---|---|
| ggc | aag | gct | gca | aag | aaa | ccc | aca | gct | gca | gag | gtc | tct | gtt | cga | gtc | 2982 |
| Gly | Lys | Ala | Ala | Lys | Lys | Pro | Thr | Ala | Ala | Glu | Val | Ser | Val | Arg | Val |      |
|     | 890 |     |     |     |     | 895 |     |     |     |     | 900 |     |     |     |     |      |

|     |     |     |     |     |     |     |     |     |     |     |     |     |     |     |     |      |
|---|---|---|---|---|---|---|---|---|---|---|---|---|---|---|---|---|
| cct | aga | ggg | ccg | gcc | gtg | gaa | ggg | gga | cac | gtg | aat | atg | gca | ttc | tct | 3030 |
| Pro | Arg | Gly | Pro | Ala | Val | Glu | Gly | Gly | His | Val | Asn | Met | Ala | Phe | Ser |      |
| 905 |     |     |     |     | 910 |     |     |     |     | 915 |     |     |     |     | 920 |      |

|     |     |     |     |     |     |     |     |     |     |     |     |     |     |     |     |      |
|---|---|---|---|---|---|---|---|---|---|---|---|---|---|---|---|---|
| cag | tcc | aac | cct | cct | tcg | gag | ttg | cac | agg | gtc | cac | gga | tcc | aga | aac | 3078 |
| Gln | Ser | Asn | Pro | Pro | Ser | Glu | Leu | His | Arg | Val | His | Gly | Ser | Arg | Asn |      |
|     |     |     | 925 |     |     |     |     | 930 |     |     |     |     | 935 |     |     |      |

|     |     |     |     |     |     |     |     |     |     |     |     |     |     |     |     |      |
|---|---|---|---|---|---|---|---|---|---|---|---|---|---|---|---|---|
| aag | ccc | acc | agc | ttg | tgg | aac | cca | acg | tac | ggc | tcc | tgg | ttt | aca | gag | 3126 |
| Lys | Pro | Thr | Ser | Leu | Trp | Asn | Pro | Thr | Tyr | Gly | Ser | Trp | Phe | Thr | Glu |      |
|     |     | 940 |     |     |     |     | 945 |     |     |     |     | 950 |     |     |     |      |

|     |     |     |     |     |     |     |     |     |     |     |     |     |     |     |     |      |
|---|---|---|---|---|---|---|---|---|---|---|---|---|---|---|---|---|
| aaa | ccc | acc | aaa | aag | aat | aat | cct | ata | gca | aag | aag | gag | cca | cac | gag | 3174 |
| Lys | Pro | Thr | Lys | Lys | Asn | Asn | Pro | Ile | Ala | Lys | Lys | Glu | Pro | His | Glu |      |
|     | 955 |     |     |     |     | 960 |     |     |     |     | 965 |     |     |     |     |      |

|     |     |     |     |     |     |     |     |     |     |     |     |     |     |     |     |      |
|---|---|---|---|---|---|---|---|---|---|---|---|---|---|---|---|---|
| agg | ggt | aac | ctg | ggg | ctg | gag | gga | agc | tgt | act | gtc | cca | cct | aac | gtt | 3222 |
| Arg | Gly | Asn | Leu | Gly | Leu | Glu | Gly | Ser | Cys | Thr | Val | Pro | Pro | Asn | Val |      |
| 970 |     |     |     |     | 975 |     |     |     |     | 980 |     |     |     |     |     |      |

|     |     |     |     |     |     |     |     |     |     |     |     |     |     |     |     |      |
|---|---|---|---|---|---|---|---|---|---|---|---|---|---|---|---|---|
| gca | act | ggg | aga | ctt | ccg | ggg | gcc | tca | ctg | ctc | cta | gag | ccc | tct | tcg | 3270 |
| Ala | Thr | Gly | Arg | Leu | Pro | Gly | Ala | Ser | Leu | Leu | Leu | Glu | Pro | Ser | Ser |      |
| 985 |     |     |     |     | 990 |     |     |     |     | 995 |     |     |     |     | 1000|      |

|     |     |     |     |     |     |     |     |     |     |     |     |     |     |      |
|---|---|---|---|---|---|---|---|---|---|---|---|---|---|---|
| ctg | act | gcc | aat | atg | aag | gag | gta | cct | ctg | ttc | agg | cta | cgt | cac | 3315 |
| Leu | Thr | Ala | Asn | Met | Lys | Glu | Val | Pro | Leu | Phe | Arg | Leu | Arg | His |      |
|     |     |     |     | 1005|     |     |     |     | 1010|     |     |     |     | 1015|      |

|     |     |     |     |     |     |     |     |     |     |     |     |     |     |     |      |
|---|---|---|---|---|---|---|---|---|---|---|---|---|---|---|---|
| ttc | cct | tgt | ggg | aat | gtc | aat | tac | ggc | tac | cag | caa | cag | ggc | ttg | 3360 |
| Phe | Pro | Cys | Gly | Asn | Val | Asn | Tyr | Gly | Tyr | Gln | Gln | Gln | Gly | Leu |      |
|     |     |     |     | 1020|     |     |     |     | 1025|     |     |     |     | 1030|      |

|     |     |     |     |     |     |     |     |     |     |     |     |     |     |     |      |
|---|---|---|---|---|---|---|---|---|---|---|---|---|---|---|---|
| ccc | tta | gaa | gcc | gct | act | gcc | cct | gga | gct | ggt | cat | tac | gag | gat | 3405 |
| Pro | Leu | Glu | Ala | Ala | Thr | Ala | Pro | Gly | Ala | Gly | His | Tyr | Glu | Asp |      |
|     |     |     | 1035|     |     |     |     | 1040|     |     |     |     | 1045|     |      |

|     |     |     |     |     |     |     |     |     |     |     |     |      |
|---|---|---|---|---|---|---|---|---|---|---|---|---|
| acc | att | ctg | aaa | agc | aag | aat | agc | atg | aac | cag | cct | ggg | ccc | 3447 |
| Thr | Ile | Leu | Lys | Ser | Lys | Asn | Ser | Met | Asn | Gln | Pro | Gly | Pro |      |
|     |     |     |     | 1050|     |     |     |     | 1055|     |     |     |     |      | tgagctcggt cacacactca cttctcttcc ttgggatccc taagaccgtg gaggagagag   3507 aggcaatcaa tggctccttc acaaaccaga gaccaaatgt cacgttttgt tttgtgccaa   3567 cctattttga agtaccacca aaaagctgt attttgaaaa tgctttagaa aggttttgag   3627 catgggttca tcctattctt tcgaaagaag aaaatatcat aaaaatgagt gataaataca   3687 aggcccagat gtggttgcat aaggttttta tgcatgtttg ttgtatactt ccttatgctt   3747 cttttaaatt gtgtgtgctc tgcttcaatg tagtcagaat tagctgcttc tatgtttcat   3807 agttggggtc atagatgttt ccttgccttg ttgatgtgga catgagccat ttgaggggag   3867 agggaacgga aataaggag ttatttgtaa tga   3900

```
<210> SEQ ID NO 2
<211> LENGTH: 1059
<212> TYPE: PRT
<213> ORGANISM: Homo sapiens

<400> SEQUENCE: 2

Met Asp Gly Phe Ala Gly Ser Leu Asp Asp Ser Ile Ser Ala Ala Ser
 1               5                  10                  15

Thr Ser Asp Val Gln Asp Arg Leu Ser Ala Leu Glu Ser Arg Val Gln
                20                  25                  30

Gln Gln Glu Asp Glu Ile Thr Val Leu Lys Ala Ala Leu Ala Asp Val
            35                  40                  45

Leu Arg Arg Leu Ala Ile Ser Glu Asp His Val Ala Ser Val Lys Lys
        50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Glu Gly
210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Leu Phe Asn Tyr Glu Glu Arg Thr Gln Arg His
290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
            340                 345                 350

Thr Leu Gln Ile Ile Gly Leu Gly Thr Phe Glu Arg Gly Val Gly Cys
        355                 360                 365

Leu Asp Phe Ser Lys Ala Asp Ser Gly Val His Leu Cys Val Ile Asp
        370                 375                 380
```

-continued

```
Asp Ser Asn Glu His Met Leu Thr Val Trp Asp Trp Gln Lys Lys Ala
385                 390                 395                 400

Lys Gly Ala Glu Ile Lys Thr Thr Asn Glu Val Val Leu Ala Val Glu
            405                 410                 415

Phe His Pro Thr Asp Ala Asn Thr Ile Ile Thr Cys Gly Lys Ser His
        420                 425                 430

Ile Phe Phe Trp Thr Trp Ser Gly Asn Ser Leu Thr Arg Lys Gln Gly
    435                 440                 445

Ile Phe Gly Lys Tyr Glu Lys Pro Lys Phe Val Gln Cys Leu Ala Phe
450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
            485                 490                 495

Val Tyr Arg Arg Lys His Gln Glu Leu Gln Ala Met Gln Met Glu Leu
        500                 505                 510

Gln Ser Pro Glu Tyr Lys Leu Ser Lys Leu Arg Thr Ser Thr Ile Met
    515                 520                 525

Thr Asp Tyr Asn Pro Asn Tyr Cys Phe Ala Gly Lys Thr Ser Ser Ile
530                 535                 540

Ser Asp Leu Lys Glu Val Pro Arg Lys Asn Ile Thr Leu Ile Arg Gly
545                 550                 555                 560

Leu Gly His Gly Ala Phe Gly Glu Val Tyr Glu Gly Gln Val Ser Gly
            565                 570                 575

Met Pro Asn Asp Pro Ser Pro Leu Gln Val Ala Val Lys Thr Leu Pro
        580                 585                 590

Glu Val Cys Ser Glu Gln Asp Glu Leu Asp Phe Leu Met Glu Ala Leu
    595                 600                 605

Ile Ile Ser Lys Phe Asn His Gln Asn Ile Val Arg Cys Ile Gly Val
610                 615                 620

Ser Leu Gln Ser Leu Pro Arg Phe Ile Leu Leu Glu Leu Met Ala Gly
625                 630                 635                 640

Gly Asp Leu Lys Ser Phe Leu Arg Glu Thr Arg Pro Arg Pro Ser Gln
            645                 650                 655

Pro Ser Ser Leu Ala Met Leu Asp Leu Leu His Val Ala Arg Asp Ile
        660                 665                 670

Ala Cys Gly Cys Gln Tyr Leu Glu Glu Asn His Phe Ile His Arg Asp
    675                 680                 685

Ile Ala Ala Arg Asn Cys Leu Leu Thr Cys Pro Gly Pro Gly Arg Val
690                 695                 700

Ala Lys Ile Gly Asp Phe Gly Met Ala Arg Asp Ile Tyr Arg Ala Ser
705                 710                 715                 720

Tyr Tyr Arg Lys Gly Gly Cys Ala Met Leu Pro Val Lys Trp Met Pro
            725                 730                 735

Pro Glu Ala Phe Met Glu Gly Ile Phe Thr Ser Lys Thr Asp Thr Trp
        740                 745                 750

Ser Phe Gly Val Leu Leu Trp Glu Ile Phe Ser Leu Gly Tyr Met Pro
    755                 760                 765

Tyr Pro Ser Lys Ser Asn Gln Glu Val Leu Glu Phe Val Thr Ser Gly
770                 775                 780

Gly Arg Met Asp Pro Pro Lys Asn Cys Pro Gly Pro Val Tyr Arg Ile
785                 790                 795                 800

Met Thr Gln Cys Trp Gln His Gln Pro Glu Asp Arg Pro Asn Phe Ala
```

```
                    805                 810                 815
Ile Ile Leu Glu Arg Ile Glu Tyr Cys Thr Gln Asp Pro Asp Val Ile
                820                 825                 830

Asn Thr Ala Leu Pro Ile Glu Tyr Gly Pro Leu Val Glu Glu Glu Glu
            835                 840                 845

Lys Val Pro Val Arg Pro Lys Asp Pro Glu Gly Val Pro Pro Leu Leu
    850                 855                 860

Val Ser Gln Gln Ala Lys Arg Glu Glu Arg Ser Pro Ala Ala Pro
865                 870                 875                 880

Pro Pro Leu Pro Thr Thr Ser Ser Gly Lys Ala Ala Lys Lys Pro Thr
                885                 890                 895

Ala Ala Glu Val Ser Val Arg Val Pro Arg Gly Pro Ala Val Glu Gly
            900                 905                 910

Gly His Val Asn Met Ala Phe Ser Gln Ser Asn Pro Pro Ser Glu Leu
        915                 920                 925

His Arg Val His Gly Ser Arg Asn Lys Pro Thr Ser Leu Trp Asn Pro
    930                 935                 940

Thr Tyr Gly Ser Trp Phe Thr Glu Lys Pro Thr Lys Lys Asn Asn Pro
945                 950                 955                 960

Ile Ala Lys Lys Glu Pro His Glu Arg Gly Asn Leu Gly Leu Glu Gly
                965                 970                 975

Ser Cys Thr Val Pro Pro Asn Val Ala Thr Gly Arg Leu Pro Gly Ala
            980                 985                 990

Ser Leu Leu Leu Glu Pro Ser Ser  Leu Thr Ala Asn Met Lys Glu Val
        995                 1000                1005

Pro Leu  Phe Arg Leu Arg His  Phe Pro Cys Gly Asn  Val Asn Tyr
    1010                1015                1020

Gly Tyr  Gln Gln Gln Gly Leu  Pro Leu Glu Ala Ala  Thr Ala Pro
    1025                1030                1035

Gly Ala  Gly His Tyr Glu Asp  Thr Ile Leu Lys Ser  Lys Asn Ser
    1040                1045                1050

Met Asn  Gln Pro Gly Pro
    1055

<210> SEQ ID NO 3
<211> LENGTH: 942
<212> TYPE: DNA
<213> ORGANISM: Homo sapiens

<400> SEQUENCE: 3
ggagatgttc ttactggaga ctcaggtgga gtcatgctta tatggagcaa aactactgta      60
gagcccacac ctgggaaagg acctaaaggt gtatatcaaa tcagcaaaca aatcaaagct     120
catgatggca gtgtgttcac actttgtcag atgagaaatg ggatgttatt aactggagga     180
gggaaagaca gaaaaataat tctgtgggat catgatctga atcctgaaag agaaatagag     240
gttcctgatc agtatggcac aatcagagct gtagcagaag gaaaggcaga tcaattttta     300
gtaggcacat cacgaaactt tattttacga ggaacattta atgatggctt ccaaatagaa     360
gtacagggtc atacagatga gctttgggt cttgccacac atcccttcaa agatttgctc     420
ttgacatgtg ctcaggacag gcaggtgtgc ctgtggaact caatggaaca caggctggaa     480
tggaccaggc tggtagatga accaggacac tgtgcagatt tcatccaagt ggcacagtg      540 gtggccatag aacgcactc aggcaggtgg tttgttctgg atgcagaaac cagagatcta     600
gtttctatcc acacagacgg gaatgaacag ctctctgtga tgcgctactc aatagatggt     660
```

| | | | | |
|---|---|---|---|---|
| accttcctgg | ctgtaggatc | tcatgacaac | tttatttacc | tctatgtagt | ctctgaaaat | 720 |
| ggaagaaaat | atagcagata | tggaaggtgc | actggacatt | ccagctacat | cacacacctt | 780 |
| gactggtccc | cagacaacaa | gtatataatg | tctaactcgg | gagactatga | aatattgtac | 840 |
| ttgtaccgcc | ggaagcacca | ggagctgcaa | gccatgcaga | tggagctgca | gagccctgag | 900 |
| tacaagctga | gcaagctccg | cacctcgacc | atcatgaccg | ac | | 942 |

<210> SEQ ID NO 4
<211> LENGTH: 3979
<212> TYPE: DNA
<213> ORGANISM: Homo sapiens

<400> SEQUENCE: 4

| | | | | | | |
|---|---|---|---|---|---|---|
| gtacagtatt | cttatattaa | actcatttct | ggtaattctc | acatagtact | ctttcagtcc | 60 |
| catctcttag | accaggagag | aaagagctgc | agtgtaacaa | tatgagcaag | tcaccaacat | 120 |
| accttttgtt | ttcagcattc | ttcataatct | tttttttaatg | aaattattta | tccagttatt | 180 |
| tattaagctt | atataaccca | catttgacta | tactgaacca | ttccctttag | gaagttaata | 240 |
| attagaaaga | aatgatatgg | atatatgtta | gtttaaaaag | tataaaggct | cactttcccc | 300 |
| tgagctggtt | ctgggatatc | tgttagagca | gaatgcatgg | ccatgtgata | aaatggaaga | 360 |
| gtggagagaa | aaggaataaa | ctcatagttc | aatccacttc | tccttttctt | tttcctcact | 420 |
| gcagcccttc | ttcccaacct | tagtgtaggg | gtccttggca | tccattcagc | tttacctcaa | 480 |
| atcagttttc | ctaaaaaaca | cagatttatt | cttaagtttt | atttgcaccc | aaatatacag | 540 |
| gtcctctttg | ccctttttcta | cggtaaatga | aaaaattaga | ggaaggacat | ggaaaataac | 600 |
| cttttttaaa | cccatttttt | cgttactatt | taagaataat | caaactttga | aaaaaatgtc | 660 |
| cagagtacca | tgtacttcct | tcagagtagg | aggttctaag | agaaaaattg | gagacctggt | 720 |
| tctaaaacca | gtgggccagg | agaagagaga | gattcttagc | agcaacaggt | ggtaacagta | 780 |
| gaaatagaac | tagctaggtc | agccagtcct | caataattca | ccaaaaaaaa | agtaagaaag | 840 |
| gaggtaatgg | ggaaatcacc | ctgagttttc | tgagacattt | ccctggggga | ttggcagggc | 900 |
| aacatgtcct | ttctcttgtt | cattcacctc | ccctaaacac | actggaacaa | caccttactt | 960 |
| ctctctctct | ctctctctct | ggagtccttg | catcagacca | tgaaaatcac | cctaagtgat | 1020 |
| ttatgaataa | gggaatccct | gttcgtgtgc | tcagaaagac | ccgatttaca | tatctgcctt | 1080 |
| ccccaataag | ctttccctgg | gctagcacag | tgtctggcat | ttgctattag | ctgtttgaaa | 1140 |
| actatttgtc | aaacattaag | gaaataactt | tcatcttaac | tttgggtgtc | aatgtaggag | 1200 |
| taaaagttga | gtagtattga | tgaaagcact | gttttcaccg | aaatgtggaa | tttaaatttc | 1260 |
| gcattactgt | tttcttatga | ctgcacagag | tttcatactg | tatttttag | gacagatatt | 1320 |
| cagatgctcc | ttgacttctg | gatggcatta | tatcccgata | aatctatcat | aatgtcaaaa | 1380 |
| aataataaat | tgaaccaaca | taagttaggc | actatctgta | cgaaattaat | gttttaatta | 1440 |
| aatgttttttc | aaatccattc | acctgaatgt | ctaagcttgg | cagttgaatt | agacctatta | 1500 |
| agaagtttaa | aacaagaagc | cttaaattgt | attaccattg | actcctatct | caatcattgg | 1560 |
| ccatatattc | ttagcctctt | tcgttcagtt | taggttcaaa | atttacacac | gagaagaatg | 1620 |
| gcagtgggtt | gagggttctt | aaaaaaataga | gttacaacaa | caatatatta | tcaactactt | 1680 |
| ttcccatttta | tttctctttt | cttttttttct | tattttttctt | tcctgggcac | atttacttag | 1740 |
| tatcagaaat | gccaggaaca | gcatagtcta | ttaaaacagt | gacttttaaa | ttgttcacga | 1800 |

```
atctccaaca ctgagcagaa tttgcgtata aatatacccct tttgttagcc ttaatatttg      1860
tgttcaggtt ggggacagga agaagaggtt cagaggtttt tattttggtc tttgaaaaat      1920
ttgtggctca acctctctac atatgcacaa acaggaaaca ggaaatccaa tcttgtaaat      1980
tgctgggcac atgaaatggc ctgtgttgta ctttgccaca tgactaaccc tattatgggc      2040
aaagttgcta agaatttgag gttttcaatt ggctgggaag aatttggtga gcgcagtgaa      2100
ataaatggaa gtccagacca gaataagtgt ccacagtttc cattttttaa ttctggcccc      2160
cagatttcag tagatccaat ttacatattc ccaactatga catttctgca cctgtggcag      2220
tcttaccaac caaaatttga gtgtactgtg acatcctgtc tgataaaagg agattttttg      2280
gatggcagaa gtataatttc acaactaatc cttttacttt tgtaatagga gacaaaccaa      2340
aactgtattt tatgtcttaa aagtgctttt atatatttt ttcttgtttc caaaccattt      2400
cttccttaaa catgaattaa tgtgaatctt caaagtaatt agtgttttct gtttcttaag      2460
taggtatgag gtatttgtta tttatttcct acacatatga aatagattga aattgttctt      2520
atgcaaaata atttgtaatc ttttaagtgg gtaagtggaa gttgagagta tctacagaac      2580
cattaaaatg ttcaccattc ttaagtcttg caaggagct aagaaacact gccatttat      2640 gtgttctcca aataatcaaa tgggcccagt tgctaagaat acaacataaa tttcaaagtc      2700
tccctaatat tttattcttt aaacaggcac agaaagcctt ccaaacatct ttatttggca      2760
ggcagtgtaa acttgctttt tatggaagct ttgtgtctgt tagagatgag aagaaagggt      2820
gaggtttgtg attaagtttg gatggacttg accatatgag taagcctgaa ggcagagtag      2880 gttttttaa ttcaaggata attatttttcc ttggcaggga tttgaaacat tatttggcaa      2940
ctgaaatatc agaaatacag gcccataaga aagacatctt tggctataaa tttgttttac      3000 aggtaaaatac tatataaagg aaactttgat aatttgttta aattagaaac actaaatttt      3060
ttaagctaag tcgatactag gtccacctca ggaaataact ttcctggagt gagaaggact      3120
cactgacttg atcactatat agagtatttt tatttctgat gaagcatttt tttcttcatt      3180 ttttttttcca gttttccatc attctgggag gattttaagt gtttaacaag gttttttgtca      3240 tgtttagaaa tacggaaagc agacttaagc atagaaaagc tttatttct tacattctga      3300 tagagaacta tgaaactccc acacctttgc ttttttgtgtt ttcttacatg atacacttcag      3360 gctactcttg ttagttttgac catgcacagg gaaataagcc tagaatttgc ttttctctat      3420
ttttattatc caaataaagc cagtagtact ctcagaaaat tctcatctct caggtgtcct      3480
ccctctcgtg gtaacatcag aacagagata gatacttatc tacctatgcc agtgaacaca      3540
gttgtgttgt tcaattttta aggtattttt agatgataaa tattgatgta agtggagaca      3600
gttgacctga acagcaagtt tgttggagtc taatcccatc tccagtctgc ttcttggagg      3660
aaccagacta acatgactct gccctatata atacaaataa ttattttcca tatatctgat      3720
ttttagcttt gcatttactt taaatcatgc ttcaattaaa gacacacctt ctttaatcat      3780
tttattagta tttctaagta tgatggaaag gttcagagct caggggagga tatggagatc      3840
cagggaggct tcctgtagga agtggcctgt gtagtgcttc aagggccagg ctgccaggcc      3900
atgttgcagc tgaccaccca cctgcagtgt accgccggaa gcaccaggag ctgcaagcca      3960
tgcagatgga gctgcagag                                                  3979
```

<210> SEQ ID NO 5
<211> LENGTH: 853
<212> TYPE: DNA
<213> ORGANISM: Homo sapiens -continued

```
<400> SEQUENCE: 5
aatgtctaac tcgggagact atgaaatatt gtactgtaag tatgaatgat tttatatata      60
tatatatatg ctatgattat atttatatat atatatatat atgctaagat gtgtctgtca     120
ggggcgctaa tgaacaggct gcatggaatc tgaattgtgc agagaatgct tgccaacctc     180
tttaacctga caaagcatat gttatgctga gctaaggtaa tgagaatctc aaatgtgatt     240
cacttctcca agagtaatga attaatgtta atagtgtaga acagaaggca catatagtaa     300
taaaaaatta ctctgtcaaa ttgatgctgc tctgaatggt ttttcattta attacttctc     360
ctggaggcag ggaggaatat gatagatggg catttatgct ttttagagga aaaaaaaaac     420
ttccatggga atcagtttgt agttttataa accctgttaa agtgaacact ttcttttcct     480
ttttaaatgt gtcttaatgt ttttcagtgt atggattata aatacaagta aacgtggcta     540
gtttgaatca agatgcactt tcaaatacat ttgtacacaa aataattatt ttccatatat     600
ctgattttta gctttgcatt tactttaaat catgcttcaa ttaaagacac accttcttta     660
atcattttat tagtatttct aagtatgatg gaaaggttca gagctcaggg gaggatatgg     720
agatccaggg aggcttcctg taggaagtgg cctgtgtagt gcttcaaggg ccaggctgcc     780
aggccatgtt gcagctgacc acccacctgc agtgtaccgc cggaagcacc aggagctgca     840
agccatgcag atg                                                        853

<210> SEQ ID NO 6
<211> LENGTH: 3933
<212> TYPE: DNA
<213> ORGANISM: Homo sapiens
<220> FEATURE:
<221> NAME/KEY: CDS
<222> LOCATION: (1)..(3930)

<400> SEQUENCE: 6 atg gac ggt ttc gcc ggc agt ctc gat gat agt att tct gct gca agt      48
Met Asp Gly Phe Ala Gly Ser Leu Asp Asp Ser Ile Ser Ala Ala Ser
1               5                   10                  15 act tct gat gtt caa gat cgc ctg tca gct ctt gag tca cga gtt cag      96
Thr Ser Asp Val Gln Asp Arg Leu Ser Ala Leu Glu Ser Arg Val Gln
            20                  25                  30 caa caa gaa gat gaa atc act gtg cta aag gcg gct ttg gct gat gtt     144
Gln Gln Glu Asp Glu Ile Thr Val Leu Lys Ala Ala Leu Ala Asp Val
        35                  40                  45 ttg agg cgt ctt gca atc tct gaa gat cat gtg gcc tca gtg aaa aaa     192
Leu Arg Arg Leu Ala Ile Ser Glu Asp His Val Ala Ser Val Lys Lys
    50                  55                  60 tca gtc tca agt aaa ggc caa cca agc cct cga gca gtt att ccc atg     240
Ser Val Ser Ser Lys Gly Gln Pro Ser Pro Arg Ala Val Ile Pro Met
65                  70                  75                  80 tcc tgt ata acc aat gga agt ggt gca aac aga aaa cca agt cat acc     288
Ser Cys Ile Thr Asn Gly Ser Gly Ala Asn Arg Lys Pro Ser His Thr
                85                  90                  95 agt gct gtc tca att gca gga aaa gaa act ctt tca tct gct gct aaa     336
Ser Ala Val Ser Ile Ala Gly Lys Glu Thr Leu Ser Ser Ala Ala Lys
            100                 105                 110 agt ggt aca gaa aaa aag aaa gaa aaa cca caa gga cag aga gaa aaa     384
Ser Gly Thr Glu Lys Lys Lys Glu Lys Pro Gln Gly Gln Arg Glu Lys
        115                 120                 125 aaa gag gaa tct cat tct aat gat caa agt cca caa att cga gca tca     432
Lys Glu Glu Ser His Ser Asn Asp Gln Ser Pro Gln Ile Arg Ala Ser
    130                 135                 140
```

-continued

| | | |
|---|---|---|
| cct tct ccc cag ccc tct tca caa cct ctc caa ata cac aga caa act<br>Pro Ser Pro Gln Pro Ser Ser Gln Pro Leu Gln Ile His Arg Gln Thr<br>145                    150                        155                    160 | 480 | |
| cca gaa agc aag aat gct act ccc acc aaa agc ata aaa cga cca tca<br>Pro Glu Ser Lys Asn Ala Thr Pro Thr Lys Ser Ile Lys Arg Pro Ser<br>                165                        170                        175 | 528 | |
| cca gct gaa aag tca cat aat tct tgg gaa aat tca gat gat agc cgt<br>Pro Ala Glu Lys Ser His Asn Ser Trp Glu Asn Ser Asp Asp Ser Arg<br>        180                        185                        190 | 576 | |
| aat aaa ttg tcg aaa ata cct tca aca ccc aaa tta ata cca aaa gtt<br>Asn Lys Leu Ser Lys Ile Pro Ser Thr Pro Lys Leu Ile Pro Lys Val<br>                195                        200                        205 | 624 | |
| acc aaa act gca gac aag cat aaa gat gtc atc atc aac caa gaa gga<br>Thr Lys Thr Ala Asp Lys His Lys Asp Val Ile Ile Asn Gln Glu Gly<br>210                    215                        220 | 672 | |
| gaa tat att aaa atg ttt atg cgc ggt cgg cca att acc atg ttc att<br>Glu Tyr Ile Lys Met Phe Met Arg Gly Arg Pro Ile Thr Met Phe Ile<br>225                    230                        235                  240 | 720 | |
| cct tcc gat gtt gac aac tat gat gac atc aga acg gaa ctg cct cct<br>Pro Ser Asp Val Asp Asn Tyr Asp Asp Ile Arg Thr Glu Leu Pro Pro<br>                                  245                        250                        255 | 768 | |
| gag aag ctc aaa ctg gag tgg gca tat ggt tat cga gga aag gac tgt<br>Glu Lys Leu Lys Leu Glu Trp Ala Tyr Gly Tyr Arg Gly Lys Asp Cys<br>                260                        265                        270 | 816 | |
| aga gct aat gtt tac ctt ctt ccg acc ggg gaa ata gtt tat ttc att<br>Arg Ala Asn Val Tyr Leu Leu Pro Thr Gly Glu Ile Val Tyr Phe Ile<br>        275                        280                        285 | 864 | |
| gca tca gta gta gta cta ttt aat tat gag gag aga act cag cga cac<br>Ala Ser Val Val Val Leu Phe Asn Tyr Glu Glu Arg Thr Gln Arg His<br>                290                        295                        300 | 912 | |
| tac ctg ggc cat aca gac tgt gtg aaa tgc ctt gct ata cat cct gac<br>Tyr Leu Gly His Thr Asp Cys Val Lys Cys Leu Ala Ile His Pro Asp<br>305                    310                        315                  320 | 960 | |
| aaa att agg att gca act gga cag ata gct ggc gtg gat aaa gat gga<br>Lys Ile Arg Ile Ala Thr Gly Gln Ile Ala Gly Val Asp Lys Asp Gly<br>                              325                        330                        335 | 1008 | |
| agg cct cta caa ccc cac gtc aga gtg tgg gat tct gtt act cta tcc<br>Arg Pro Leu Gln Pro His Val Arg Val Trp Asp Ser Val Thr Leu Ser<br>                    340                        345                        350 | 1056 | |
| aca ctg cag att att gga ctt ggc act ttt gag cgt gga gta gga tgc<br>Thr Leu Gln Ile Ile Gly Leu Gly Thr Phe Glu Arg Gly Val Gly Cys<br>                355                        360                        365 | 1104 | |
| ctg gat ttt tca aaa gca gat tca ggt gtt cat tta tgt gtt att gat<br>Leu Asp Phe Ser Lys Ala Asp Ser Gly Val His Leu Cys Val Ile Asp<br>        370                        375                        380 | 1152 | |
| gac tcc aat gag cat atg ctt act gta tgg gac tgg cag aag aaa gca<br>Asp Ser Asn Glu His Met Leu Thr Val Trp Asp Trp Gln Lys Lys Ala<br>385                    390                        395                  400 | 1200 | |
| aaa gga gca gaa ata aag aca aca aat gaa gtt gtt ttg gct gtg gag<br>Lys Gly Ala Glu Ile Lys Thr Thr Asn Glu Val Val Leu Ala Val Glu<br>                                  405                        410                        415 | 1248 | |
| ttt cac cca aca gat gca aat acc ata att aca tgc ggt aaa tct cat<br>Phe His Pro Thr Asp Ala Asn Thr Ile Ile Thr Cys Gly Lys Ser His<br>                    420                        425                        430 | 1296 | |
| att ttc ttc tgg acc tgg agc ggc aat tca cta aca aga aaa cag gga<br>Ile Phe Phe Trp Thr Trp Ser Gly Asn Ser Leu Thr Arg Lys Gln Gly<br>                435                        440                        445 | 1344 | |
| att ttt ggg aaa tat gaa aag cca aaa ttt gtg cag tgt tta gca ttc<br>Ile Phe Gly Lys Tyr Glu Lys Pro Lys Phe Val Gln Cys Leu Ala Phe | 1392 | |

-continued

```
                   450                 455                 460
ttg ggg aat gga gat gtt ctt act gga gac tca ggt gga gtc atg ctt      1440
Leu Gly Asn Gly Asp Val Leu Thr Gly Asp Ser Gly Gly Val Met Leu
465                 470                 475                 480 ata tgg agc aaa act act gta gag ccc aca cct ggg aaa gga cct aaa      1488
Ile Trp Ser Lys Thr Thr Val Glu Pro Thr Pro Gly Lys Gly Pro Lys
                485                 490                 495 ggt gta tat caa atc agc aaa caa atc aaa gct cat gat ggc agt gtg      1536
Gly Val Tyr Gln Ile Ser Lys Gln Ile Lys Ala His Asp Gly Ser Val
            500                 505                 510 ttc aca ctt tgt cag atg aga aat ggg atg tta tta act gga gga ggg      1584
Phe Thr Leu Cys Gln Met Arg Asn Gly Met Leu Leu Thr Gly Gly Gly
        515                 520                 525 aaa gac aga aaa ata att ctg tgg gat cat gat ctg aat cct gaa aga      1632
Lys Asp Arg Lys Ile Ile Leu Trp Asp His Asp Leu Asn Pro Glu Arg
530                 535                 540 gaa ata gag gtt cct gat cag tat ggc aca atc aga gct gta gca gaa      1680
Glu Ile Glu Val Pro Asp Gln Tyr Gly Thr Ile Arg Ala Val Ala Glu
545                 550                 555                 560 gga aag gca gat caa ttt tta gta ggc aca tca cga aac ttt att tta      1728
Gly Lys Ala Asp Gln Phe Leu Val Gly Thr Ser Arg Asn Phe Ile Leu
                565                 570                 575 cga gga aca ttt aat gat ggc ttc caa ata gaa gta cag ggt cat aca      1776
Arg Gly Thr Phe Asn Asp Gly Phe Gln Ile Glu Val Gln Gly His Thr
            580                 585                 590 gat gag ctt tgg ggt ctt gcc aca cat ccc ttc aaa gat ttg ctc ttg      1824
Asp Glu Leu Trp Gly Leu Ala Thr His Pro Phe Lys Asp Leu Leu Leu
        595                 600                 605 aca tgt gct cag gac agg cag gtg tgc ctg tgg aac tca atg gaa cac      1872
Thr Cys Ala Gln Asp Arg Gln Val Cys Leu Trp Asn Ser Met Glu His
610                 615                 620 agg ctg gaa tgg acc agg ctg gta gat gaa cca gga cac tgt gca gat      1920
Arg Leu Glu Trp Thr Arg Leu Val Asp Glu Pro Gly His Cys Ala Asp
625                 630                 635                 640 ttt cat cca agt ggc aca gtg gtg gcc ata gga acg cac tca ggc agg      1968
Phe His Pro Ser Gly Thr Val Val Ala Ile Gly Thr His Ser Gly Arg
                645                 650                 655 tgg ttt gtt ctg gat gca gaa acc aga gat cta gtt tct atc cac aca      2016
Trp Phe Val Leu Asp Ala Glu Thr Arg Asp Leu Val Ser Ile His Thr
            660                 665                 670 gac ggg aat gaa cag ctc tct gtg atg cgc tac tca ata gat ggt acc      2064
Asp Gly Asn Glu Gln Leu Ser Val Met Arg Tyr Ser Ile Asp Gly Thr
        675                 680                 685 ttc ctg gct gta gga tct cat gac aac ttt att tac ctc tat gta gtc      2112
Phe Leu Ala Val Gly Ser His Asp Asn Phe Ile Tyr Leu Tyr Val Val
690                 695                 700 tct gaa aat gga aga aaa tat agc aga tat gga agg tgc act gga cat      2160
Ser Glu Asn Gly Arg Lys Tyr Ser Arg Tyr Gly Arg Cys Thr Gly His
705                 710                 715                 720 tcc agc tac atc aca cac ctt gac tgg tcc cca gac aac aag tat ata      2208
Ser Ser Tyr Ile Thr His Leu Asp Trp Ser Pro Asp Asn Lys Tyr Ile
                725                 730                 735 atg tct aac tcg gga gac tat gaa ata ttg tac ttg tac cgc cgg aag      2256
Met Ser Asn Ser Gly Asp Tyr Glu Ile Leu Tyr Leu Tyr Arg Arg Lys
            740                 745                 750 cac cag gag ctg caa gcc atg cag atg gag ctg cag agc cct gag tac      2304
His Gln Glu Leu Gln Ala Met Gln Met Glu Leu Gln Ser Pro Glu Tyr
        755                 760                 765 aag ctg agc aag ctc cgc acc tcg acc atc atg acc gac tac aac ccc      2352
```

```
             Lys Leu Ser Lys Leu Arg Thr Ser Thr Ile Met Thr Asp Tyr Asn Pro
                 770             775             780 aac tac tgc ttt gct ggc aag acc tcc tcc atc agt gac ctg aag gag        2400
Asn Tyr Cys Phe Ala Gly Lys Thr Ser Ser Ile Ser Asp Leu Lys Glu
785             790                 795             800 gtg ccg cgg aaa aac atc acc ctc att cgg ggt ctg ggc cat gga gcc        2448
Val Pro Arg Lys Asn Ile Thr Leu Ile Arg Gly Leu Gly His Gly Ala
                805             810             815 ttt ggg gag gtg tat gaa ggc cag gtg tcc gga atg ccc aac gac cca        2496
Phe Gly Glu Val Tyr Glu Gly Gln Val Ser Gly Met Pro Asn Asp Pro
            820             825             830 agc ccc ctg caa gtg gct gtg aag acg ctg cct gaa gtg tgc tct gaa        2544
Ser Pro Leu Gln Val Ala Val Lys Thr Leu Pro Glu Val Cys Ser Glu
        835             840             845 cag gac gaa ctg gat ttc ctc atg gaa gcc ctg atc atc agc aaa ttc        2592
Gln Asp Glu Leu Asp Phe Leu Met Glu Ala Leu Ile Ile Ser Lys Phe
850             855             860 aac cac cag aac att gtt cgc tgc att ggg gtg agc ctg caa tcc ctg        2640
Asn His Gln Asn Ile Val Arg Cys Ile Gly Val Ser Leu Gln Ser Leu
865             870             875             880 ccc cgg ttc atc ctg ctg gag ctc atg gcg ggg gga gac ctc aag tcc        2688
Pro Arg Phe Ile Leu Leu Glu Leu Met Ala Gly Gly Asp Leu Lys Ser
                885             890             895 ttc ctc cga gag acc cgc cct cgc ccg agc cag ccc tcc tcc ctg gcc        2736
Phe Leu Arg Glu Thr Arg Pro Arg Pro Ser Gln Pro Ser Ser Leu Ala
            900             905             910 atg ctg gac ctt ctg cac gtg gct cgg gac att gcc tgt ggc tgt cag        2784
Met Leu Asp Leu Leu His Val Ala Arg Asp Ile Ala Cys Gly Cys Gln
        915             920             925 tat ttg gag gaa aac cac ttc atc cac cga gac att gct gcc aga aac        2832
Tyr Leu Glu Glu Asn His Phe Ile His Arg Asp Ile Ala Ala Arg Asn
930             935             940 tgc ctc ttg acc tgt cca ggc cct gga aga gtg gcc aag att gga gac        2880
Cys Leu Leu Thr Cys Pro Gly Pro Gly Arg Val Ala Lys Ile Gly Asp
945             950             955             960 ttc ggg atg gcc cga gac atc tac agg gcg agc tac tat aga aag gga        2928
Phe Gly Met Ala Arg Asp Ile Tyr Arg Ala Ser Tyr Tyr Arg Lys Gly
                965             970             975 ggc tgt gcc atg ctg cca gtt aag tgg atg ccc cca gag gcc ttc atg        2976
Gly Cys Ala Met Leu Pro Val Lys Trp Met Pro Pro Glu Ala Phe Met
            980             985             990 gaa gga ata ttc act tct aaa aca gac aca tgg tcc ttt gga gtg ctg        3024
Glu Gly Ile Phe Thr Ser Lys Thr Asp Thr Trp Ser Phe Gly Val Leu
        995             1000            1005 cta tgg gaa atc ttt tct ctt gga tat atg cca tac ccc agc aaa            3069
Leu Trp Glu Ile Phe Ser Leu Gly Tyr Met Pro Tyr Pro Ser Lys
    1010            1015            1020 agc aac cag gaa gtt ctg gag ttt gtc acc agt gga ggc cgg atg            3114
Ser Asn Gln Glu Val Leu Glu Phe Val Thr Ser Gly Gly Arg Met
    1025            1030            1035 gac cca ccc aag aac tgc cct ggg cct gta tac cgg ata atg act            3159
Asp Pro Pro Lys Asn Cys Pro Gly Pro Val Tyr Arg Ile Met Thr
    1040            1045            1050 cag tgc tgg caa cat cag cct gaa gac agg ccc aac ttt gcc atc            3204
Gln Cys Trp Gln His Gln Pro Glu Asp Arg Pro Asn Phe Ala Ile
    1055            1060            1065 att ttg gag agg att gaa tac tgc acc cag gac ccg gat gta atc            3249
Ile Leu Glu Arg Ile Glu Tyr Cys Thr Gln Asp Pro Asp Val Ile
    1070            1075            1080
```

| | | | | | | | | | | |
|---|---|---|---|---|---|---|---|---|---|---|
| aac | acc | gct | ttg | ccg | ata | gaa | tat | ggt | cca | ctt | gtg | gaa | gag | gaa | 3294 |
| Asn | Thr | Ala | Leu | Pro | Ile | Glu | Tyr | Gly | Pro | Leu | Val | Glu | Glu | Glu | |
| 1085 | | | | 1090 | | | | | 1095 | | | | | | |

```
aac acc gct ttg ccg ata gaa tat ggt cca ctt gtg gaa gag gaa      3294
Asn Thr Ala Leu Pro Ile Glu Tyr Gly Pro Leu Val Glu Glu Glu
    1085            1090                1095 gag aaa gtg cct gtg agg ccc aag gac cct gag ggg gtt cct cct      3339
Glu Lys Val Pro Val Arg Pro Lys Asp Pro Glu Gly Val Pro Pro
1100            1105                1110 ctc ctg gtc tct caa cag gca aaa cgg gag gag gag cgc agc cca      3384
Leu Leu Val Ser Gln Gln Ala Lys Arg Glu Glu Glu Arg Ser Pro
    1115            1120                1125 gct gcc cca cca cct ctg cct acc acc tcc tct ggc aag gct gca      3429
Ala Ala Pro Pro Pro Leu Pro Thr Thr Ser Ser Gly Lys Ala Ala
1130            1135                1140 aag aaa ccc aca gct gca gag gtc tct gtt cga gtc cct aga ggg      3474
Lys Lys Pro Thr Ala Ala Glu Val Ser Val Arg Val Pro Arg Gly
    1145            1150                1155 ccg gcc gtg gaa ggg gga cac gtg aat atg gca ttc tct cag tcc      3519
Pro Ala Val Glu Gly Gly His Val Asn Met Ala Phe Ser Gln Ser
1160            1165                1170 aac cct cct tcg gag ttg cac agg gtc cac gga tcc aga aac aag      3564
Asn Pro Pro Ser Glu Leu His Arg Val His Gly Ser Arg Asn Lys
    1175            1180                1185 ccc acc agc ttg tgg aac cca acg tac ggc tcc tgg ttt aca gag      3609
Pro Thr Ser Leu Trp Asn Pro Thr Tyr Gly Ser Trp Phe Thr Glu
1190            1195                1200 aaa ccc acc aaa aag aat aat cct ata gca aag aag gag cca cac      3654
Lys Pro Thr Lys Lys Asn Asn Pro Ile Ala Lys Lys Glu Pro His
    1205            1210                1215 gag agg ggt aac ctg ggg ctg gag gga agc tgt act gtc cca cct      3699
Glu Arg Gly Asn Leu Gly Leu Glu Gly Ser Cys Thr Val Pro Pro
1220            1225                1230 aac gtt gca act ggg aga ctt ccg ggg gcc tca ctg ctc cta gag      3744
Asn Val Ala Thr Gly Arg Leu Pro Gly Ala Ser Leu Leu Leu Glu
    1235            1240                1245 ccc tct tcg ctg act gcc aat atg aag gag gta cct ctg ttc agg      3789
Pro Ser Ser Leu Thr Ala Asn Met Lys Glu Val Pro Leu Phe Arg
1250            1255                1260 cta cgt cac ttc cct tgt ggg aat gtc aat tac ggc tac cag caa      3834
Leu Arg His Phe Pro Cys Gly Asn Val Asn Tyr Gly Tyr Gln Gln
    1265            1270                1275 cag ggc ttg ccc tta gaa gcc gct act gcc cct gga gct ggt cat      3879
Gln Gly Leu Pro Leu Glu Ala Ala Thr Ala Pro Gly Ala Gly His
1280            1285                1290 tac gag gat acc att ctg aaa agc aag aat agc atg aac cag cct      3924
Tyr Glu Asp Thr Ile Leu Lys Ser Lys Asn Ser Met Asn Gln Pro
    1295            1300                1305 ggg ccc tga                                                      3933
Gly Pro
    1310

<210> SEQ ID NO 7
<211> LENGTH: 1310
<212> TYPE: PRT
<213> ORGANISM: Homo sapiens

<400> SEQUENCE: 7

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
```

```
                35                  40                  45
Leu Arg Arg Leu Ala Ile Ser Glu Asp His Val Ala Ser Val Lys Lys
 50                  55                  60

Ser Val Ser Ser Lys Gly Gln Pro Ser Pro Arg Ala Val Ile Pro Met
 65                  70                  75                  80

Ser Cys Ile Thr Asn Gly Ser Gly Ala Asn Arg Lys Pro Ser His Thr
                 85                  90                  95

Ser Ala Val Ser Ile Ala Gly Lys Glu Thr Leu Ser Ser Ala Ala Lys
                100                 105                 110

Ser Gly Thr Glu Lys Lys Lys Glu Lys Pro Gln Gly Gln Arg Glu Lys
                115                 120                 125

Lys Glu Glu Ser His Ser Asn Asp Gln Ser Pro Gln Ile Arg Ala Ser
130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
                180                 185                 190

Asn Lys Leu Ser Lys Ile Pro Ser Thr Pro Lys Leu Ile Pro Lys Val
                195                 200                 205

Thr Lys Thr Ala Asp Lys His Lys Asp Val Ile Ile Asn Gln Glu Gly
210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
                260                 265                 270

Arg Ala Asn Val Tyr Leu Leu Pro Thr Gly Glu Ile Val Tyr Phe Ile
                275                 280                 285

Ala Ser Val Val Leu Phe Asn Tyr Glu Glu Arg Thr Gln Arg His
290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
                340                 345                 350

Thr Leu Gln Ile Ile Gly Leu Gly Thr Phe Glu Arg Gly Val Gly Cys
                355                 360                 365

Leu Asp Phe Ser Lys Ala Asp Ser Gly Val His Leu Cys Val Ile Asp
                370                 375                 380

Asp Ser Asn Glu His Met Leu Thr Val Trp Asp Trp Gln Lys Lys Ala
385                 390                 395                 400

Lys Gly Ala Glu Ile Lys Thr Thr Asn Glu Val Val Leu Ala Val Glu
                405                 410                 415

Phe His Pro Thr Asp Ala Asn Thr Ile Ile Thr Cys Gly Lys Ser His
                420                 425                 430

Ile Phe Phe Trp Thr Trp Ser Gly Asn Ser Leu Thr Arg Lys Gln Gly
                435                 440                 445

Ile Phe Gly Lys Tyr Glu Lys Pro Lys Phe Val Gln Cys Leu Ala Phe
                450                 455                 460
```

```
Leu Gly Asn Gly Asp Val Leu Thr Gly Asp Ser Gly Val Met Leu
465                 470                 475                 480

Ile Trp Ser Lys Thr Thr Val Glu Pro Thr Pro Gly Lys Gly Pro Lys
                485                 490                 495

Gly Val Tyr Gln Ile Ser Lys Gln Ile Lys Ala His Asp Gly Ser Val
            500                 505                 510

Phe Thr Leu Cys Gln Met Arg Asn Gly Met Leu Leu Thr Gly Gly
        515                 520                 525

Lys Asp Arg Lys Ile Ile Leu Trp Asp His Asp Leu Asn Pro Glu Arg
530                 535                 540

Glu Ile Glu Val Pro Asp Gln Tyr Gly Thr Ile Arg Ala Val Ala Glu
545                 550                 555                 560

Gly Lys Ala Asp Gln Phe Leu Val Gly Thr Ser Arg Asn Phe Ile Leu
                565                 570                 575

Arg Gly Thr Phe Asn Asp Gly Phe Gln Ile Glu Val Gln Gly His Thr
            580                 585                 590

Asp Glu Leu Trp Gly Leu Ala Thr His Pro Phe Lys Asp Leu Leu Leu
        595                 600                 605

Thr Cys Ala Gln Asp Arg Gln Val Cys Leu Trp Asn Ser Met Glu His
610                 615                 620

Arg Leu Glu Trp Thr Arg Leu Val Asp Glu Pro Gly His Cys Ala Asp
625                 630                 635                 640

Phe His Pro Ser Gly Thr Val Val Ala Ile Gly Thr His Ser Gly Arg
                645                 650                 655

Trp Phe Val Leu Asp Ala Glu Thr Arg Asp Leu Val Ser Ile His Thr
            660                 665                 670

Asp Gly Asn Glu Gln Leu Ser Val Met Arg Tyr Ser Ile Asp Gly Thr
        675                 680                 685

Phe Leu Ala Val Gly Ser His Asp Asn Phe Ile Tyr Leu Tyr Val Val
        690                 695                 700

Ser Glu Asn Gly Arg Lys Tyr Ser Arg Tyr Gly Arg Cys Thr Gly His
705                 710                 715                 720

Ser Ser Tyr Ile Thr His Leu Asp Trp Ser Pro Asp Asn Lys Tyr Ile
            725                 730                 735

Met Ser Asn Ser Gly Asp Tyr Glu Ile Leu Tyr Leu Tyr Arg Arg Lys
            740                 745                 750

His Gln Glu Leu Gln Ala Met Gln Met Glu Leu Gln Ser Pro Glu Tyr
        755                 760                 765

Lys Leu Ser Lys Leu Arg Thr Ser Thr Ile Met Thr Asp Tyr Asn Pro
770                 775                 780

Asn Tyr Cys Phe Ala Gly Lys Thr Ser Ser Ile Ser Asp Leu Lys Glu
785                 790                 795                 800

Val Pro Arg Lys Asn Ile Thr Leu Ile Arg Gly Leu Gly His Gly Ala
                805                 810                 815

Phe Gly Glu Val Tyr Glu Gly Gln Val Ser Gly Met Pro Asn Asp Pro
            820                 825                 830

Ser Pro Leu Gln Val Ala Val Lys Thr Leu Pro Glu Val Cys Ser Glu
        835                 840                 845

Gln Asp Glu Leu Asp Phe Leu Met Glu Ala Leu Ile Ile Ser Lys Phe
        850                 855                 860

Asn His Gln Asn Ile Val Arg Cys Ile Gly Val Ser Leu Gln Ser Leu
865                 870                 875                 880
```

-continued

Pro Arg Phe Ile Leu Leu Glu Leu Met Ala Gly Gly Asp Leu Lys Ser
                885                 890                 895

Phe Leu Arg Glu Thr Arg Pro Arg Pro Ser Gln Pro Ser Ser Leu Ala
            900                 905                 910

Met Leu Asp Leu Leu His Val Ala Arg Asp Ile Ala Cys Gly Cys Gln
            915                 920                 925

Tyr Leu Glu Glu Asn His Phe Ile His Arg Asp Ile Ala Ala Arg Asn
        930                 935                 940

Cys Leu Leu Thr Cys Pro Gly Pro Gly Arg Val Ala Lys Ile Gly Asp
945                 950                 955                 960

Phe Gly Met Ala Arg Asp Ile Tyr Arg Ala Ser Tyr Tyr Arg Lys Gly
            965                 970                 975

Gly Cys Ala Met Leu Pro Val Lys Trp Met Pro Pro Glu Ala Phe Met
            980                 985                 990

Glu Gly Ile Phe Thr Ser Lys Thr Asp Thr Trp Ser Phe Gly Val Leu
            995                 1000                1005

Leu Trp Glu Ile Phe Ser Leu Gly Tyr Met Pro Tyr Pro Ser Lys
    1010                1015                1020

Ser Asn Gln Glu Val Leu Glu Phe Val Thr Ser Gly Gly Arg Met
    1025                1030                1035

Asp Pro Pro Lys Asn Cys Pro Gly Pro Val Tyr Arg Ile Met Thr
    1040                1045                1050

Gln Cys Trp Gln His Gln Pro Glu Asp Arg Pro Asn Phe Ala Ile
    1055                1060                1065

Ile Leu Glu Arg Ile Glu Tyr Cys Thr Gln Asp Pro Asp Val Ile
    1070                1075                1080

Asn Thr Ala Leu Pro Ile Glu Tyr Gly Pro Leu Val Glu Glu Glu
    1085                1090                1095

Glu Lys Val Pro Val Arg Pro Lys Asp Pro Glu Gly Val Pro Pro
    1100                1105                1110

Leu Leu Val Ser Gln Gln Ala Lys Arg Glu Glu Glu Arg Ser Pro
    1115                1120                1125

Ala Ala Pro Pro Pro Leu Pro Thr Thr Ser Ser Gly Lys Ala Ala
    1130                1135                1140

Lys Lys Pro Thr Ala Ala Glu Val Ser Val Arg Val Pro Arg Gly
    1145                1150                1155

Pro Ala Val Glu Gly Gly His Val Asn Met Ala Phe Ser Gln Ser
    1160                1165                1170

Asn Pro Pro Ser Glu Leu His Arg Val His Gly Ser Arg Asn Lys
    1175                1180                1185

Pro Thr Ser Leu Trp Asn Pro Thr Tyr Gly Ser Trp Phe Thr Glu
    1190                1195                1200

Lys Pro Thr Lys Lys Asn Asn Pro Ile Ala Lys Lys Glu Pro His
    1205                1210                1215

Glu Arg Gly Asn Leu Gly Leu Glu Gly Ser Cys Thr Val Pro Pro
    1220                1225                1230

Asn Val Ala Thr Gly Arg Leu Pro Gly Ala Ser Leu Leu Leu Glu
    1235                1240                1245

Pro Ser Ser Leu Thr Ala Asn Met Lys Glu Val Pro Leu Phe Arg
    1250                1255                1260

Leu Arg His Phe Pro Cys Gly Asn Val Asn Tyr Gly Tyr Gln Gln
    1265                1270                1275

Gln Gly Leu Pro Leu Glu Ala Ala Thr Ala Pro Gly Ala Gly His

```
                    1280            1285             1290
Tyr Glu  Asp Thr Ile Leu Lys  Ser Lys Asn Ser Met  Asn Gln Pro
    1295             1300              1305

Gly Pro
    1310
```

<210> SEQ ID NO 8
<211> LENGTH: 24
<212> TYPE: DNA
<213> ORGANISM: Homo sapiens

<400> SEQUENCE: 8
gtgcagtgtt tagcattctt gggg                                          24

<210> SEQ ID NO 9
<211> LENGTH: 24
<212> TYPE: DNA
<213> ORGANISM: Homo sapiens

<400> SEQUENCE: 9
tcttgccagc aaagcagtag ttgg                                          24

<210> SEQ ID NO 10
<211> LENGTH: 20
<212> TYPE: DNA
<213> ORGANISM: Homo sapiens

<400> SEQUENCE: 10
gtcagtggtg gacctgacct                                               20

<210> SEQ ID NO 11
<211> LENGTH: 20
<212> TYPE: DNA
<213> ORGANISM: Homo sapiens

<400> SEQUENCE: 11
tgagcttgac aaagtggtcg                                               20

<210> SEQ ID NO 12
<211> LENGTH: 18
<212> TYPE: DNA
<213> ORGANISM: Homo sapiens

<400> SEQUENCE: 12
gggaaggtga aggtcgga                                                 18

<210> SEQ ID NO 13
<211> LENGTH: 17
<212> TYPE: DNA
<213> ORGANISM: Homo sapiens

<400> SEQUENCE: 13
gcagccctgg tgaccag                                                  17

<210> SEQ ID NO 14
<211> LENGTH: 247
<212> TYPE: DNA
<213> ORGANISM: Homo sapiens

<400> SEQUENCE: 14
gtgcagtgtt tagcattctt ggggaatgga gatgttctta ctggagactc aggtggagtc   60
atgcttatat ggagcaaaac tactgtagag cccacacctg gaaaggacc taaagtgtac   120 cgccggaagc accaggagct gcaagccatg cagatggagc tgcagagccc tgagtacaag    180
ctgagcaagc tccgcacctc gaccatcatg accgactaca accccaacta ctgctttgct    240
ggcaaga    247

<210> SEQ ID NO 15
<211> LENGTH: 16
<212> TYPE: DNA
<213> ORGANISM: Homo sapiens

<400> SEQUENCE: 15
gcacagggaa ataagc    16

<210> SEQ ID NO 16
<211> LENGTH: 16
<212> TYPE: DNA
<213> ORGANISM: Homo sapiens

<400> SEQUENCE: 16
gggcagagtc atgtta    16

<210> SEQ ID NO 17
<211> LENGTH: 16
<212> TYPE: DNA
<213> ORGANISM: Homo sapiens

<400> SEQUENCE: 17
ccagtagtac tctcag    16

<210> SEQ ID NO 18
<211> LENGTH: 16
<212> TYPE: DNA
<213> ORGANISM: Homo sapiens

<400> SEQUENCE: 18
cccctgagct ctgaac    16

<210> SEQ ID NO 19
<211> LENGTH: 17
<212> TYPE: DNA
<213> ORGANISM: Homo sapiens

<400> SEQUENCE: 19
ccagtgaaca cagttgt    17

<210> SEQ ID NO 20
<211> LENGTH: 17
<212> TYPE: DNA
<213> ORGANISM: Homo sapiens

<400> SEQUENCE: 20
cctggatctc catatcc    17

<210> SEQ ID NO 21
<211> LENGTH: 17
<212> TYPE: DNA
<213> ORGANISM: Homo sapiens

<400> SEQUENCE: 21
gatgtaagtg gagacag    17

<210> SEQ ID NO 22

```
<211> LENGTH: 17
<212> TYPE: DNA
<213> ORGANISM: Homo sapiens

<400> SEQUENCE: 22
ttcctacagg aagcctc                                                        17

<210> SEQ ID NO 23
<211> LENGTH: 18
<212> TYPE: DNA
<213> ORGANISM: Homo sapiens

<400> SEQUENCE: 23
gatacttatc tacctatg                                                       18

<210> SEQ ID NO 24
<211> LENGTH: 18
<212> TYPE: DNA
<213> ORGANISM: Homo sapiens

<400> SEQUENCE: 24
cctttccatc atacttag                                                       18

<210> SEQ ID NO 25
<211> LENGTH: 18
<212> TYPE: DNA
<213> ORGANISM: Homo sapiens

<400> SEQUENCE: 25
gatgataaat attgatgt                                                       18

<210> SEQ ID NO 26
<211> LENGTH: 18
<212> TYPE: DNA
<213> ORGANISM: Homo sapiens

<400> SEQUENCE: 26
aagcactaca caggccac                                                       18

<210> SEQ ID NO 27
<211> LENGTH: 19
<212> TYPE: DNA
<213> ORGANISM: Homo sapiens

<400> SEQUENCE: 27
tgtcctccct ctcgtggta                                                      19

<210> SEQ ID NO 28
<211> LENGTH: 19
<212> TYPE: DNA
<213> ORGANISM: Homo sapiens

<400> SEQUENCE: 28
gattaaagaa ggtgtgtct                                                      19

<210> SEQ ID NO 29
<211> LENGTH: 19
<212> TYPE: DNA
<213> ORGANISM: Homo sapiens

<400> SEQUENCE: 29
ggctactctt gttagtttg                                                      19
```

```
<210> SEQ ID NO 30
<211> LENGTH: 19
<212> TYPE: DNA
<213> ORGANISM: Homo sapiens

<400> SEQUENCE: 30
gtctggttcc tccaagaag                                                19

<210> SEQ ID NO 31
<211> LENGTH: 20
<212> TYPE: DNA
<213> ORGANISM: Homo sapiens

<400> SEQUENCE: 31
cttacatgat accttcaggc                                               20

<210> SEQ ID NO 32
<211> LENGTH: 20
<212> TYPE: DNA
<213> ORGANISM: Homo sapiens

<400> SEQUENCE: 32
caagaagcag actggagatg                                               20

<210> SEQ ID NO 33
<211> LENGTH: 20
<212> TYPE: DNA
<213> ORGANISM: Homo sapiens

<400> SEQUENCE: 33
ttgacctgaa cagcaagttt                                               20

<210> SEQ ID NO 34
<211> LENGTH: 20
<212> TYPE: DNA
<213> ORGANISM: Homo sapiens

<400> SEQUENCE: 34
ggtgggtggt cagctgcaac                                               20

<210> SEQ ID NO 35
<211> LENGTH: 24
<212> TYPE: DNA
<213> ORGANISM: Homo sapiens

<400> SEQUENCE: 35
agctacatca cacaccttga ctgg                                          24

<210> SEQ ID NO 36
<211> LENGTH: 24
<212> TYPE: DNA
<213> ORGANISM: Homo sapiens

<400> SEQUENCE: 36
agcttgctca gcttgtactc aggg                                          24

<210> SEQ ID NO 37
<211> LENGTH: 16
<212> TYPE: DNA
<213> ORGANISM: Homo sapiens

<400> SEQUENCE: 37
cttccatggg aatcag                                                   16
```

<210> SEQ ID NO 38
<211> LENGTH: 16
<212> TYPE: DNA
<213> ORGANISM: Homo sapiens

<400> SEQUENCE: 38
ttgcagctcc tggtgc                                                    16

<210> SEQ ID NO 39
<211> LENGTH: 16
<212> TYPE: DNA
<213> ORGANISM: Homo sapiens

<400> SEQUENCE: 39
gtagaacaga aggcac                                                    16

<210> SEQ ID NO 40
<211> LENGTH: 24
<212> TYPE: DNA
<213> ORGANISM: Homo sapiens

<400> SEQUENCE: 40
ccacacctgg gaaaggacct aaag                                           24

<210> SEQ ID NO 41
<211> LENGTH: 17
<212> TYPE: DNA
<213> ORGANISM: Homo sapiens

<400> SEQUENCE: 41
atgctgctct gaatggt                                                   17

<210> SEQ ID NO 42
<211> LENGTH: 23
<212> TYPE: DNA
<213> ORGANISM: Homo sapiens

<400> SEQUENCE: 42
aagcagtggt atcaacgcag agt                                            23

<210> SEQ ID NO 43
<211> LENGTH: 17
<212> TYPE: DNA
<213> ORGANISM: Homo sapiens

<400> SEQUENCE: 43
ggcagggagg aatatga                                                   17

<210> SEQ ID NO 44
<211> LENGTH: 22
<212> TYPE: DNA
<213> ORGANISM: Homo sapiens

<400> SEQUENCE: 44
caattacggc taccagcaac ag                                             22

<210> SEQ ID NO 45
<211> LENGTH: 18
<212> TYPE: DNA
<213> ORGANISM: Homo sapiens

<400> SEQUENCE: 45
gatagatggg catttatg                                                  18

<210> SEQ ID NO 46
<211> LENGTH: 18
<212> TYPE: DNA
<213> ORGANISM: Homo sapiens

<400> SEQUENCE: 46
cctttccatc atacttag                                                 18

<210> SEQ ID NO 47
<211> LENGTH: 18
<212> TYPE: DNA
<213> ORGANISM: Homo sapiens

<400> SEQUENCE: 47
gggaatcagt ttgtagtt                                                 18

<210> SEQ ID NO 48
<211> LENGTH: 23
<212> TYPE: DNA
<213> ORGANISM: Homo sapiens

<400> SEQUENCE: 48
tatcctcgta atgaccagct cca                                           23

<210> SEQ ID NO 49
<211> LENGTH: 19
<212> TYPE: DNA
<213> ORGANISM: Homo sapiens

<400> SEQUENCE: 49
tacttctcct ggaggcagg                                                19

<210> SEQ ID NO 50
<211> LENGTH: 24
<212> TYPE: DNA
<213> ORGANISM: Mus musculus

<400> SEQUENCE: 50
caggagagaa aggatttggc taca                                          24

<210> SEQ ID NO 51
<211> LENGTH: 19
<212> TYPE: DNA
<213> ORGANISM: Homo sapiens

<400> SEQUENCE: 51
tacaagtaaa cgtggctag                                                19

<210> SEQ ID NO 52
<211> LENGTH: 19
<212> TYPE: DNA
<213> ORGANISM: Homo sapiens

<400> SEQUENCE: 52
cttccggcgg tacactgca                                                19

<210> SEQ ID NO 53
<211> LENGTH: 20
<212> TYPE: DNA
<213> ORGANISM: Homo sapiens

<400> SEQUENCE: 53

```
ctgttaaagt gaacactttc                                           20

<210> SEQ ID NO 54
<211> LENGTH: 20
<212> TYPE: DNA
<213> ORGANISM: Homo sapiens

<400> SEQUENCE: 54
acatggcctg gcagcctggc                                           20

<210> SEQ ID NO 55
<211> LENGTH: 20
<212> TYPE: DNA
<213> ORGANISM: Homo sapiens

<400> SEQUENCE: 55
gtgtcttaat gtttttcagt                                           20

<210> SEQ ID NO 56
<211> LENGTH: 21
<212> TYPE: DNA
<213> ORGANISM: Mus musculus

<400> SEQUENCE: 56
tccaccctgg atcatgaagt c                                         21

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 57
ggggaattca tggacggttt cgccggc                                   27

<210> SEQ ID NO 58
<211> LENGTH: 30
<212> TYPE: DNA
<213> ORGANISM: Homo sapiens

<400> SEQUENCE: 58
cggcggtaca agtacaatat ttcatagtct                                30

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 59
aaggaattcg gtttcgccgg cagtctc                                   27

<210> SEQ ID NO 60
<211> LENGTH: 27
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 60
```
agagaattca gtgtgcgacc gagctca                                       27

<210> SEQ ID NO 61
<211> LENGTH: 16
<212> TYPE: DNA
<213> ORGANISM: Homo sapiens

<400> SEQUENCE: 61
tggagcggca attcac                                                   16

<210> SEQ ID NO 62
<211> LENGTH: 16
<212> TYPE: DNA
<213> ORGANISM: Homo sapiens

<400> SEQUENCE: 62
aaagcagtag ttgggg                                                   16

<210> SEQ ID NO 63
<211> LENGTH: 16
<212> TYPE: DNA
<213> ORGANISM: Homo sapiens

<400> SEQUENCE: 63
ggggaatgga gatgtt                                                   16

<210> SEQ ID NO 64
<211> LENGTH: 16
<212> TYPE: DNA
<213> ORGANISM: Homo sapiens

<400> SEQUENCE: 64
tttccgcggc acctcc                                                   16

<210> SEQ ID NO 65
<211> LENGTH: 17
<212> TYPE: DNA
<213> ORGANISM: Homo sapiens

<400> SEQUENCE: 65
ctaacaagaa aacaggg                                                  17

<210> SEQ ID NO 66
<211> LENGTH: 17
<212> TYPE: DNA
<213> ORGANISM: Homo sapiens

<400> SEQUENCE: 66
ggaggaggtc ttgccag                                                  17

<210> SEQ ID NO 67
<211> LENGTH: 17
<212> TYPE: DNA
<213> ORGANISM: Homo sapiens

<400> SEQUENCE: 67
cttctggacc tggagcg                                                  17

<210> SEQ ID NO 68
<211> LENGTH: 17
<212> TYPE: DNA
<213> ORGANISM: Homo sapiens

<400> SEQUENCE: 68

```
gggttgtagt cggtcat                                                    17

<210> SEQ ID NO 69
<211> LENGTH: 18
<212> TYPE: DNA
<213> ORGANISM: Homo sapiens

<400> SEQUENCE: 69
ggctgtggag tttcaccc                                                   18

<210> SEQ ID NO 70
<211> LENGTH: 18
<212> TYPE: DNA
<213> ORGANISM: Homo sapiens

<400> SEQUENCE: 70
agctcctggt gcttccgg                                                   18

<210> SEQ ID NO 71
<211> LENGTH: 18
<212> TYPE: DNA
<213> ORGANISM: Homo sapiens

<400> SEQUENCE: 71
cccaacagat gcaaatac                                                   18

<210> SEQ ID NO 72
<211> LENGTH: 18
<212> TYPE: DNA
<213> ORGANISM: Homo sapiens

<400> SEQUENCE: 72
tcagggctct gcagctcc                                                   18

<210> SEQ ID NO 73
<211> LENGTH: 19
<212> TYPE: DNA
<213> ORGANISM: Homo sapiens

<400> SEQUENCE: 73
gacaacaaat gaagttgtt                                                  19

<210> SEQ ID NO 74
<211> LENGTH: 19
<212> TYPE: DNA
<213> ORGANISM: Homo sapiens

<400> SEQUENCE: 74
atctgcatgg cttgcagct                                                  19

<210> SEQ ID NO 75
<211> LENGTH: 19
<212> TYPE: DNA
<213> ORGANISM: Homo sapiens

<400> SEQUENCE: 75
ccataattac atgcggtaa                                                  19

<210> SEQ ID NO 76
<211> LENGTH: 19
<212> TYPE: DNA
<213> ORGANISM: Homo sapiens
```

```
<400> SEQUENCE: 76
gagcttgctc agcttgtac                                                    19

<210> SEQ ID NO 77
<211> LENGTH: 20
<212> TYPE: DNA
<213> ORGANISM: Homo sapiens

<400> SEQUENCE: 77
gtgtttagca ttcttgggga                                                   20

<210> SEQ ID NO 78
<211> LENGTH: 20
<212> TYPE: DNA
<213> ORGANISM: Homo sapiens

<400> SEQUENCE: 78
gaccccgaat gagggtgatg                                                   20

<210> SEQ ID NO 79
<211> LENGTH: 20
<212> TYPE: DNA
<213> ORGANISM: Homo sapiens

<400> SEQUENCE: 79
gggaattttt gggaaatatg                                                   20

<210> SEQ ID NO 80
<211> LENGTH: 20
<212> TYPE: DNA
<213> ORGANISM: Homo sapiens

<400> SEQUENCE: 80
cctccttcag gtcactgatg                                                   20

<210> SEQ ID NO 81
<211> LENGTH: 16
<212> TYPE: DNA
<213> ORGANISM: Homo sapiens

<400> SEQUENCE: 81
cctggctgta ggatct                                                       16

<210> SEQ ID NO 82
<211> LENGTH: 16
<212> TYPE: DNA
<213> ORGANISM: Homo sapiens

<400> SEQUENCE: 82
aaagcagtag ttgggg                                                       16

<210> SEQ ID NO 83
<211> LENGTH: 16
<212> TYPE: DNA
<213> ORGANISM: Homo sapiens

<400> SEQUENCE: 83
gtggccatag gaacgc                                                       16

<210> SEQ ID NO 84
<211> LENGTH: 16
<212> TYPE: DNA
<213> ORGANISM: Homo sapiens
```

```
<400> SEQUENCE: 84
gtgcttccgg cggtac                                                       16

<210> SEQ ID NO 85
<211> LENGTH: 17
<212> TYPE: DNA
<213> ORGANISM: Homo sapiens

<400> SEQUENCE: 85
ctcaatagat ggtacct                                                      17

<210> SEQ ID NO 86
<211> LENGTH: 17
<212> TYPE: DNA
<213> ORGANISM: Homo sapiens

<400> SEQUENCE: 86
gggttgtagt cggtcat                                                      17

<210> SEQ ID NO 87
<211> LENGTH: 17
<212> TYPE: DNA
<213> ORGANISM: Homo sapiens

<400> SEQUENCE: 87
gctctctgtg atgcgct                                                      17

<210> SEQ ID NO 88
<211> LENGTH: 17
<212> TYPE: DNA
<213> ORGANISM: Homo sapiens

<400> SEQUENCE: 88
ggtgcggagc ttgctca                                                      17

<210> SEQ ID NO 89
<211> LENGTH: 18
<212> TYPE: DNA
<213> ORGANISM: Homo sapiens

<400> SEQUENCE: 89
caggcaggtg gtttgttc                                                     18

<210> SEQ ID NO 90
<211> LENGTH: 18
<212> TYPE: DNA
<213> ORGANISM: Homo sapiens

<400> SEQUENCE: 90
agctcctggt gcttccgg                                                     18

<210> SEQ ID NO 91
<211> LENGTH: 18
<212> TYPE: DNA
<213> ORGANISM: Homo sapiens

<400> SEQUENCE: 91
ggaatgaaca gctctctg                                                     18

<210> SEQ ID NO 92
<211> LENGTH: 18
<212> TYPE: DNA
```

```
<213> ORGANISM: Homo sapiens

<400> SEQUENCE: 92
tcggtcatga tggtcgag                                                      18

<210> SEQ ID NO 93
<211> LENGTH: 19
<212> TYPE: DNA
<213> ORGANISM: Homo sapiens

<400> SEQUENCE: 93
ggatgcagaa accagagat                                                     19

<210> SEQ ID NO 94
<211> LENGTH: 19
<212> TYPE: DNA
<213> ORGANISM: Homo sapiens

<400> SEQUENCE: 94
atctgcatgg cttgcagct                                                     19

<210> SEQ ID NO 95
<211> LENGTH: 19
<212> TYPE: DNA
<213> ORGANISM: Homo sapiens

<400> SEQUENCE: 95
ggaacgcact caggcaggt                                                     19

<210> SEQ ID NO 96
<211> LENGTH: 19
<212> TYPE: DNA
<213> ORGANISM: Homo sapiens

<400> SEQUENCE: 96
ctcagggctc tgcagctcc                                                     19

<210> SEQ ID NO 97
<211> LENGTH: 20
<212> TYPE: DNA
<213> ORGANISM: Homo sapiens

<400> SEQUENCE: 97
ctatccacac agacgggaat                                                    20

<210> SEQ ID NO 98
<211> LENGTH: 20
<212> TYPE: DNA
<213> ORGANISM: Homo sapiens

<400> SEQUENCE: 98
gcttgtactc agggctctgc                                                    20

<210> SEQ ID NO 99
<211> LENGTH: 20
<212> TYPE: DNA
<213> ORGANISM: Homo sapiens

<400> SEQUENCE: 99
gtagtctctg aaaatggaag                                                    20

<210> SEQ ID NO 100
<211> LENGTH: 20
```

```
<212> TYPE: DNA
<213> ORGANISM: Homo sapiens

<400> SEQUENCE: 100
tcttgccagc aaagcagtag                                                  20

<210> SEQ ID NO 101
<211> LENGTH: 30
<212> TYPE: DNA
<213> ORGANISM: Homo sapiens

<400> SEQUENCE: 101
atattgtact tgtaccgccg gaagcaccag                                       30

<210> SEQ ID NO 102
<211> LENGTH: 27
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 102
gggtctagat cagggcccag gctggtt                                          27

<210> SEQ ID NO 103
<211> LENGTH: 35
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 103
ccctgcaagt ggctgtgatg acgctgcctg aagtg                                 35

<210> SEQ ID NO 104
<211> LENGTH: 35
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 104
cacttcaggc agcgtcatca cagccacttg caggg                                 35

<210> SEQ ID NO 105
<211> LENGTH: 24
<212> TYPE: DNA
<213> ORGANISM: Homo sapiens

<400> SEQUENCE: 105
tcgtgactca agagctgaca ggcg                                             24

<210> SEQ ID NO 106
<211> LENGTH: 24
<212> TYPE: DNA
<213> ORGANISM: Homo sapiens

<400> SEQUENCE: 106
attcgagcat caccttctcc ccag                                             24

<210> SEQ ID NO 107
<211> LENGTH: 24
```

```
<212> TYPE: DNA
<213> ORGANISM: Homo sapiens

<400> SEQUENCE: 107
tgacatcttt atgcttgtct gcag                                              24

<210> SEQ ID NO 108
<211> LENGTH: 24
<212> TYPE: DNA
<213> ORGANISM: Homo sapiens

<400> SEQUENCE: 108
attatgagga gagaactcag cgac                                              24

<210> SEQ ID NO 109
<211> LENGTH: 24
<212> TYPE: DNA
<213> ORGANISM: Homo sapiens

<400> SEQUENCE: 109
gtgtcgctga gttctctcct cata                                              24

<210> SEQ ID NO 110
<211> LENGTH: 24
<212> TYPE: DNA
<213> ORGANISM: Homo sapiens

<400> SEQUENCE: 110
ggtggagtca tgcttatatg gagc                                              24

<210> SEQ ID NO 111
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized sense strand of siRNA-1
<220> FEATURE:
<221> NAME/KEY: misc_feature
<222> LOCATION: (1)..(13)
<223> OTHER INFORMATION: RNA
<220> FEATURE:
<221> NAME/KEY: misc_feature
<222> LOCATION: (14)..(21)
<223> OTHER INFORMATION: DNA

<400> SEQUENCE: 111
ugggaaagga ccuaaagtgt a                                                 21

<210> SEQ ID NO 112
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized antisense strand of siRNA-1
<220> FEATURE:
<221> NAME/KEY: misc_feature
<222> LOCATION: (1)..(6)
<223> OTHER INFORMATION: DNA
<220> FEATURE:
<221> NAME/KEY: misc_feature
<222> LOCATION: (7)..(21)
<223> OTHER INFORMATION: RNA

<400> SEQUENCE: 112
cactttaggu ccuuucccag g                                                 21
```

```
<210> SEQ ID NO 113
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized sense strand of siRNA-2
<220> FEATURE:
<221> NAME/KEY: misc_feature
<222> LOCATION: (1)..(13)
<223> OTHER INFORMATION: RNA
<220> FEATURE:
<221> NAME/KEY: misc_feature
<222> LOCATION: (14)..(21)
<223> OTHER INFORMATION: DNA

<400> SEQUENCE: 113
gggaaaggac cuaaagtgta c                                              21

<210> SEQ ID NO 114
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized antisense strand of siRNA-2
<220> FEATURE:
<221> NAME/KEY: misc_feature
<222> LOCATION: (1)..(6)
<223> OTHER INFORMATION: DNA
<220> FEATURE:
<221> NAME/KEY: misc_feature
<222> LOCATION: (7)..(21)
<223> OTHER INFORMATION: RNA

<400> SEQUENCE: 114
acacttuagg uccuuuccca g                                              21

<210> SEQ ID NO 115
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized sense strand of siRNA-3
<220> FEATURE:
<221> NAME/KEY: misc_feature
<222> LOCATION: (1)..(13)
<223> OTHER INFORMATION: RNA
<220> FEATURE:
<221> NAME/KEY: misc_feature
<222> LOCATION: (14)..(21)
<223> OTHER INFORMATION: DNA

<400> SEQUENCE: 115
ggaccuaaag uguaccgccg g                                              21

<210> SEQ ID NO 116
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized antisense strand of siRNA-3
<220> FEATURE:
<221> NAME/KEY: misc_feature
<222> LOCATION: (1)..(6)
<223> OTHER INFORMATION: DNA
<220> FEATURE:
<221> NAME/KEY: misc_feature
<222> LOCATION: (7)..(21)
<223> OTHER INFORMATION: RNA
```

```
<400> SEQUENCE: 116
ggcggtacac uuuagguccu u                                              21

<210> SEQ ID NO 117
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized sense strand of siRNA-4
<220> FEATURE:
<221> NAME/KEY: misc_feature
<222> LOCATION: (1)..(13)
<223> OTHER INFORMATION: RNA
<220> FEATURE:
<221> NAME/KEY: misc_feature
<222> LOCATION: (14)..(21)
<223> OTHER INFORMATION: DNA

<400> SEQUENCE: 117
ccuaaagugu accgccggaa g                                              21

<210> SEQ ID NO 118
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized antisense strand of siRNA-4
<220> FEATURE:
<221> NAME/KEY: misc_feature
<222> LOCATION: (1)..(6)
<223> OTHER INFORMATION: DNA
<220> FEATURE:
<221> NAME/KEY: misc_feature
<222> LOCATION: (7)..(21)
<223> OTHER INFORMATION: RNA

<400> SEQUENCE: 118
tccggcggua cacuuuaggu c                                              21

<210> SEQ ID NO 119
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized sense strand of siRNA-5
<220> FEATURE:
<221> NAME/KEY: misc_feature
<222> LOCATION: (1)..(13)
<223> OTHER INFORMATION: RNA
<220> FEATURE:
<221> NAME/KEY: misc_feature
<222> LOCATION: (14)..(21)
<223> OTHER INFORMATION: DNA

<400> SEQUENCE: 119
aaaguguacc gccggaagca c                                              21

<210> SEQ ID NO 120
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized antisense strand of siRNA-5
<220> FEATURE:
<221> NAME/KEY: misc_feature
<222> LOCATION: (1)..(6)
```

```
<223> OTHER INFORMATION: DNA
<220> FEATURE:
<221> NAME/KEY: misc_feature
<222> LOCATION: (7)..(21)
<223> OTHER INFORMATION: RNA

<400> SEQUENCE: 120
gcttccggcg guacacuuua g                                              21

<210> SEQ ID NO 121
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized sense strand of siRNA-6
<220> FEATURE:
<221> NAME/KEY: misc_feature
<222> LOCATION: (1)..(13)
<223> OTHER INFORMATION: RNA
<220> FEATURE:
<221> NAME/KEY: misc_feature
<222> LOCATION: (14)..(21)
<223> OTHER INFORMATION: DNA

<400> SEQUENCE: 121
aaguguaccg ccggaagcac c                                              21

<210> SEQ ID NO 122
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized antisense strand of siRNA-6
<220> FEATURE:
<221> NAME/KEY: misc_feature
<222> LOCATION: (1)..(6)
<223> OTHER INFORMATION: DNA
<220> FEATURE:
<221> NAME/KEY: misc_feature
<222> LOCATION: (7)..(21)
<223> OTHER INFORMATION: RNA

<400> SEQUENCE: 122
tgcttccggc gguacacuuu a                                              21

<210> SEQ ID NO 123
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized sense strand of siRNA-7
<220> FEATURE:
<221> NAME/KEY: misc_feature
<222> LOCATION: (1)..(13)
<223> OTHER INFORMATION: RNA
<220> FEATURE:
<221> NAME/KEY: misc_feature
<222> LOCATION: (14)..(21)
<223> OTHER INFORMATION: DNA

<400> SEQUENCE: 123
ggccuguaua ccggataatg a                                              21

<210> SEQ ID NO 124
<211> LENGTH: 21
<212> TYPE: DNA/RNA
<213> ORGANISM: Artificial Sequence
<220> FEATURE:
```

```
<223> OTHER INFORMATION: Description of Artificial Sequence: an
      artificial synthesized antisense strand of siRNA-7
<220> FEATURE:
<221> NAME/KEY: misc_feature
<222> LOCATION: (1)..(6)
<223> OTHER INFORMATION: DNA
<220> FEATURE:
<221> NAME/KEY: misc_feature
<222> LOCATION: (7)..(21)
<223> OTHER INFORMATION: RNA

<400> SEQUENCE: 124
attatccggu auacaggccc a                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: an
      artificial synthesized sense strand of siRNA-8

<400> SEQUENCE: 125
ggccuguaua ccggauaaug a                                              21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: an
      artificial synthesized antisense strand of siRNA-8

<400> SEQUENCE: 126
auuauccggu auacaggccc a                                              21

<210> SEQ ID NO 127
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized sense strand of siRNA-9
<220> FEATURE:
<221> NAME/KEY: misc_feature
<222> LOCATION: (1)..(13)
<223> OTHER INFORMATION: RNA
<220> FEATURE:
<221> NAME/KEY: misc_feature
<222> LOCATION: (14)..(21)
<223> OTHER INFORMATION: DNA

<400> SEQUENCE: 127
cggcugcaau cgattgatag c                                              21

<210> SEQ ID NO 128
<211> LENGTH: 21
<212> TYPE: DNA/RNA
<213> ORGANISM: Artificial Sequence
<220> FEATURE:
<223> OTHER INFORMATION: Description of Artificial Sequence: an
      artificial synthesized antisense strand of siRNA-9
<220> FEATURE:
<221> NAME/KEY: misc_feature
<222> LOCATION: (1)..(6)
<223> OTHER INFORMATION: DNA
<220> FEATURE:
<221> NAME/KEY: misc_feature
<222> LOCATION: (7)..(21)
<223> OTHER INFORMATION: RNA
```

```
<400> SEQUENCE: 128
tatcaaucga uugcagccga a                                              21

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 129
aagcttatgg acggtttcgc cggc                                           24

<210> SEQ ID NO 130
<211> LENGTH: 19
<212> TYPE: DNA
<213> ORGANISM: Homo sapiens

<400> SEQUENCE: 130
taactgctcg agggcttgg                                                 19

<210> SEQ ID NO 131
<211> LENGTH: 28
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 131
gggctcgaga agcttatgga cggtttcg                                       28
```